(12) United States Patent
Duong et al.

(10) Patent No.: US 12,109,223 B2
(45) Date of Patent: Oct. 8, 2024

(54) POLYMER NANOPARTICLE AND DNA NANOSTRUCTURE COMPOSITIONS AND METHODS FOR NON-VIRAL DELIVERY

(71) Applicant: BATTELLE MEMORIAL INSTITUTE, Columbus, OH (US)

(72) Inventors: Anthony D. Duong, Columbus, OH (US); Cherry Gupta, Columbus, OH (US); Kenneth R. Sims, Jr., Columbus, OH (US); Danielle Huk, Columbus, OH (US); Jacob Lilly, Columbus, OH (US); Stephanie M. Kute, Columbus, OH (US); Mike Koeris, Columbus, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 0 days.

(21) Appl. No.: 18/444,146

(22) Filed: Feb. 16, 2024

(65) Prior Publication Data

US 2024/0189338 A1 Jun. 13, 2024

Related U.S. Application Data

(63) Continuation of application No. 17/542,055, filed on Dec. 3, 2021.

(60) Provisional application No. 63/121,202, filed on Dec. 3, 2020.

(51) Int. Cl.
| | |
|---|---|
| *A61K 47/60* | (2017.01) |
| *A61K 31/7088* | (2006.01) |
| *A61K 47/69* | (2017.01) |
| *C08F 293/00* | (2006.01) |
| *C12N 15/113* | (2010.01) |
| *B82Y 5/00* | (2011.01) |
| *B82Y 30/00* | (2011.01) |
| *B82Y 35/00* | (2011.01) |
| *B82Y 40/00* | (2011.01) |

(52) U.S. Cl.
CPC .......... *A61K 31/7088* (2013.01); *A61K 47/60* (2017.08); *A61K 47/6935* (2017.08); *C08F 293/005* (2013.01); *C12N 15/113* (2013.01); *B82Y 5/00* (2013.01); *B82Y 30/00* (2013.01); *B82Y 35/00* (2013.01); *B82Y 40/00* (2013.01); *C08F 2438/03* (2013.01); *C12N 2310/11* (2013.01); *C12N 2310/531* (2013.01)

(58) Field of Classification Search
USPC ........................................................ 528/332
See application file for complete search history.

(56) References Cited

U.S. PATENT DOCUMENTS

| | | |
|---|---|---|
| 3,562,806 A | 2/1971 | Grant et al. |
| 3,678,098 A | 7/1972 | Lewis et al. |
| 3,691,123 A | 9/1972 | Clarke et al. |
| 3,706,564 A | 12/1972 | Perry et al. |
| 3,706,565 A | 12/1972 | Harris |
| 3,739,042 A | 6/1973 | Chu et al. |
| 3,744,969 A | 7/1973 | Alps et al. |
| 3,829,564 A | 8/1974 | Merry et al. |
| 3,847,857 A | 11/1974 | Haag et al. |
| 4,036,766 A | 7/1977 | Yamamoto et al. |
| 4,056,559 A | 11/1977 | Lewis et al. |
| 4,219,616 A | 8/1980 | Pope et al. |
| 4,237,253 A | 12/1980 | Jacquet et al. |
| 4,377,481 A | 3/1983 | Jakabhazy |
| 4,434,268 A | 2/1984 | Doroszkowsky et al. |
| 4,544,621 A | 10/1985 | Roth |
| 4,557,997 A | 12/1985 | Iwasaki et al. |
| 4,559,293 A | 12/1985 | Moriya et al. |
| 4,592,816 A | 6/1986 | Emmons et al. |
| 4,595,722 A | 6/1986 | Such |
| 4,656,027 A | 4/1987 | Sjoovist |
| 4,735,887 A | 4/1988 | Foss et al. |
| 4,755,563 A | 7/1988 | West |
| 4,775,721 A | 10/1988 | Horikawa et al. |
| 4,834,799 A | 5/1989 | Song, II |
| 4,855,207 A | 8/1989 | Tsubuko et al. |
| 4,925,764 A | 5/1990 | Madeleine et al. |

(Continued)

FOREIGN PATENT DOCUMENTS

| | | |
|---|---|---|
| CN | 1323840 A | 11/2001 |
| CN | 1328106 A | 12/2001 |

(Continued)

OTHER PUBLICATIONS

Cheng C, Convertine AJ, Stayton PS, Bryers JD. Multifunctional triblock copolymers for intracellular messenger RNA delivery. Biomaterials. Oct. 2012;33(28):6868-76. doi: 10.1016/j.biomaterials. 2012.06.020. Epub Jul. 9, 2012. PMID: 22784603; PMCID: PMC3412061.

(Continued)

*Primary Examiner* — Terressa Boykin
(74) *Attorney, Agent, or Firm* — Barnes & Thornburg LLP

(57) ABSTRACT

The invention relates to polymer nanoparticle and DNA nanostructure delivery compositions for non-viral delivery, and methods therefor. More particularly, the invention relates to polymer nanoparticle delivery compositions, such as reversible addition-fragmentation chain transfer (RAFT) polymer compositions, and DNA nanostructure delivery compositions, such as DNA origami compositions, for the delivery of more than one payload, or for the delivery of a nucleic acid construct payload of 3 kB or more, and methods therefor.

30 Claims, 19 Drawing Sheets

(56) References Cited

U.S. PATENT DOCUMENTS

| | | |
|---|---|---|
| 4,985,160 A | 1/1991 | Henry et al. |
| 5,085,698 A | 2/1992 | Ma et al. |
| 5,124,381 A | 6/1992 | Ward |
| 5,141,556 A | 8/1992 | Matrick |
| 5,180,425 A | 1/1993 | Matrick et al. |
| 5,205,861 A | 4/1993 | Matrick |
| 5,271,765 A | 12/1993 | Ma |
| 5,310,595 A | 5/1994 | Ali et al. |
| 5,310,778 A | 5/1994 | Shor et al. |
| 5,418,277 A | 5/1995 | Ma et al. |
| 5,428,383 A | 6/1995 | Shields et al. |
| 5,432,035 A | 7/1995 | Katagiri et al. |
| 5,512,418 A | 4/1996 | Ma |
| 5,518,534 A | 5/1996 | Pearlstine et al. |
| 5,519,081 A | 5/1996 | Ashton et al. |
| 5,519,085 A | 5/1996 | Ma et al. |
| 5,525,450 A | 6/1996 | Spiewak et al. |
| 5,620,883 A | 4/1997 | Shao et al. |
| 5,698,016 A | 12/1997 | Adams et al. |
| 5,709,714 A | 1/1998 | Natoli et al. |
| 5,750,594 A | 5/1998 | Page et al. |
| 5,969,046 A | 10/1999 | Schindler et al. |
| 5,985,573 A | 11/1999 | Hennink et al. |
| 6,004,582 A | 12/1999 | Faour et al. |
| 6,004,712 A | 12/1999 | Barbetta et al. |
| 6,022,533 A | 2/2000 | Goto et al. |
| 6,022,908 A | 2/2000 | Ma et al. |
| 6,040,358 A | 3/2000 | Page et al. |
| 6,077,635 A | 6/2000 | Okado et al. |
| 6,132,917 A | 10/2000 | Hoffend et al. |
| 6,139,856 A | 10/2000 | Kaminska et al. |
| 6,197,290 B1 | 3/2001 | Goto et al. |
| 6,207,631 B1 | 3/2001 | Kasturi et al. |
| 6,221,402 B1 | 4/2001 | Itoh et al. |
| 6,245,421 B1 | 6/2001 | Aurenty et al. |
| 6,247,808 B1 | 6/2001 | Ma et al. |
| 6,251,554 B1 | 6/2001 | Hoffend et al. |
| 6,276,273 B1 | 8/2001 | Aurenty et al. |
| 6,309,666 B1 | 10/2001 | Hatano et al. |
| 6,315,854 B1 | 11/2001 | Anhauser et al. |
| 6,372,708 B1 | 4/2002 | Kasturi et al. |
| 6,413,306 B1 | 7/2002 | Kraiter et al. |
| 6,471,349 B1 | 10/2002 | Aurenty et al. |
| 6,532,871 B1 | 3/2003 | Aurenty et al. |
| 6,624,210 B1 | 9/2003 | Petereit et al. |
| 6,692,769 B1 | 2/2004 | Ishibashi et al. |
| 6,720,387 B1 | 4/2004 | Stark et al. |
| 6,794,367 B1 | 9/2004 | Tanida et al. |
| 6,827,795 B1 | 12/2004 | Kasturi et al. |
| 6,903,064 B1 | 6/2005 | Kasturi et al. |
| 7,256,020 B2 | 8/2007 | Lyamichev et al. |
| 7,737,108 B1 | 6/2010 | Hoffman et al. |
| 8,758,860 B1 | 6/2014 | Pyles et al. |
| 9,085,618 B2 | 7/2015 | Ramasubramanyan et al. |
| 9,447,220 B2 | 9/2016 | Cho et al. |
| 9,714,940 B2 | 7/2017 | Lowery, Jr. et al. |
| 9,970,040 B2 | 5/2018 | Elbaz et al. |
| 10,201,503 B1 | 2/2019 | Li et al. |
| 10,695,443 B2 | 6/2020 | Lötvall et al. |
| 11,419,932 B2 | 8/2022 | Bathe et al. |
| 2002/0028410 A1 | 3/2002 | Choi |
| 2002/0187311 A1 | 12/2002 | Golub et al. |
| 2003/0049311 A1 | 3/2003 | McAllister et al. |
| 2003/0064036 A1 | 4/2003 | Petereit et al. |
| 2003/0071883 A1 | 4/2003 | Suzuki et al. |
| 2003/0106160 A1 | 6/2003 | Sun et al. |
| 2003/0124074 A1 | 7/2003 | Mougin et al. |
| 2003/0130160 A1 | 7/2003 | Eason et al. |
| 2003/0152856 A1 | 8/2003 | Mizoe et al. |
| 2003/0199419 A1 | 10/2003 | Rodrigues et al. |
| 2004/0091538 A1 | 5/2004 | Pollock-Dove et al. |
| 2004/0096490 A1 | 5/2004 | Bracht et al. |
| 2004/0104501 A1 | 6/2004 | Petereit et al. |
| 2004/0109869 A1 | 6/2004 | Glenn et al. |
| 2004/0198838 A1 | 10/2004 | Alles et al. |
| 2004/0208925 A1 | 10/2004 | Oner et al. |
| 2004/0219211 A1 | 11/2004 | Criere et al. |
| 2004/0249035 A1 | 12/2004 | Petereit et al. |
| 2005/0020779 A1 | 1/2005 | Mougin et al. |
| 2005/0026803 A1 | 2/2005 | Sivik et al. |
| 2005/0048112 A1 | 3/2005 | Breitenbach et al. |
| 2005/0053566 A1 | 3/2005 | Nguyen-Kim et al. |
| 2005/0070486 A1 | 3/2005 | Wieland-Berghausen et al. |
| 2005/0084529 A1 | 4/2005 | Rosenberg et al. |
| 2005/0090599 A1 | 4/2005 | Spinelli |
| 2005/0208133 A1 | 9/2005 | Tsutsumi et al. |
| 2005/0281871 A1 | 12/2005 | Petereit et al. |
| 2006/0051412 A1 | 3/2006 | Petereit et al. |
| 2006/0089425 A1 | 4/2006 | Chopra et al. |
| 2006/0110433 A1 | 5/2006 | Terahara et al. |
| 2006/0257484 A1 | 11/2006 | Hwang et al. |
| 2006/0280798 A1 | 12/2006 | Ensoli |
| 2007/0027213 A1 | 2/2007 | Oberegger et al. |
| 2007/0072996 A1 | 3/2007 | Kedar et al. |
| 2007/0088118 A1 | 4/2007 | Dungworth et al. |
| 2007/0141013 A1 | 6/2007 | Nguyen-Kim et al. |
| 2007/0178059 A1 | 8/2007 | Moser et al. |
| 2007/0203245 A1 | 8/2007 | Koltun et al. |
| 2007/0231397 A1 | 10/2007 | Petereit et al. |
| 2007/0259028 A1 | 11/2007 | Ito |
| 2007/0275060 A1 | 11/2007 | Befumo et al. |
| 2007/0275071 A1 | 11/2007 | Ensoli et al. |
| 2008/0050432 A1 | 2/2008 | Jun et al. |
| 2008/0050450 A1 | 2/2008 | Arnold et al. |
| 2008/0075689 A1 | 3/2008 | Pierobon et al. |
| 2008/0089853 A1 | 4/2008 | Nguyen-Kim et al. |
| 2008/0153982 A1 | 6/2008 | Lai et al. |
| 2008/0181948 A1 | 7/2008 | Berndl et al. |
| 2008/0193405 A1 | 8/2008 | Mukherjee et al. |
| 2008/0193544 A1 | 8/2008 | Bruck-Scheffler et al. |
| 2008/0226731 A1 | 9/2008 | Vasanthavada et al. |
| 2008/0233177 A1 | 9/2008 | Meconi |
| 2008/0280999 A1 | 11/2008 | Lakshman |
| 2008/0286221 A1 | 11/2008 | Kim et al. |
| 2008/0299391 A1 | 12/2008 | White et al. |
| 2008/0306233 A1 | 12/2008 | Muhrer et al. |
| 2009/0023754 A1 | 1/2009 | Lee et al. |
| 2009/0053315 A1 | 2/2009 | Brough et al. |
| 2009/0099075 A1 | 4/2009 | Barg et al. |
| 2009/0108241 A1 | 4/2009 | Ogura et al. |
| 2009/0118399 A1 | 5/2009 | Benbakoura et al. |
| 2009/0148522 A1 | 6/2009 | Kowalski et al. |
| 2009/0161058 A1 | 6/2009 | Sherman |
| 2009/0175952 A1 | 7/2009 | Woo et al. |
| 2009/0220596 A1 | 9/2009 | Rosenberg et al. |
| 2009/0221621 A1 | 9/2009 | Sathyan et al. |
| 2009/0280183 A1 | 11/2009 | Lizio et al. |
| 2009/0285891 A1 | 11/2009 | Jung et al. |
| 2009/0302493 A1 | 12/2009 | Kessler et al. |
| 2009/0311320 A1 | 12/2009 | Oury et al. |
| 2009/0318847 A1 | 12/2009 | Sebree et al. |
| 2009/0321945 A1 | 12/2009 | Besling |
| 2010/0038816 A1 | 2/2010 | Ghogh et al. |
| 2010/0048737 A1 | 2/2010 | Wendel et al. |
| 2010/0074951 A1 | 3/2010 | Kim et al. |
| 2010/0087544 A1 | 4/2010 | Kim et al. |
| 2010/0120970 A1 | 5/2010 | Biggs et al. |
| 2010/0143459 A1 | 6/2010 | Liepold et al. |
| 2010/0143470 A1 | 6/2010 | Kim et al. |
| 2010/0143590 A1 | 6/2010 | Held et al. |
| 2010/0152299 A1 | 6/2010 | Vasanthavada et al. |
| 2010/0160183 A1 | 6/2010 | Xu et al. |
| 2010/0174040 A1 | 7/2010 | Kim et al. |
| 2010/0209480 A1 | 8/2010 | Altenburger et al. |
| 2010/0209520 A1 | 8/2010 | Kubo |
| 2010/0233350 A1 | 9/2010 | Herrmann |
| 2010/0233447 A1 | 9/2010 | Campbell |
| 2010/0247635 A1 | 9/2010 | Rosenberg et al. |
| 2010/0266859 A1 | 10/2010 | Abe et al. |
| 2010/0272797 A1 | 10/2010 | Kim et al. |
| 2010/0278899 A1 | 11/2010 | Sugiura et al. |
| 2010/0286288 A1 | 11/2010 | Langguth et al. |
| 2010/0291311 A1 | 11/2010 | Trouve et al. |
| 2010/0310644 A1 | 12/2010 | Liebmann et al. |

(56) References Cited

U.S. PATENT DOCUMENTS

| | | |
|---|---|---|
| 2010/0323090 A1 | 12/2010 | Ishizaki et al. |
| 2011/0002988 A1 | 1/2011 | Ishizaki et al. |
| 2011/0005773 A1 | 1/2011 | Dusterhoft et al. |
| 2011/0032303 A1 | 2/2011 | Li |
| 2011/0052683 A1 | 3/2011 | Kim et al. |
| 2011/0052699 A1 | 3/2011 | Funke et al. |
| 2011/0091563 A1 | 4/2011 | Kurasawa et al. |
| 2011/0111021 A1 | 5/2011 | Kim et al. |
| 2011/0111022 A1 | 5/2011 | Kim et al. |
| 2011/0117194 A1 | 5/2011 | Kim et al. |
| 2011/0123636 A1 | 5/2011 | Stayton et al. |
| 2011/0144260 A1 | 6/2011 | Tanabe et al. |
| 2011/0201759 A1 | 8/2011 | Takahashi |
| 2011/0242154 A1 | 10/2011 | Roberts et al. |
| 2011/0257289 A1 | 10/2011 | Biggs et al. |
| 2011/0263470 A1 | 10/2011 | Qin et al. |
| 2011/0269913 A1 | 11/2011 | Balk et al. |
| 2011/0274893 A1 | 11/2011 | Kaser et al. |
| 2011/0275775 A1 | 11/2011 | Goto et al. |
| 2011/0287100 A1 | 11/2011 | Desset-Brethes et al. |
| 2011/0305660 A1 | 12/2011 | Stayton et al. |
| 2011/0306632 A1 | 12/2011 | Miller et al. |
| 2011/0312973 A1 | 12/2011 | Liepold et al. |
| 2012/0009223 A1 | 1/2012 | Wenguang et al. |
| 2012/0053248 A1 | 3/2012 | Kolter et al. |
| 2012/0093982 A1 | 4/2012 | Tsukioka et al. |
| 2012/0143039 A1 | 6/2012 | Hartwig et al. |
| 2012/0172574 A1 | 7/2012 | Helou et al. |
| 2012/0183769 A1 | 7/2012 | Nasu et al. |
| 2012/0190724 A1 | 7/2012 | Na et al. |
| 2012/0213827 A1 | 8/2012 | Chatterji et al. |
| 2012/0220550 A1 | 8/2012 | Bae et al. |
| 2012/0232117 A1 | 9/2012 | Bae et al. |
| 2012/0251583 A1 | 10/2012 | Rothemund et al. |
| 2012/0258909 A1 | 10/2012 | Liepold et al. |
| 2012/0282303 A1 | 11/2012 | Ito |
| 2012/0282310 A1 | 11/2012 | Lucet-Levannier et al. |
| 2012/0283670 A1 | 11/2012 | Ito |
| 2012/0323190 A1 | 12/2012 | Ito |
| 2012/0328891 A1 | 12/2012 | Suwa et al. |
| 2013/0005874 A1 | 1/2013 | Nakajima et al. |
| 2013/0011362 A1 | 1/2013 | Monahan et al. |
| 2013/0017245 A1 | 1/2013 | Takano |
| 2013/0034599 A1 | 2/2013 | Thaxton et al. |
| 2013/0040236 A1 | 2/2013 | Fukushima et al. |
| 2013/0085233 A1 | 4/2013 | Niitani et al. |
| 2013/0090480 A1 | 4/2013 | Park Choo et al. |
| 2013/0095168 A1 | 4/2013 | Choi et al. |
| 2013/0129869 A1 | 5/2013 | Hafezi et al. |
| 2013/0171646 A1 | 7/2013 | Park et al. |
| 2013/0172239 A1 | 7/2013 | Gao et al. |
| 2013/0224859 A1 | 8/2013 | Bachelet et al. |
| 2013/0236551 A1 | 9/2013 | Cavazza |
| 2013/0239339 A1 | 9/2013 | Bown et al. |
| 2013/0243873 A1 | 9/2013 | Aversa et al. |
| 2013/0261019 A1 | 10/2013 | Lin et al. |
| 2013/0274297 A1 | 10/2013 | Gatti et al. |
| 2013/0317096 A1 | 11/2013 | Yap et al. |
| 2014/0018404 A1 | 1/2014 | Chen et al. |
| 2014/0080868 A1 | 3/2014 | Ng et al. |
| 2014/0080869 A1 | 3/2014 | Krishnan et al. |
| 2014/0080886 A1 | 3/2014 | Pilot-Matias et al. |
| 2014/0088152 A1 | 3/2014 | Bae et al. |
| 2014/0128418 A1 | 5/2014 | Bae et al. |
| 2014/0128827 A1 | 5/2014 | Song |
| 2014/0155388 A1 | 6/2014 | Brzeczko et al. |
| 2014/0161893 A1 | 6/2014 | Shen et al. |
| 2014/0206742 A1 | 7/2014 | Lomuscio et al. |
| 2014/0235790 A1 | 8/2014 | Stayton et al. |
| 2014/0248350 A1 | 9/2014 | Reyes et al. |
| 2014/0271857 A1 | 9/2014 | Nelson et al. |
| 2014/0303334 A1 | 10/2014 | Goto et al. |
| 2015/0045353 A1 | 2/2015 | Comer et al. |
| 2015/0086624 A1 | 3/2015 | Cho et al. |
| 2015/0104408 A1 | 4/2015 | Wakefield et al. |
| 2015/0118294 A1 | 4/2015 | Song et al. |
| 2015/0132479 A1 | 5/2015 | Arfsten et al. |
| 2015/0164816 A1 | 6/2015 | Jaklenec et al. |
| 2015/0174250 A1 | 6/2015 | Griffiths et al. |
| 2015/0191132 A1 | 7/2015 | Muramoto et al. |
| 2015/0218125 A1 | 8/2015 | Bae et al. |
| 2015/0232729 A1 | 8/2015 | Zhao et al. |
| 2015/0258093 A1 | 9/2015 | Miller et al. |
| 2015/0283254 A1 | 10/2015 | Duvall et al. |
| 2015/0297526 A1 | 10/2015 | Puniya et al. |
| 2015/0374634 A1 | 12/2015 | Koo et al. |
| 2016/0045446 A1 | 2/2016 | Shibata et al. |
| 2016/0187323 A1 | 6/2016 | Farokhzad et al. |
| 2016/0193246 A1 | 7/2016 | Grandfils et al. |
| 2016/0194368 A1 | 7/2016 | Hoge et al. |
| 2016/0194625 A1 | 7/2016 | Hoge et al. |
| 2016/0220472 A1 | 8/2016 | Wang et al. |
| 2016/0243221 A1 | 8/2016 | Hoge et al. |
| 2016/0243274 A1 | 8/2016 | Chisholm et al. |
| 2016/0244501 A1 | 8/2016 | Ellsworth et al. |
| 2016/0244502 A1 | 8/2016 | Bolen et al. |
| 2016/0250170 A1 | 9/2016 | Hsu et al. |
| 2016/0279251 A1 | 9/2016 | Stayton et al. |
| 2016/0279289 A1 | 9/2016 | Chisholm et al. |
| 2016/0313566 A1 | 10/2016 | Le et al. |
| 2016/0317445 A1 | 11/2016 | Saly et al. |
| 2016/0317647 A1 | 11/2016 | Ciaramella et al. |
| 2016/0375017 A1 | 12/2016 | Asmus et al. |
| 2016/0376333 A1 | 12/2016 | Procko et al. |
| 2017/0002060 A1 | 1/2017 | Bolen et al. |
| 2017/0079932 A1 | 3/2017 | Emgenbroich et al. |
| 2017/0087174 A1 | 3/2017 | Beumont et al. |
| 2017/0105945 A1 | 4/2017 | Emgenbroich et al. |
| 2017/0119690 A1 | 5/2017 | Hansen et al. |
| 2017/0128380 A1 | 5/2017 | Wang |
| 2017/0173128 A1 | 6/2017 | Hoge et al. |
| 2017/0211023 A1 | 7/2017 | Zhang |
| 2017/0231989 A1 | 8/2017 | Hayashi et al. |
| 2017/0240765 A1 | 8/2017 | Nabuurs et al. |
| 2017/0247381 A1 | 8/2017 | Mao et al. |
| 2017/0296484 A1 | 10/2017 | Kottayil et al. |
| 2017/0304213 A1 | 10/2017 | Shi et al. |
| 2017/0327463 A1 | 11/2017 | Fung et al. |
| 2018/0031971 A1 | 2/2018 | Hustad et al. |
| 2018/0031972 A1 | 2/2018 | Hustad et al. |
| 2018/0200190 A1 | 7/2018 | Dharmadhikari et al. |
| 2018/0221295 A1 | 8/2018 | Hansen et al. |
| 2018/0221300 A1 | 8/2018 | Emgenbroich et al. |
| 2018/0221402 A1 | 8/2018 | Prieve et al. |
| 2018/0230489 A1 | 8/2018 | Kotin |
| 2018/0237800 A1 | 8/2018 | Murthy et al. |
| 2018/0318365 A1 | 11/2018 | Yeung et al. |
| 2018/0333683 A1 | 11/2018 | Liu et al. |
| 2018/0346797 A1 | 12/2018 | Kalgaonkar et al. |
| 2019/0000765 A1 | 1/2019 | Hattori et al. |
| 2019/0054069 A1 | 2/2019 | Chen et al. |
| 2019/0060425 A1 | 2/2019 | Scheel et al. |
| 2019/0070143 A1 | 3/2019 | Boulas et al. |
| 2019/0070233 A1 | 3/2019 | Yeung et al. |
| 2019/0077923 A1 | 3/2019 | Beaume et al. |
| 2019/0091339 A1 | 3/2019 | Miller et al. |
| 2019/0099381 A1 | 4/2019 | Gong et al. |
| 2019/0125663 A1 | 5/2019 | Herry et al. |
| 2019/0153471 A1 | 5/2019 | Paul et al. |
| 2019/0192691 A1 | 6/2019 | Barrett et al. |
| 2019/0194376 A1 | 6/2019 | Maejima et al. |
| 2019/0203030 A1 | 7/2019 | Cheong et al. |
| 2019/0224339 A1 | 7/2019 | Paul et al. |
| 2019/0231712 A1 | 8/2019 | Matsumoto et al. |
| 2019/0247350 A1 | 8/2019 | Mizugaki et al. |
| 2019/0254966 A1 | 8/2019 | Bellinger et al. |
| 2019/0270991 A1 | 9/2019 | Foot et al. |
| 2019/0274346 A1 | 9/2019 | Gore et al. |
| 2019/0365773 A1 | 12/2019 | Yokoyama et al. |
| 2019/0382837 A1 | 12/2019 | Spurbeck et al. |
| 2020/0016092 A1 | 1/2020 | Bernardo et al. |
| 2020/0038390 A1 | 2/2020 | Park et al. |
| 2020/0051813 A1 | 2/2020 | Osaki et al. |
| 2020/0069696 A1 | 3/2020 | Liu |

(56) References Cited

U.S. PATENT DOCUMENTS

| | | |
|---|---|---|
| 2020/0078463 A1 | 3/2020 | Park et al. |
| 2020/0086616 A1 | 3/2020 | Meise et al. |
| 2020/0123391 A1 | 4/2020 | Habets et al. |
| 2020/0129440 A1 | 4/2020 | Baek et al. |
| 2020/0138072 A1 | 5/2020 | Yucel et al. |
| 2020/0163962 A1 | 5/2020 | Jahagirdar et al. |
| 2020/0165630 A1 | 5/2020 | Paul et al. |
| 2020/0171169 A1 | 6/2020 | Duvall et al. |
| 2020/0188290 A1 | 6/2020 | Herrmann et al. |
| 2020/0197289 A1 | 6/2020 | Wang et al. |
| 2020/0206133 A1 | 7/2020 | Alsenz et al. |
| 2020/0224022 A1 | 7/2020 | Gigmes et al. |
| 2020/0261426 A1 | 8/2020 | Park et al. |
| 2020/0308331 A1 | 10/2020 | Kang et al. |
| 2020/0390752 A1 | 12/2020 | Moon et al. |
| 2021/0069111 A1 | 3/2021 | Reineke et al. |
| 2021/0128479 A1 | 5/2021 | Cheng et al. |
| 2021/0163933 A1 | 6/2021 | Budnik et al. |
| 2021/0163985 A1 | 6/2021 | Sah et al. |
| 2021/0196682 A1 | 7/2021 | Chen et al. |
| 2021/0213002 A1 | 7/2021 | Natori et al. |
| 2021/0330599 A1 | 10/2021 | Benoit et al. |
| 2021/0347950 A1 | 11/2021 | Kou et al. |
| 2021/0355454 A1 | 11/2021 | Cardinal et al. |
| 2021/0371470 A1 | 12/2021 | Murlidharan et al. |
| 2021/0373002 A1 | 12/2021 | Gopinath et al. |
| 2021/0387156 A1 | 12/2021 | Oschmann et al. |
| 2021/0387946 A1 | 12/2021 | Lindemann et al. |
| 2022/0008346 A1 | 1/2022 | Wilson et al. |
| 2022/0016098 A1 | 1/2022 | Cho et al. |
| 2022/0016271 A1 | 1/2022 | Farokhzad et al. |
| 2022/0031607 A1 | 2/2022 | Cho et al. |
| 2022/0143062 A1 | 5/2022 | Kahvejian et al. |
| 2022/0175812 A1 | 6/2022 | Duong et al. |
| 2022/0233514 A1 | 7/2022 | Choi et al. |
| 2022/0233580 A1 | 7/2022 | Takeshita et al. |
| 2022/0243225 A1 | 8/2022 | Mathur et al. |
| 2022/0291432 A1 | 9/2022 | O'Keeffe |
| 2022/0333097 A1 | 10/2022 | Duong et al. |
| 2022/0396789 A1 | 12/2022 | Banal et al. |
| 2023/0059080 A1 | 2/2023 | Lee et al. |
| 2023/0067461 A1 | 3/2023 | Lee et al. |
| 2023/0092431 A1 | 3/2023 | Isabella et al. |
| 2023/0218536 A1 | 7/2023 | Solomun et al. |
| 2023/0227687 A1 | 7/2023 | Li et al. |
| 2023/0310621 A1 | 10/2023 | Grandfils et al. |
| 2024/0067960 A1 | 2/2024 | Gupta et al. |
| 2024/0074981 A1 | 3/2024 | Gupta et al. |

FOREIGN PATENT DOCUMENTS

| | | |
|---|---|---|
| CN | 1806901 A | 7/2006 |
| CN | 1813683 A | 8/2006 |
| CN | 1896112 A | 1/2007 |
| CN | 101444513 A | 6/2009 |
| CN | 101643412 A | 2/2010 |
| CN | 101735383 A | 6/2010 |
| CN | 102030871 A | 4/2011 |
| CN | 102250278 A | 11/2011 |
| CN | 102949342 A | 3/2013 |
| CN | 103113509 A | 5/2013 |
| CN | 103255174 A | 8/2013 |
| CN | 103319668 A | 9/2013 |
| CN | 103333283 A | 10/2013 |
| CN | 103536972 A | 1/2014 |
| CN | 103755870 A | 4/2014 |
| CN | 103976972 A | 8/2014 |
| CN | 104479064 A | 4/2015 |
| CN | 104772051 A | 7/2015 |
| CN | 104784155 A | 7/2015 |
| CN | 104922078 A | 9/2015 |
| CN | 104971073 A | 10/2015 |
| CN | 105504923 A | 4/2016 |
| CN | 105833272 A | 8/2016 |
| CN | 105833287 A | 8/2016 |
| CN | 105949365 A | 9/2016 |
| CN | 106117580 A | 11/2016 |
| CN | 106236785 A | 12/2016 |
| CN | 106478904 A | 3/2017 |
| CN | 106811998 A | 6/2017 |
| CN | 107173546 A | 9/2017 |
| CN | 107596368 A | 1/2018 |
| CN | 115714187 A | 2/2023 |
| DE | 2446449 A1 | 4/1975 |
| EP | 0217137 A2 | 4/1987 |
| EP | 0587333 A2 | 3/1994 |
| EP | 0597577 A1 | 5/1994 |
| EP | 0945148 A1 | 9/1999 |
| EP | 1008634 A1 | 6/2000 |
| GB | 1284489 A | 8/1972 |
| GB | 1314285 A | 4/1973 |
| GB | 1324087 A | 7/1973 |
| IN | 2012MU01581 A | 1/2014 |
| IN | 2014KO01127 A | 5/2016 |
| IN | 201611026597 A | 3/2018 |
| IN | 201921005566 A | 8/2020 |
| JP | S5156886 A | 5/1976 |
| JP | S51100129 A | 9/1976 |
| JP | H01229014 A | 9/1989 |
| JP | 2003345095 A | 12/2003 |
| JP | 2008274217 A | 11/2008 |
| JP | 2008274218 A | 11/2008 |
| JP | 2008274219 A | 11/2008 |
| JP | 2009016258 A | 1/2009 |
| JP | 2010111781 A | 5/2010 |
| JP | 2011074250 A | 4/2011 |
| JP | 2011207963 A | 10/2011 |
| JP | 2013029832 A | 2/2013 |
| JP | 2013114184 A | 6/2013 |
| JP | 2013237821 A | 11/2013 |
| JP | 2016065115 A | 4/2016 |
| JP | 2016126154 A | 7/2016 |
| JP | 2017058405 A | 3/2017 |
| JP | 2018154752 A | 10/2018 |
| JP | 2018174919 A | 11/2018 |
| JP | 2018203987 A | 12/2018 |
| JP | 2019127444 A | 8/2019 |
| JP | 2020074704 A | 5/2020 |
| JP | 2022057447 A | 4/2022 |
| JP | 2022076360 A | 5/2022 |
| JP | 2022117407 A | 8/2022 |
| KR | 830000972 A | 4/1983 |
| KR | 20020016069 A | 3/2002 |
| KR | 20030078118 A | 10/2003 |
| KR | 20050023239 A | 3/2005 |
| KR | 20080002313 A | 1/2008 |
| KR | 20080008769 A | 1/2008 |
| KR | 100867639 B1 | 11/2008 |
| KR | 20080097787 A | 11/2008 |
| KR | 20090114190 A | 11/2009 |
| KR | 100994148 B1 | 11/2010 |
| KR | 20110043347 A | 4/2011 |
| KR | 20110117758 A | 10/2011 |
| KR | 20110119542 A | 11/2011 |
| KR | 20110135018 A | 12/2011 |
| KR | 20120047345 A | 5/2012 |
| KR | 20120134329 A | 12/2012 |
| KR | 20120134605 A | 12/2012 |
| KR | 20130010708 A | 1/2013 |
| KR | 20130013157 A | 2/2013 |
| KR | 20130027822 A | 3/2013 |
| KR | 20130030907 A | 3/2013 |
| KR | 101312286 B1 | 9/2013 |
| KR | 20140095767 A | 8/2014 |
| KR | 20140105941 A | 9/2014 |
| KR | 101458468 B1 | 11/2014 |
| KR | 20140130579 A | 11/2014 |
| KR | 20150105043 A | 9/2015 |
| KR | 20170076494 A | 7/2017 |
| KR | 101827744 B1 | 2/2018 |
| KR | 20180029147 A | 3/2018 |
| KR | 101850629 B1 | 4/2018 |
| KR | 20180099263 A | 9/2018 |
| KR | 101923028 B1 | 11/2018 |

(56) References Cited

FOREIGN PATENT DOCUMENTS

| | | |
|---|---|---|
| KR | 101943270 B1 | 1/2019 |
| KR | 20190111448 A | 10/2019 |
| KR | 102107332 B1 | 5/2020 |
| KR | 102157964 B1 | 9/2020 |
| KR | 102207353 B1 | 1/2021 |
| KR | 102207354 B1 | 1/2021 |
| KR | 102212503 B1 | 2/2021 |
| KR | 102212504 B1 | 2/2021 |
| KR | 102212505 B1 | 2/2021 |
| KR | 20210122720 A | 10/2021 |
| PL | 440443 A1 | 8/2023 |
| RU | 2582704 C1 | 4/2016 |
| TW | 201204713 A | 2/2012 |
| TW | 201404805 A | 2/2014 |
| WO | 1991013145 A1 | 9/1991 |
| WO | 1998051749 A1 | 11/1998 |
| WO | 2003090780 A1 | 11/2003 |
| WO | 2004096422 A1 | 11/2004 |
| WO | 2007060462 A1 | 5/2007 |
| WO | 2008005543 A2 | 1/2008 |
| WO | 2007078765 A3 | 4/2008 |
| WO | 2008050987 A1 | 5/2008 |
| WO | 2009038340 A1 | 3/2009 |
| WO | 2009088220 A2 | 7/2009 |
| WO | 2009103735 A1 | 8/2009 |
| WO | 2009125987 A2 | 10/2009 |
| WO | 2009127922 A2 | 10/2009 |
| WO | 2009134053 A2 | 11/2009 |
| WO | 2009134076 A2 | 11/2009 |
| WO | 2009141159 A1 | 11/2009 |
| WO | 2009142421 A2 | 11/2009 |
| WO | 2009151295 A2 | 12/2009 |
| WO | 2010008203 A2 | 1/2010 |
| WO | 2010008244 A2 | 1/2010 |
| WO | 2011025167 A2 | 3/2011 |
| WO | 2011025168 A2 | 3/2011 |
| WO | 2011025269 A2 | 3/2011 |
| WO | 2011025270 A2 | 3/2011 |
| WO | 2011025271 A2 | 3/2011 |
| WO | 2011154331 A1 | 12/2011 |
| WO | 2012061719 A3 | 8/2012 |
| WO | 2012101235 A1 | 8/2012 |
| WO | 2012108631 A2 | 8/2012 |
| WO | 2012119997 A1 | 9/2012 |
| WO | 2012138013 A1 | 10/2012 |
| WO | 2012140415 A1 | 10/2012 |
| WO | 2012156058 A1 | 11/2012 |
| WO | 2012156059 A1 | 11/2012 |
| WO | 2012158610 A1 | 11/2012 |
| WO | 2013135853 A1 | 9/2013 |
| WO | 2014109308 A1 | 7/2014 |
| WO | 2015089419 A2 | 6/2015 |
| WO | 2015134787 A2 | 9/2015 |
| WO | WO-2016025747 A1 * | 2/2016 ........... A61K 39/385 |
| WO | 2016164762 A1 | 10/2016 |
| WO | 2016195153 A1 | 12/2016 |
| WO | 2017176040 A1 | 10/2017 |
| WO | 2017184768 A1 | 10/2017 |
| WO | 2017210666 A2 | 12/2017 |
| WO | 2018112555 A1 | 6/2018 |
| WO | 2018190355 A1 | 10/2018 |
| WO | 2019027767 A1 | 2/2019 |
| WO | 2019088662 A1 | 5/2019 |
| WO | 2019126627 A1 | 6/2019 |
| WO | 2019152957 A1 | 8/2019 |
| WO | 2019199133 A1 | 10/2019 |
| WO | 2019220088 A1 | 11/2019 |
| WO | 2020017808 A1 | 1/2020 |
| WO | 2020051507 A1 | 3/2020 |
| WO | 2020080875 A1 | 4/2020 |
| WO | 2020106916 A1 | 5/2020 |
| WO | 2020247382 A1 | 12/2020 |
| WO | 2021007382 A1 | 1/2021 |
| WO | 2021076977 A1 | 4/2021 |
| WO | 2021091188 A1 | 5/2021 |
| WO | 2021125797 A1 | 6/2021 |
| WO | 2021194253 A1 | 9/2021 |
| WO | 2021255262 A1 | 12/2021 |
| WO | 2022091971 A1 | 5/2022 |
| WO | 2022120194 A1 | 6/2022 |
| WO | 2022129097 A2 | 6/2022 |
| WO | 2022139687 A1 | 6/2022 |
| WO | 2022216977 A1 | 10/2022 |
| WO | 2022245307 A1 | 11/2022 |
| WO | 2022266119 A1 | 12/2022 |
| WO | 2023023055 A1 | 2/2023 |
| WO | 2023107574 A2 | 6/2023 |
| WO | 2023193244 A1 | 10/2023 |
| WO | 2023239921 A1 | 12/2023 |
| WO | 2023239922 A1 | 12/2023 |
| WO | WO-2024036356 A1 * | 2/2024 |

OTHER PUBLICATIONS

Convertine et al. "Development of a novel endosomolytic diblock copolymer for siRNA delivery." Journal of controlled release : official journal of the Controlled Release Society vol. 133,3 (2009): 221-9. DOI: 10.1016/j.jconrel.2008.10.004.

Convertine et al. "pH-responsive polymeric micelle carriers for siRNA drugs." Biomacromolecules vol. 11,11 (2010): 2904-11. doi:10.1021/bm100652w.

Dahlman JE, Kauffman KJ, Xing Y, Shaw TE, Mir FF, Dlott CC, Langer R, Anderson DG, Wang ET. Barcoded nanoparticles for high throughput in vivo discovery of targeted therapeutics. Proc Natl Acad Sci U S A. Feb. 21, 2017;114(8):2060-2065. doi: 10.1073/pnas.1620874114. Epub Feb. 6, 2017. PMID: 28167778; PMCID: PMC5338412.

Grimme et al. "Polycation Architecture Affects Complexation and Delivery of Short Antisense Oligonucleotides: Micelleplexes Outperform Polyplexes." Biomacromolecules 2022, 23, 8, 3257-3271, doi: 10.1021/acs.biomac.2c00338.

Haridharan et al. "Exploration of Novel Pyrene Labeled Amphiphilic Block Copolymers: Synthesis Via ATRP, Characterization and Properties." Journal of Macromolecular Science, Part A, vol. 47, No. 9, Jul. 2010, pp. 918-926, doi:10.1080/10601325.2010.501681.

International Search Report and Written Opinion for PCT/US2023/024960, dated Aug. 31, 2023.

Kanth et al. "Recent advances in development of poly (dimethylaminoethyl methacrylate) antimicrobial polymers, European Polymer Journal." vol. 163, 2022, doi: 10.1016/j.eurpolymj.2021.110930.

Lauber et al. "pH-and Thermoresponsive Self-Assembly of Cationic Triblock Copolymers with Controlled Dynamics." Macromolecules 2017, 50, 1, 416-423. doi: 10.1021/acs.macromol.6b02201.

Lucas, Christopher R et al. "DNA Origami Nanostructures Elicit Dose-Dependent Immunogenicity and Are Nontoxic up to High Doses In Vivo." Small (Weinheim an der Bergstrasse, Germany) vol. 18,26 (2022): e2108063. doi: 10.1002/ smll.202108063.

Manganiello et al. "Diblock copolymers with tunable pH transitions for gene delivery." Biomaterials vol. 33,7 (2012): 2301-9. doi: 10.1016/j.biomaterials.2011.11.019.

Muehlebach et al. "Synthesis of Well-Defined Macromonomers and Comb Copolymers from Polymers Made by Atom Transfer Radical Polymerization." J Polym Sci Part A: Polym Chem. vol. 41,21 (2003): 3425-3439, doi: 10.1002/pola. 10940.

Okondo et al., DPP8/9 inhibition induces pro-caspase-1-dependent monocyte and mae::rophage pyroptosis, Nature Chemical Biology, vol. 13, No. 1, pp. 46-53, Jan. 2017.

Okondo et al., Inhibition of Dpp8/9 Activates the Nlrp1 b Inflammasome, Cell Chemical Biology, vol. 25, pp. 262-267, Mar. 15, 2018.

PCT Search Report and Written Opinion for PCT/US2023/024961, mailed Oct. 6, 2023, 14 pages.

Pegg et al. "Solubilisation of oils in aqueous solutions of a random cationic copolymer." Journal of colloid and interface science vol. 502 (2017): 210-218. doi:10.1016/j.jcis.2017.04.093.

(56) References Cited

OTHER PUBLICATIONS

Ponnuswamy, Oligolysine coating, Nature Comm. p. 1 May (Year: 2017).

Samanta, Anirban, and Igor L Medintz. "Nanoparticles and DNA—a powerful and growing functional combination in bionanotechnology." Nanoscale vol. 8, 17 (2016): 9037-95. doi:10.1039/c5nr08465b.

Sprouse et al. "Tuning Cationic Block Copolymer Micelle Size by pH and Ionic Strength." Biomacromolecules 2016, 17, 9, 2849-2859. DOI: 10.1021/acs.biomac.6b00654.

Tapio et al. "The potential of DNA origami to build multifunctional materials." Multifunctional Materials, vol. 3, No. 3, DOI: 10.1088/2399-7532/ab80d5.

The Protein Man, "High Efficiency & Stability Protein Crosslinking with EDC & NHS." The Protein Man's Blog—A Discussion of Protein Research, G-Biosciences, Sep. 26, 2017. Available online at (https://info.gbiosciences.com/blog/2-step-protein-coupling-edc-nhs).

The Protein Man, "Modifying Oligonucleotide 5'-Phosphates By EDC for Improved Coupling." The Protein Man's Blog—A Discussion of Protein Research, G-Biosciences, Aug. 29, 2017. Available online at (https://info.gbiosciences.com/blog/modifying-oligonucleotide-5-phosphates-by-edc-for-improved-coupling).

Yamada, Yoji, Nucleic Acid Drugs-Current Status, Issues and Expectations, Cancers, 2021, 13(19), 5002, 1-19. (Year: 2021).

Zhang, Huan et al. "DNA nanostructures coordinate gene silencing in mature plants." Proceedings of the National Academy of Sciences of the United States of America vol. 116, 15 (2019): 7543-7548. doi: 10.1073/pnas. 1818290116.

U.S. Appl. No. 17/715,784, Patented.

U.S. Appl. No. 18/332,065, Pending.

U.S. Appl. No. 18/332,101, Pending.

U.S. Appl. No. 18/475,879, Pending.

Conesa, Ana et al., "A survey of best practices for RNA-seq data analysis." Genome Biology, Jan. 26, 2016, vol. 17, No. 13; doi:10.1186/s13059-016-0881-8.

PCT Written Opinion for PCT/US2022/023902, mailed Sep. 9, 2022.

PCT Search Report for PCT/US2021/061846, mailed Mar. 30, 2022.

Shimatani et al. 2019. Chapter 22 Targeted Base Editing with CRISPR-Deaminase in Tomato. pp. 297-307 in Qi, Y. [eds] Plant Genome Editing with CRISPR Systems. Methods in Molecular Biology, vol. 1917. Humana Press, New York, NY. (Year: 2019).

Counsell et al. 2017. Lentiviral vectors can be used for full-length dystrophin gene therapy. Scientific Reports 7[79]: epub (Year: 2017).

\* cited by examiner

Library 009

| | ECT | | | | | | | | | CTP | | | | | | | |
|---|---|---|---|---|---|---|---|---|---|---|---|---|---|---|---|---|---|
| | AIBN | | | ACVA | | | AIBN | | | AIBN | | | ACVA | | | |
| | 1 | 5 | 10 | 1 | 5 | 10 | 1 | 5 | 10 | 1 | 5 | 10 | 1 | 5 | 10 | |
| DMAEMA | 31.4 | 46 | 14.2 | 23.9 | 10.4 | 10.2 | | | | | 20.5 | | 29 | | | |
| DPAEMA | 61.3 | 47.7 | 19.1 | 30.5 | 23.9 | 20.6 | 47.2 | | 13.7 | | 16 | | 38.6 | | | |
| | 1.4 | | | | | 0.1 | | 2.6 | 34.4 | | 2.3 | 2 | | | | |
| MMA | 5 | 4 | 2.6 | 1.9 | | 2.2 | 7.4 | 1.3 | | | 15.4 | | | | | |
| | 9.1 | 5 | 7.8 | 5.8 | 6.3 | | 9.4 | 9.1 | 3 | 3.7 | 19.1 | 11.5 | | | | |
| | 5.4 | 6.6 | 13.4 | 9 | 5.5 | 18.3 | 9.2 | 23 | 16.3 | 7.7 | 10.8 | 17.5 | | | | |
| BMA | 20 | 3.9 | 8.3 | 17 | 0 | 2 | 23.8 | 5.9 | 5.6 | 23 | 1.3 | | | | | |
| | 11.5 | 3.3 | 17.1 | 17.5 | 27.2 | 3.4 | 22.9 | | 4.4 | 13.5 | 15.5 | 0.9 | | | | |

POLYMER NANOPARTICLE AND DNA NANOSTRUCTURE COMPOSITIONS AND METHODS FOR NON-VIRAL DELIVERY

CROSS-REFERENCE TO RELATED APPLICATIONS

This application is a continuation of U.S. patent application Ser. No. 17/542,055, filed Dec. 3, 2021, which claims priority under 35 U.S.C. § 119(c) to U.S. Provisional Application Ser. No. 63/121,202 filed on Dec. 3, 2020, the entire disclosure of which is incorporated herein by reference.

FIELD OF THE DISCLOSURE

The invention relates to polymer nanoparticle and DNA nanostructure delivery compositions for non-viral delivery, and methods therefor. More particularly, the invention relates to polymer nanoparticle delivery compositions, such as reversible addition-fragmentation chain transfer (RAFT) polymer compositions, and DNA nanostructure delivery compositions, such as DNA origami compositions, for the delivery, for example, of more than one payload, or for the delivery of a nucleic acid construct payload of 3 kB or more, and methods therefor.

BACKGROUND AND SUMMARY

Genetic medicines (including gene therapy, gene silencing, splicing regulators, and nuclease based gene editors) are poised to produce revolutionary treatments, including vaccines, infectious disease treatments, antimicrobial treatments, antiviral treatments, and most notably, genetic disease treatments. However, the in vivo delivery of these genetic medicine payloads to the specific tissues and cells that need to be treated, while avoiding tissues and cells that can reduce the efficacy or safety of the genetic medicine, poses a significant challenge. Additional challenges include the ability to deliver large genetic payloads or multiple payloads. Adeno-associated viruses (AAVs) are the most widely used tool for genetic medicine delivery, but AAVs are not able to deliver large genetic payloads or multiple payloads (such as the clustered regularly interspaced short palindromic repeats (CRISPR)/Cas9 system), and they sometimes trigger unwanted immune responses, including the generation of anti-AAV antibodies, a cell mediated response. Some of the immune responses caused by AAV in patients are potentially fatal immune responses.

Therapeutics based on the CRISPR/Cas9 system have an exceptional potential to treat a number of genetic diseases due to the capability of this system for precise and programmable gene editing. Gene editing and repair using the CRISPR/Cas9 system has two main mechanisms, including non-homologous end joining (NHEJ) which repairs the site of cut by inducing random indel mutation, and homology-directed repair (HDR), which repairs the cut site based on a pre-existing template. Because a pre-designed template can be used for HDR-directed repair, therapies based on this mechanism can be tailored to cure a large number of different genetic diseases. However, the main challenge is that HDR repair requires the delivery of CRISPR/Cas9, small guide RNA (sgRNA) and a donor DNA strand at the same time to a particular location. This requirement becomes particularly limiting for in vivo applications because ensuring co-delivery of multiple large molecules to the same targeted location is currently not feasible. For example, the Cas9 enzyme sequence and guide RNA complex is too large to fit into AAVs.

Thus, there is a need for effective non-viral delivery systems, including gene delivery systems. The current state-of-the-art non-viral gene delivery systems, such as liposomes, have many drawbacks such as poor biocompatibility and the inability to easily engineer or functionalize them. Additional concerns are that such non-viral gene delivery systems are easily degraded by various enzymes as they pass through intracellular or intercellular compartments, and these systems have not been able to package multiple large payloads.

The inventors have designed polymer nanoparticle (e.g., RAFT polymer) and DNA nanostructure delivery compositions (e.g., DNA origami nanostructures). These compositions have the advantage of being biocompatible, non-toxic, and can be programmed in many ways. For example, the polymer nanoparticle and DNA nanostructure delivery compositions can be programmed to have functional groups that enable them to evade early degradation, that enable them to evade immune responses, and that enable intracellular imaging and targeted and controlled delivery of therapeutic genes. Thus, these non-viral delivery compositions can enhance the stability, safety, and/or efficacy of genetic medicine payloads by providing immune evasion, tissue-directed intracellular delivery, and the ability to deliver large genetic payloads or multiple payloads.

The following clauses, and combinations thereof, provide various additional illustrative aspects of the invention described herein. The various embodiments described in any other section of this patent application, including the section titled "DETAILED DESCRIPTION OF ILLUSTRATIVE EMBODIMENTS" and the "EXAMPLES" are applicable to any of the following embodiments of the invention described in the numbered clauses below.

1. A DNA nanostructure delivery composition comprising: i) a single stranded DNA scaffold and ii) one or more oligonucleotides that bind through complementary base pairing with a segment of the DNA scaffold, wherein the one or more oligonucleotides cause the DNA scaffold to fold, and wherein the composition comprises more than one payload for delivery or a nucleic acid construct payload of 3 kB or more.

2. The composition of clause 1 wherein the more than one payload comprises nucleic acids.

3. The composition of clause 2 wherein the nucleic acids comprise DNA or RNA.

4. The composition of clause 2 wherein the nucleic acids comprise a ribonucleoprotein.

5. The composition of clause 2 wherein the payload nucleic acids are used for homology directed repair or as transposable elements.

6. The composition of clause 2 wherein the payload nucleic acids comprise a short guide RNA (sgRNA) and a donor DNA strand.

7. The composition of clause 6 wherein the sgRNA is used for targeting an enzyme to a specific genomic sequence.

8. The composition of clause 1 wherein the payloads comprise a CRISPR associated enzyme.

9. The composition of clause 7 wherein the targeted enzyme is a CRISPR associated enzyme.

10. The composition of clause 1 wherein the payloads comprise a CRISPR associated enzyme, an sgRNA, and a donor DNA strand.

11. The composition of clause 1 wherein the payloads comprise CRISPR/Cas9.

12. The composition of clause 1 wherein the payloads comprise CRISPR/Cas9, an sgRNA, and a donor DNA strand.

13. The composition of clause 1 wherein the payload comprises CRISPR/Cas9 and Cas9 is fused with a deaminase.

14. The composition of clause 1 wherein the payloads comprise a coding sequence for Cas9, an sgRNA, and a donor DNA strand in the form of a plasmid.

15. The composition of clause 1 wherein the payloads consist of one molecule each of CRISPR/Cas9, an sgRNA, and a donor DNA strand.

16. The composition of clause 1 wherein the nucleic acid construct payload of 3 kB or more comprises a CAR-T DNA construct.

17. The composition of clause 1 wherein the payloads comprise an antisense oligonucleotide.

18. The composition of clause 1 wherein the nucleic acid construct payload is of a size selected from the group consisting of 3 kB or more, 3.5 kB or more, 4 kB or more, 4.5 kB or more, 5 kB or more, 5.5 kB or more, 6 kB or more, 6.5 kB or more, 7 kB or more, 7.5 kB or more, 8 kB or more, and 8.5 kB or more.

19. The composition of clause 1 wherein the payloads comprise a reverse transcriptase.

20. The composition of clause 1 wherein the DNA scaffold and the one or more oligonucleotides comprise M13 bacteriophage DNA.

21. The composition of clause 2 wherein the one or more oligonucleotides comprise overhangs that bind through complementary base paring with the payload nucleic acids.

22. The composition of clause 1 wherein the DNA scaffold has an aspect ratio of about 2.

23. The composition of clause 21 wherein the overhangs are located within a cavity within the DNA scaffold.

24. The composition of clause 23 wherein the cavity is covered by a lid and a hinge allowing the payloads to be completely enclosed within the cavity when the lid is shut.

25. The composition of clause 24 wherein the lid comprises oligonucleotide strands that bind through complementary base pairing with other oligonucleotide strands attached to the DNA scaffold when the lid is in the closed position.

26. The composition of clause 1 further comprising a pharmaceutically acceptable carrier.

27. The composition of clause 26 wherein the pharmaceutically acceptable carrier is for parenteral administration or topical administration.

28. The composition of clause 1 wherein the DNA nanostructure is coated with one or more polymers.

29. The composition of clause 28 wherein the one or more polymers comprise polyethylene glycol.

30. The composition of clause 28 wherein the one or more polymers comprise polyethylene glycol poly-L-lysine.

31. The composition of clause 28 wherein the one or more polymers comprise polyethylenimine.

32. The composition of clause 28 wherein the one or more polymers comprise polyethylene glycol poly-L-lysine and polyethylenimine.

33. The composition of clause 1 wherein the DNA nanostructure further comprises a targeting component for targeting to cells.

34. The composition of clause 33 wherein the targeting component is a nucleotide that has a three-dimensional structure capable of binding a target cell receptor.

35. The composition of clause 34 wherein the nucleotide that binds to the target cell receptor binds in conjunction with a peptide aptamer.

36. The composition of clause 34 wherein the nucleotide is an RNA that forms a 'stem-and-loop' structure.

37. A method for gene therapy comprising administering to a patient a DNA nanostructure delivery composition comprising: i) a single stranded DNA scaffold and ii) one or more oligonucleotides that bind through complementary base pairing with a segment of the DNA scaffold, wherein the one or more oligonucleotides cause the DNA scaffold to fold, and wherein the composition comprises more than one payload for delivery or a nucleic acid construct payload of 3 kB or more.

38. The method of clause 37 wherein the more than one payload comprises nucleic acids.

39. The method of clause 38 wherein the nucleic acids comprise DNA or RNA.

40. The method of clause 38 wherein the nucleic acids comprise a ribonucleoprotein.

41. The method of clause 38 wherein the payload nucleic acids are used for homology directed repair or as transposable elements.

42. The method of clause 38 wherein the payload nucleic acids comprise a short guide RNA (sgRNA) and a donor DNA strand.

43. The method of clause 42 wherein the sgRNA is used for targeting an enzyme to a specific genomic sequence.

44. The method of clause 37 wherein the payloads comprise a CRISPR associated enzyme.

45. The method of clause 43 wherein the targeted enzyme is a CRISPR associated enzyme.

46. The method of clause 37 wherein the payloads comprise a CRISPR associated enzyme, an sgRNA, and a donor DNA strand.

47. The method of clause 37 wherein the payloads comprise CRISPR/Cas9.

48. The method of clause 37 wherein the payloads comprise CRISPR/Cas9, an sgRNA, and a donor DNA strand.

49. The method of clause 37 wherein the payload comprises CRISPR/Cas9 and Cas9 is fused with a deaminase.

50. The method of clause 37 wherein the payloads comprise a coding sequence for Cas9, an sgRNA, and a donor DNA strand in the form of a plasmid.

51. The method of clause 37 wherein the payloads consist of one molecule each of CRISPR/Cas9, an sgRNA, and a donor DNA strand.

52. The method of clause 37 wherein the nucleic acid construct payload of 3 kB or more comprises a CAR-T DNA construct.

53. The method of clause 37 wherein the payloads comprise an antisense oligonucleotide.

54. The method of clause 37 wherein the nucleic acid construct payload is of a size selected from the group consisting of 3 kB or more, 3.5 kB or more, 4 kB or more, 4.5 kB or more, 5 kB or more, 5.5 kB or more, 6 kB or more, 6.5 kB or more, 7 kB or more, 7.5 kB or more, 8 kB or more, and 8.5 kB or more.

55. The method of clause 37 wherein the payloads comprise a reverse transcriptase.

56. The method of clause 37 wherein the DNA scaffold and the one or more oligonucleotides comprise M13 bacteriophage DNA.

57. The method of clause 38 wherein the one or more oligonucleotides comprise overhangs that bind through complementary base paring with the payload nucleic acids.

58. The method of clause 37 wherein the DNA scaffold has an aspect ratio of about 2.

59. The method of clause 57 wherein the overhangs are located within a cavity within the DNA scaffold.

60. The method of clause 59 wherein the cavity is covered by a lid and a hinge allowing the payloads to be completely enclosed within the cavity when the lid is shut.

61. The method of clause 60 wherein the lid comprises oligonucleotide strands that bind through complementary base pairing with other oligonucleotide strands attached to the DNA scaffold when the lid is in the closed position.

62. The method of clause 37 further comprising administering a pharmaceutically acceptable carrier to the patient.

63. The method of clause 62 wherein the pharmaceutically acceptable carrier is for parenteral administration or topical administration.

64. The method of clause 37 wherein the DNA nanostructure is coated with one or more polymers.

65. The method of clause 64 wherein the one or more polymers comprise polyethylene glycol.

66. The method of clause 64 wherein the one or more polymers comprise polyethylene glycol poly-L-lysine.

67. The method of clause 64 wherein the one or more polymers comprise polyethylenimine.

68. The method of clause 64 wherein the one or more polymers comprise polyethylene glycol poly-L-lysine and polyethylenimine.

69. The method of clause 37 wherein the DNA nanostructure further comprises a targeting component for targeting to cells of the patient.

70. The method of clause 69 wherein the targeting component is a nucleotide that has a three-dimensional structure capable of binding a target cell receptor.

71. The method of clause 70 wherein the nucleotide that binds to the target cell receptor binds in conjunction with a peptide aptamer.

72. The method of clause 70 wherein the nucleotide is an RNA that forms a 'stem-and-loop' structure.

73. The method of clause 37 wherein the patient has a disease or a disorder selected from the group consisting of cancer, a muscular disorder, a pulmonary disorder, a skin disorder, a neurological disease, neurofibromatosis 1, and a hemoglobinopathy.

74 The method of clause 73 wherein the cancer is selected from the group consisting of lung cancer, bone cancer, pancreatic cancer, skin cancer, uterine cancer, ovarian cancer, endometrial cancer, rectal cancer, stomach cancer, colon cancer, breast cancer, cancer of the esophagus, cancer of the endocrine system, prostate cancer, leukemia, lymphoma, mesothelioma, cancer of the bladder, cancer of the kidney, neoplasms of the central nervous system, brain cancer, and adenocarcinoma.

75. The method of clause 73 wherein the skin disorder is a *Staphlococcus aureus* infection.

76. The method of clause 73 wherein the muscular disorder is muscular dystrophy.

77. The method of clause 37 wherein the DNA nanostructure delivery composition is not cytotoxic to the cells of the patient.

78. A method for targeting a DNA nanostructure delivery composition to cells of a patient, comprising administering to the patient: i) a single stranded DNA scaffold and ii) one or more oligonucleotides that bind through complementary base pairing with a segment of the DNA scaffold, wherein the one or more oligonucleotides cause the DNA scaffold to fold, wherein the composition comprises more than one payload for delivery or a nucleic acid construct payload of 3 kB or more, and wherein the DNA nanostructure comprises a targeting component for targeting to the cells of the patient.

79. The method of clause 78 wherein the more than one payload comprises nucleic acids.

80. The method of clause 79 wherein the nucleic acids comprise DNA or RNA.

81. The method of clause 79 wherein the nucleic acids comprise a ribonucleoprotein.

82. The method of clause 79 wherein the payload nucleic acids are used for homology directed repair or as transposable elements.

83. The method of clause 79 wherein the payload nucleic acids comprise a short guide RNA (sgRNA) and a donor DNA strand.

84. The method of clause 83 wherein the sgRNA is used for targeting an enzyme to a specific genomic sequence.

85. The method of clause 78 wherein the payloads comprise a CRISPR associated enzyme.

86. The method of clause 84 wherein the targeted enzyme is a CRISPR associated enzyme.

87. The method of clause 78 wherein the payloads comprise a CRISPR associated enzyme, an sgRNA, and a donor DNA strand.

88. The method of clause 78 wherein the payloads comprise CRISPR/Cas9.

89. The method of clause 78 wherein the payloads comprise CRISPR/Cas9, an sgRNA, and a donor DNA strand.

90. The method of clause 78 wherein the payload comprises CRISPR/Cas9 and Cas9 is fused with a deaminase.

91. The method of clause 78 wherein the payloads comprise a coding sequence for Cas9, an sgRNA, and a donor DNA strand in the form of a plasmid.

92. The method of clause 78 wherein the payloads consist of one molecule each of CRISPR/Cas9, an sgRNA, and a donor DNA strand.

93. The method of clause 78 wherein the nucleic acid construct payload of 3 kB or more comprises a CAR-T DNA construct.

94. The method of clause 78 wherein the payloads comprise an antisense oligonucleotide.

95. The method of clause 78 wherein the nucleic acid construct payload is of a size selected from the group consisting of 3 kB or more, 3.5 kB or more, 4 kB or more, 4.5 kB or more, 5 kB or more, 5.5 kB or more, 6 kB or more, 6.5 kB or more, 7 KB or more, 7.5 kB or more, 8 kB or more, and 8.5 kB or more.

96. The method of clause 78 wherein the payloads comprise a reverse transcriptase.

97. The method of clause 78 wherein the DNA scaffold and the one or more oligonucleotides comprise M13 bacteriophage DNA.

98. The method of clause 79 wherein the one or more oligonucleotides comprise overhangs that bind through complementary base paring with the payload nucleic acids.

99. The method of clause 78 wherein the DNA scaffold has an aspect ratio of about 2.

100. The method of clause 98 wherein the overhangs are located within a cavity within the DNA scaffold.

101. The method of clause 100 wherein the cavity is covered by a lid and a hinge allowing the payloads to be completely enclosed within the cavity when the lid is shut.

102. The method of clause 101 wherein the lid comprises oligonucleotide strands that bind through complementary base pairing with other oligonucleotide strands attached to the DNA scaffold when the lid is in the closed position.

103. The method of clause 78 wherein the DNA nanostructure is coated with one or more polymers.

104. The method of clause 103 wherein the one or more polymers comprise polyethylene glycol.

105. The method of clause 103 wherein the one or more polymers comprise polyethylene gycol poly-L-lysine.

106. The method of clause 103 wherein the one or more polymers comprise polyethylenimine.

107. The method of clause 103 wherein the one or more polymers comprise polyethylene glycol poly-L-lysine and polyethylenimine.

108. The method of clause 78 wherein the targeting component is a nucleotide that has a three-dimensional structure capable of binding a target cell receptor.

109. The method of clause 108 wherein the nucleotide that binds to the target cell receptor binds in conjunction with a peptide aptamer.

110. The method of clause 108 wherein the nucleotide is an RNA that forms a 'stem-and-loop' structure.

111. The method of clause 100 wherein the cavity is covered by a lid and a hinge and wherein the lid opens when the DNA nanostructure delivery composition contacts a DNA, an RNA, or an antigen associated with the cells of the patient.

112. A method comprising:
synthesizing a diverse set of non-viral gene delivery compositions, wherein each non-viral gene delivery composition differs from each other non-viral gene delivery composition of the diverse set with respect to at least one of a set of composition characteristics,
simultaneously testing one or more quality attributes of each of the non-viral gene delivery composition of the diverse set, and
creating, using results of the testing, a predictive model that correlates the composition characteristics with the quality attributes.

113. The method of clause 112, wherein the composition characteristics comprise one or more of molecular weight, degree of branching, number of ionizable groups, core-to-corona molecular weight ratio, hydrophilicity, hydrophobicity, propensity for aggregation, size, pKa, logP, and surface charge.

114. The method of clause 112 or clause 113, wherein the quality attributes comprise one or more of cytotoxicity, immunogenicity, transfection efficiency, zeta potential, size, pKa, logP, and loading efficiency.

115. The method of any one of clauses 112-114, wherein the diverse set comprises hundreds of non-viral gene delivery compositions.

116. The method of clause 115, wherein the diverse set comprises thousands of non-viral gene delivery compositions.

117. The method of any one of clauses 112-116, wherein each of the non-viral gene delivery compositions of the diverse set is a DNA nanostructure delivery composition according to one of clauses 1-36.

118. A RAFT block copolymer comprising
a. a first terminus comprising a first capping unit derived from a first chain transfer agent in a RAFT copolymerization process;
b. a first block prepared from one or more monomer units covalently attached to the first reactive functional unit, and having a molecular weight (Mn) in the range of about 20 kDa to about 40 kDa and a degree of polymerization in the range of about 300 to about 400;
c. a second block prepared from one or more monomer units covalently attached to the first block, and having a molecular weight (Mn) in the range of about 5 kDa to about 20 kDa and a degree of polymerization in the range of about 400 to about 500; and
d. a second terminus comprising a second capping unit derived from a second chain transfer agent;
wherein the RAFT block copolymer has one or more of an overall molecular weight (Mn) in the range of about 25 kDa to about 60 kDa, and overall degree of polymerization in the range of about 700 to about 900, a target size in the range of about of about 10 to about 60 nm, and a maximum corona-to-core ratio (CCR) of about 1.5 to about 3.5.

119. The RAFT block copolymer of clause 118, wherein the first block is prepared from one or more monomer units selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

120. The RAFT block copolymer of clause 118 or 119, wherein the first block is prepared from one of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl) methacrylate, or methyl methacrylate.

121. The RAFT block copolymer of any one of clause 118 to 120, wherein the second block is prepared from one or more monomer units selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxycthyl)methacrylate, and methyl methacrylate.

122. The RAFT block copolymer of any one of clauses 118 to 121, wherein the second block is a random copolymer prepared from two different monomer units independently selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

123. The RAFT block copolymer of any one of clauses 118 to 121, wherein the second block is a random copolymer prepared from three different monomer units independently selected from the group consisting of 2-dimethylaminocthyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

124. The RAFT block copolymer of any one of clauses 118 to 123, wherein the second block is a random copolymer prepared from 2-dimethylaminoethyl acrylate, butyl methacrylate, and propyl acrylic acid; or 2-dimethylaminoethyl acrylate and butyl methacrylate; or 2-dimethylaminoethyl acrylate, butyl methacrylate, and ethyl acrylic acid.

125. The RAFT block copolymer of any one of clauses 118 to 124, wherein each chain transfer agent is independently selected from the group consisting of bis(carboxymethyl)trithiocarbonate, bis(2-amino-2-oxoethyl) trithiocarbonate, bis[4-(2-hydroxyethoxycarbonyl)benzyl] trithiocarbonate, 4-cyano-4-(ethylsulfanylthiocarbonyl) sulfanylvpentanoic acid, 4-cyano-4-((phenylcarbonothioyl) thio)pentanoic acid, and 4-cyano-4-[(dodecylsulfanylthiocarbonyl)sulfanyl] pentanoic acid.

126. The RAFT block copolymer of any one of clauses 118 to 125, wherein the first capping unit is of the formula

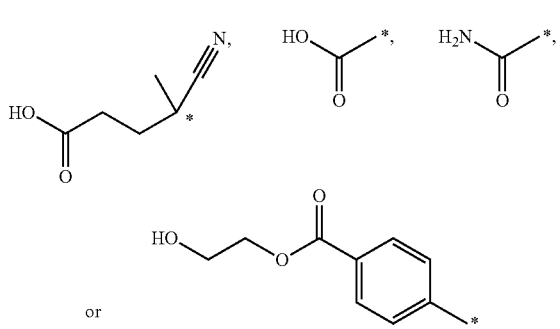

wherein * represents a point of covalent attachment to the first block.

127. The RAFT block copolymer of any one of clauses 118 to 126, wherein the second capping unit is of the formula

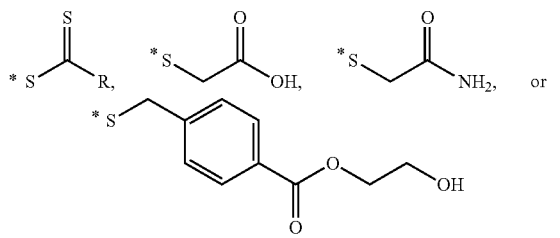

wherein * represents a point of covalent attachment to the second block, and R is —SC$_2$-C$_{12}$ alkyl or C$_6$H$_5$, 128. A method of preparing a RAFT block copolymer comprising:
 i. contacting a first chain transfer agent, a first initiator and one or more monomer units to provide a first block;
 ii. contacting a second chain transfer agent, a second initiator and one or more monomer units to provide a second block
 iii. contacting the first block and the second block under conditions capable of coupling the blocks to provide the RAFT block copolymer.

129. The method of clause 128, wherein the first chain transfer agent is a diamino or dihydroxy chain transfer agent, and the second chain transfer agent is a dicarboxylic acid chain transfer agent.

130. The method of clause 128 or 129, wherein the first chain transfer agent is bis(2-amino-2-oxoethyl) trithiocarbonate or bis[4-(2-hydroxyethoxycarbonyl)benzyl] trithiocarbonate, and the second chain transfer agent is bis(carboxymethyl)trithiocarbonate.

131. The method of clause 128, wherein the first chain transfer agent is a dicarboxylic acid chain transfer agent, and the second chain transfer agent is a diamino or dihydroxy chain transfer agent.

132. The method of clause 128 or 131, wherein the first chain transfer agent is bis(carboxymethyl)trithiocarbonate, and the second chain transfer agent is bis(2-amino-2-oxoethyl) trithiocarbonate or bis[4-(2-hydroxyethoxycarbonyl)benzyl] trithiocarbonate.

133. The method of any one of clauses 128 to 132, wherein the step (iii) is carried out under conditions capable of promoting amidation or esterification.

134. The method of any one of clauses 128 to 133, wherein the one or more monomer units in step (i) are independently selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

135. The method of any one of clauses 128 to 134, wherein the one or more monomer units in step (i) is one of 2-dimethylaminoethyl acrylate. 2-(diethylamino) ethyl methacrylate, 2-(diisopropylamino) ethyl methacrylate, butyl methacrylate, ethyl acrylic acid, propyl acrylic acid, (hydroxyethyl)methacrylate, or methyl methacrylate.

136. The method of any one of clauses 128 to 135, wherein the one or more monomer units in step (ii) are independently selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

137. The method of any one of clauses 128 to 136, wherein the one or more monomer units in step (ii) are two different monomer units independently selected from the group consisting methacrylate, butyl methacrylate, ethyl acrylic acid, propyl acrylic acid, (hydroxyethyl)methacrylate, and methyl methacrylate.

138. The method of any one of clauses 128 to 136, wherein the one or more monomer units in step (ii) are three different monomer units independently selected from the group consisting of 2-dimethylaminoethyl acrylate. 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

139. The method of any one of clauses 128 to 138, wherein the one or more monomer units in step (ii) are 2-dimethylaminoethyl acrylate, butyl methacrylate, and propyl acrylic acid; or 2-dimethylaminocthyl acrylate and butyl methacrylate; or 2-dimethylaminoethyl acrylate, butyl methacrylate, and ethyl acrylic acid.

140. The method of any one of clauses 128 to 139, wherein the RAFT block copolymer has one or more of an overall molecular weight (Mn) in the range of about 25 kDa to about 60 kDa, and overall degree of polymerization in the range of about 700 to about 900, a target size in the range of about of about 10 to about 60 nm, and a maximum corona-to-core ratio (CCR) of about 1.5 to about 3.5.

141. A method of preparing a library of RAFT block copolymers comprising:
 i. providing an array of reaction mixtures in a multiwell plate, wherein each well comprises a mixture of a first chain transfer agent, a first initiator, one or more monomer units, and optionally a solvent or solvent mixture;
 ii. reacting the mixture in each well under conditions that promote RAFT copolymerization to provide a series of first block copolymers in the wells of the multiwell plate;
 iii. quenching the reactions in the wells of the multiwell plate;
 iv. purifying the first block copolymer in each well of the multiwell plate;
 v. optionally characterizing the first block copolymer in each well of the multiwell plate;
 vi. optionally purifying the first block copolymer in each well of the multiwell plate;
 vii. contacting to the first block copolymer in each well of the multiwell plate with a second array of reaction mixtures comprising a second chain transfer agent, a second initiator, and one or more monomer units, and optionally a solvent or solvent mixture;

viii. reacting the components of step (vii) under conditions that promote RAFT copolymerization to provide a series of RAFT block copolymers in the wells of the multiwell plate;

ix. quenching the reactions in the wells of the multiwell plate;

x. purifying the RAFT block copolymer in each well of the multiwell plate; and xi. optionally characterizing the RAFT block copolymer in each well of the multiwell plate.

142. The method of clause 142, wherein the one or more monomer units in step (i) are independently selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

143. The method of clause 141 or 142, wherein the one or more monomer units in step (i) is one of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, or methyl methacrylate.

144. The method of any one of clauses 141 to 143, wherein the one or more monomer units in step (vii) are independently selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

145. The method of any one of clauses 141 to 144, wherein the one or more monomer units in step (vii) are two different monomer units independently selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

146. The method of any one of clauses 141 to 145, wherein the one or more monomer units in step (vii) are three different monomer units independently selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

147. The method of any one of clauses 141 to 146, wherein the one or more monomer units in step (vii) are 2-dimethylaminoethyl acrylate, butyl methacrylate, and propyl acrylic acid; or 2-dimethylaminoethyl acrylate and butyl methacrylate; or 2-dimethylaminoethyl acrylate, butyl methacrylate, and ethyl acrylic acid.

148. The method of any one of clauses 141 to 147, wherein the first and second chain transfer agent are the same or different.

149. The method of any one of clauses 141 to 148, wherein the first and second chain transfer agent are the same.

150. The method of any one of clauses 141 to 148, wherein the first and second chain transfer agent are different.

151. The method of any one of clauses 141 to 150, wherein the first and second chain transfer are each independently selected from the group consisting of bis(carboxymethyl)trithiocarbonate, bis(2-amino-2-oxoethyl) trithiocarbonate, bis[4-(2-hydroxyethoxycarbonyl)benzyl] trithiocarbonate, 4-cyano-4-(ethylsulfanylthiocarbonyl) sulfanylypentanoic acid, 4-cyano-4-((phenylcarbonothioyl)thio)pentanoic acid, and 4-cyano-4-[(dodecylsulfanylthiocarbonyl)sulfanyl] pentanoic acid.

152. The method of any one of clauses 141 to 151, wherein the solvent or mixture of solvents provided in steps (i) and (vii) is one or more of dimethylformamide, dimethylsulfoxide, isopropyl alcohol, hexanes, 1,4-dioxane, and tetrahydrofuran.

153. The method of any one of clauses 141 to 152, wherein the steps (ii) and (viii) are each carried out under an atmosphere of saturated solvent of steps (i) and (vii).

154. The method of any one of clauses 141 to 153, wherein characterizing in steps (v) and (xi) are technique is high throughput zeta potential measurement using a multiwell plate dynamic light scattering device to measure changes in the interaction parameter or the second virial coefficient with respect to concentration or ionic strength or high throughput measurement of the differential refractive index of the polymer.

155. The method of any one of clauses 141 to 154, wherein the quenching steps (iii) and (ix) are carried out by exposure of the multiwell plate to oxygen.

156. The method of any one of clauses 141 to 155, wherein the purifying steps (iv) and (x) are carried out via filtration, diafiltration, or dialysis in a multiwell format.

157. A composition comprising a RAFT block copolymer according to any one of clauses 118 to 127 or a RAFT block copolymer prepared according to the method of any one of clauses 128 to 156.

158. A RAFT block copolymer conjugate comprising a RAFT block copolymer according to any one of clauses 118 to 127 or a RAFT block copolymer prepared according to the method of any one of clauses 128 to 156, and further comprising a biomolecule, drug, or label covalently attached to the RAFT block copolymer through a functional group on one of the first or second chain transfer agents that is incorporated into the RAFT block copolymer.

159. The RAFT block copolymer conjugate of clause 158, wherein the biomolecule and the RAFT block copolymer are covalently attached via an amide bond or an ester bond.

160. A method of preparing a RAFT block copolymer conjugate comprising a RAFT block copolymer according to any one of clauses 118 to 127 or a RAFT block copolymer prepared according to the method of any one of clauses 128 to 156 and a biomolecule, drug, or label, wherein the RAFT block copolymer and the biomolecule, drug, or label are covalently attached through a functional group on one of the first or second chain transfer agents that is incorporated into the RAFT block copolymer.

161. The method of clause 160, wherein a covalent bond is formed between the RAFT block copolymer and the biomolecule, drug, or label via an EDC-NHS reaction of a functional group on one of the first or second chain transfer agents that is incorporated into the RAFT block copolymer.

162. The method of clause 160 or 161, wherein the functional group a carboxylate group that is reacted with a primary amine on the biomolecule, drug, or label via EDC-NHS chemistry.

163. The method of any one of clauses 160 to 162, wherein the RAFT block copolymer and the biomolecule, drug, or label are covalently attached via an amide bond.

164. The method of any one of clauses 160 to 163, wherein the first or second chain transfer agent is 2-(dodecylthiocarbonothioylthio)-2-methylpropionic acid or 4-cyano-4-(ethylsulfanylthiocarbonyl) sulfanylvpentanoic acid.

165. The method of any one of clauses 160 to 164, wherein the biomolecule is a protein.

166. The method of any one of clauses 160 to 164, wherein the label is avidin or biotin.

167. A RAFT block copolymer complex comprising a RAFT block copolymer according to any one of clauses 118 to 127 or a RAFT block copolymer prepared according to the method of any one of clauses 128 to 156, and further comprising a payload complexed to the RAFT block copolymer through electrostatic interaction.

168. The RAFT block copolymer complex of clause 167 wherein the payload comprises nucleic acids.

169. The RAFT block copolymer complex of clause 168 wherein the nucleic acids comprise DNA or RNA.

170. The RAFT block copolymer complex of clause 168 wherein the nucleic acids comprise a ribonucleoprotein.

171. The RAFT block copolymer complex of clause 168 wherein the payload nucleic acids are used for homology directed repair or as transposable elements.

172. The RAFT block copolymer complex of clause 168 wherein the payload nucleic acids comprise a short guide RNA (sgRNA) and a donor DNA strand.

173. The RAFT block copolymer complex of clause 172 wherein the sgRNA is used for targeting an enzyme to a specific genomic sequence.

174. The RAFT block copolymer complex of clause 167 wherein the payload comprises a CRISPR associated enzyme.

175. The RAFT block copolymer complex of clause 173 wherein the targeted enzyme is a CRISPR associated enzyme.

176. The RAFT block copolymer complex of clause 167 wherein the payload comprises a CRISPR associated enzyme, an sgRNA, and a donor DNA strand.

177. The RAFT block copolymer complex of clause 167 wherein the payload comprises CRISPR/Cas9.

178. The RAFT block copolymer complex of clause 167 wherein the payload comprises CRISPR/Cas9, an sgRNA, and a donor DNA strand.

179. The RAFT block copolymer complex of clause 167 wherein the payload comprises CRISPR/Cas9 and Cas9 is fused with a deaminase.

180. The RAFT block copolymer complex of clause 167 wherein the payload comprises a coding sequence for Cas9, an sgRNA, and a donor DNA strand in the form of a plasmid.

181. The RAFT block copolymer complex of clause 167 wherein the payload consists of one molecule each of CRISPR/Cas9, an sgRNA, and a donor DNA strand.

182. The RAFT block copolymer complex of clause 167 wherein the payload comprises a CAR-T DNA construct.

183. The RAFT block copolymer complex of clause 167 wherein the payload comprises an antisense oligonucleotide.

184. The RAFT block copolymer complex of clause 167 wherein the payload is a nucleic acid and the nucleic acid payload is of a size selected from the group consisting of 3 kB or more, 3.5 KB or more, 4 kB or more, 4.5 kB or more, 5 kB or more, 5.5 kB or more, 6 kB or more, 6.5 kB or more, 7 KB or more, 7.5 kB or more, 8 kB or more, and 8.5 kB or more.

185. The RAFT block copolymer complex of clause 167 wherein the payload comprises a reverse transcriptase.

186. The RAFT block copolymer complex of clause 167 further comprising a pharmaceutically acceptable carrier.

187. The RAFT block copolymer complex of clause 186 wherein the pharmaceutically acceptable carrier is for parenteral administration or topical administration.

188. The RAFT block copolymer complex of clause 167 further comprising a targeting component for targeting to cells.

189. A method for gene therapy comprising administering to a patient a RAFT block copolymer of any one of clauses 167 to 188.

190. A method for targeting a polymer nanoparticle composition to cells of a patient, comprising administering to the patient a RAFT block copolymer of any one of clauses 167 to 188.

191. The method of any one of clauses 112-116, wherein each of the non-viral gene delivery compositions of the diverse set is a RAFT block copolymer according to one of clauses 118-127.

BRIEF DESCRIPTION OF THE DRAWINGS

Figure 8B:
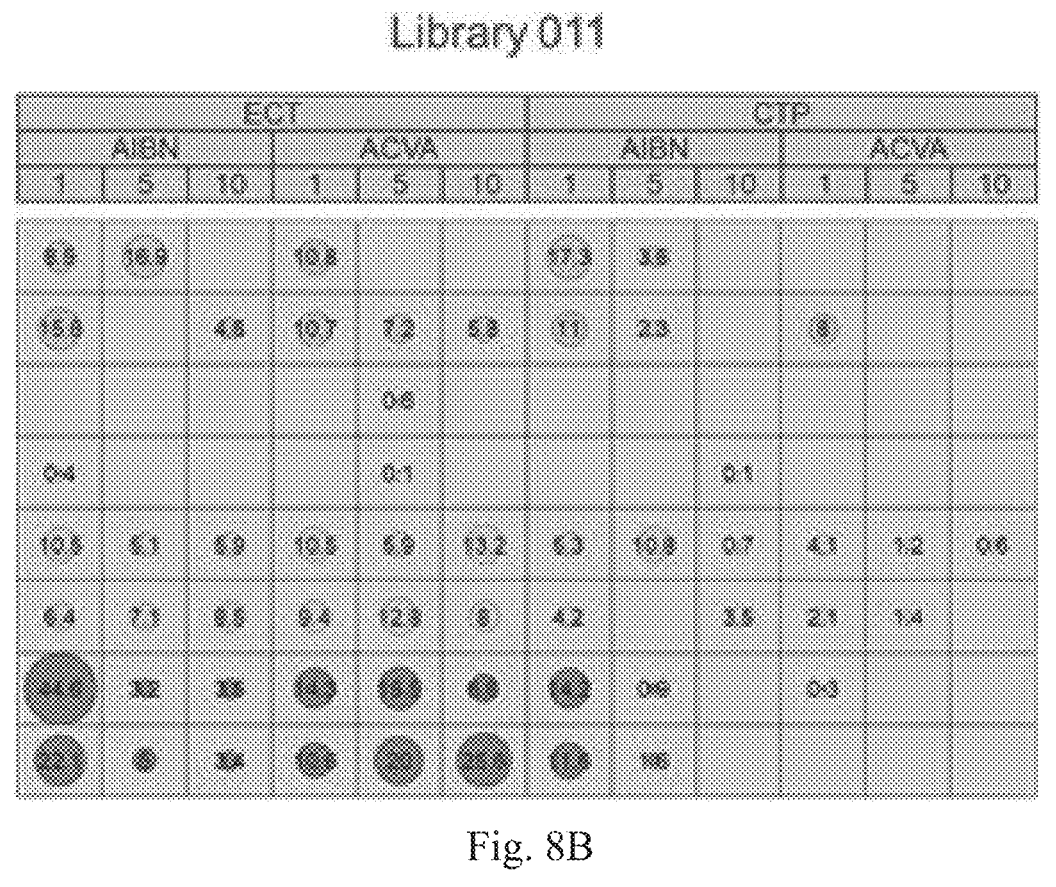

FIG. 8A-B are charts showing polymer Library Block 1 Molecular Weight (Mw) Data for Block 12 of Libraries 0009 (FIG. 8A) and 0011 (FIG. 8B) prepared as described herein and measured as weight average molecular weight.

DETAILED DESCRIPTION OF ILLUSTRATIVE EMBODIMENTS

Figures 1A, 1B:
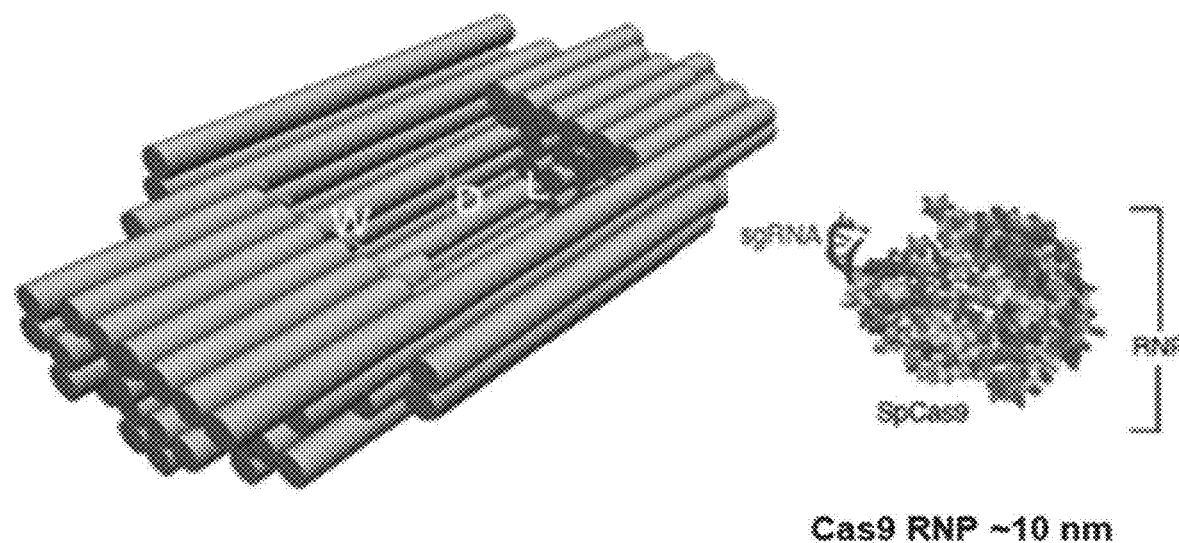
FIG. 1A shows a schematic of a DNA nanostructure showing a central cavity to encapsulate a CRISPR RNP.
FIG. 1B shows the designed dimensions.
Figures 1C, 1D:
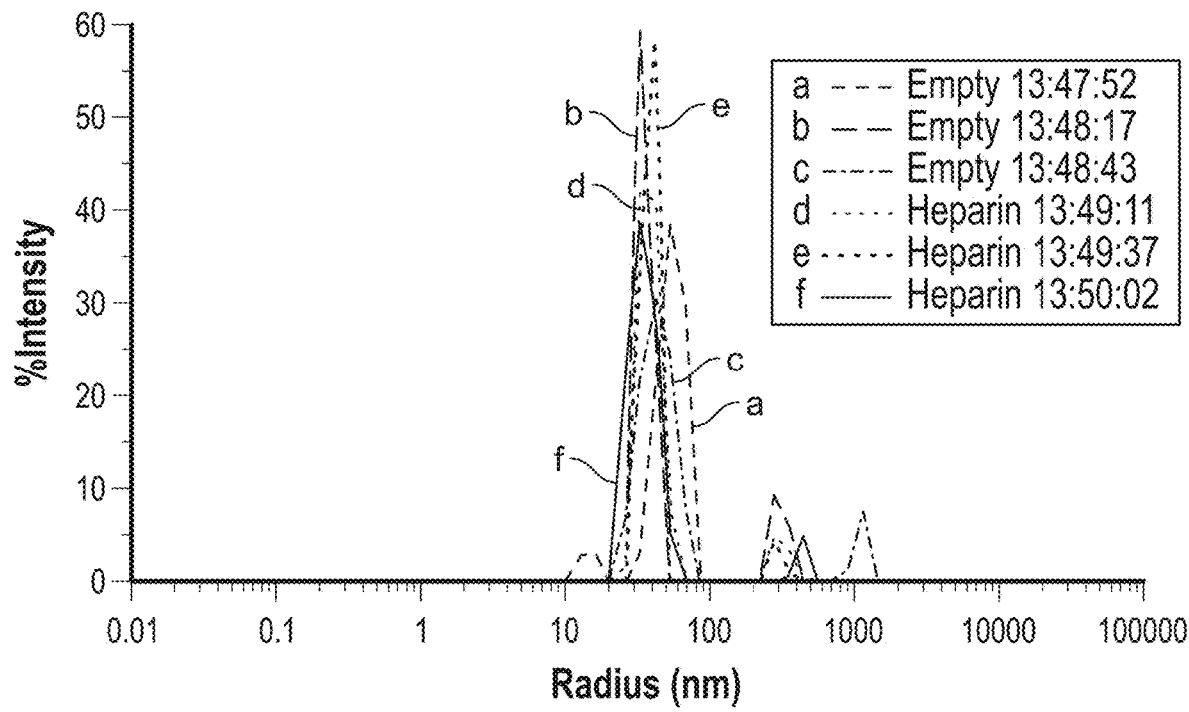
FIG. 1C and FIG. 1D show measured dimensions of the DNA nanostructure as measured with DynaPro and ZetaSizer.

The invention relates to polymer nanoparticle and DNA nanostructure delivery compositions for non-viral delivery, and methods therefor. More particularly, the invention relates to polymer nanoparticle delivery compositions, such as reversible addition-fragmentation chain transfer (RAFT) polymer compositions, and DNA nanostructure delivery compositions, such as DNA origami compositions, for the delivery of more than one payload, or for the delivery of a nucleic acid construct payload of 3 KB or more, and methods therefor.

The following clauses, and combinations thereof, provide various additional illustrative aspects of the invention described herein. The various embodiments described in any other section of this patent application, including the summary portion of the section titled "BACKGROUND AND SUMMARY", the "EXAMPLES", and this "DETAILED DESCRIPTION OF ILLUSTRATIVE EMBODIMENTS" section of the application are applicable to any of the following embodiments of the invention described in the numbered clauses below.

1. A DNA nanostructure delivery composition comprising: i) a single stranded DNA scaffold and ii) one or more oligonucleotides that bind through complementary base pairing with a segment of the DNA scaffold, wherein the one or more oligonucleotides cause the DNA scaffold to fold, and wherein the composition comprises more than one payload for delivery or a nucleic acid construct payload of 3 kB or more.

2. The composition of clause 1 wherein the more than one payload comprises nucleic acids.

3. The composition of clause 2 wherein the nucleic acids comprise DNA or RNA.

4. The composition of clause 2 wherein the nucleic acids comprise a ribonucleoprotein.

5. The composition of clause 2 wherein the payload nucleic acids are used for homology directed repair or as transposable elements.

6. The composition of clause 2 wherein the payload nucleic acids comprise a short guide RNA (sgRNA) and a donor DNA strand.

7. The composition of clause 6 wherein the sgRNA is used for targeting an enzyme to a specific genomic sequence.

8. The composition of clause 1 wherein the payloads comprise a CRISPR associated enzyme.

9. The composition of clause 7 wherein the targeted enzyme is a CRISPR associated enzyme.

10. The composition of clause 1 wherein the payloads comprise a CRISPR associated enzyme, an sgRNA, and a donor DNA strand.

11. The composition of clause 1 wherein the payloads comprise CRISPR/Cas9.

12. The composition of clause 1 wherein the payloads comprise CRISPR/Cas9, an sgRNA, and a donor DNA strand.

13. The composition of clause 1 wherein the payload comprises CRISPR/Cas9 and Cas9 is fused with a deaminase.

14. The composition of clause 1 wherein the payloads comprise a coding sequence for Cas9, an sgRNA, and a donor DNA strand in the form of a plasmid.

15. The composition of clause 1 wherein the payloads consist of one molecule each of CRISPR/Cas9, an sgRNA, and a donor DNA strand.

16. The composition of clause 1 wherein the nucleic acid construct payload of 3 kB or more comprises a CAR-T DNA construct.

17. The composition of clause 1 wherein the payloads comprise an antisense oligonucleotide.

18. The composition of clause 1 wherein the nucleic acid construct payload is of a size selected from the group consisting of 3 kB or more, 3.5 kB or more, 4 kB or more, 4.5 kB or more, 5 kB or more, 5.5 kB or more, 6 kB or more, 6.5 kB or more, 7 kB or more, 7.5 kB or more, 8 kB or more, and 8.5 kB or more.

19. The composition of clause 1 wherein the payloads comprise a reverse transcriptase.

20. The composition of clause 1 wherein the DNA scaffold and the one or more oligonucleotides comprise M13 bacteriophage DNA.

21. The composition of clause 2 wherein the one or more oligonucleotides comprise overhangs that bind through complementary base paring with the payload nucleic acids.

22. The composition of clause 1 wherein the DNA scaffold has an aspect ratio of about 2.

23. The composition of clause 21 wherein the overhangs are located within a cavity within the DNA scaffold.

24. The composition of clause 23 wherein the cavity is covered by a lid and a hinge allowing the payloads to be completely enclosed within the cavity when the lid is shut.

25. The composition of clause 24 wherein the lid comprises oligonucleotide strands that bind through complementary base pairing with other oligonucleotide strands attached to the DNA scaffold when the lid is in the closed position.

26. The composition of clause 1 further comprising a pharmaceutically acceptable carrier.

27. The composition of clause 26 wherein the pharmaceutically acceptable carrier is for parenteral administration or topical administration.

28. The composition of clause 1 wherein the DNA nanostructure is coated with one or more polymers.

29. The composition of clause 28 wherein the one or more polymers comprise polyethylene glycol.

30. The composition of clause 28 wherein the one or more polymers comprise polyethylene glycol poly-L-lysine.

31. The composition of clause 28 wherein the one or more polymers comprise polyethylenimine.

32. The composition of clause 28 wherein the one or more polymers comprise polyethylene glycol poly-L-lysine and polyethylenimine.

33. The composition of clause 1 wherein the DNA nanostructure further comprises a targeting component for targeting to cells.

34. The composition of clause 33 wherein the targeting component is a nucleotide that has a three-dimensional structure capable of binding a target cell receptor.

35. The composition of clause 34 wherein the nucleotide that binds to the target cell receptor binds in conjunction with a peptide aptamer.

36. The composition of clause 34 wherein the nucleotide is an RNA that forms a 'stem-and-loop' structure.

37. A method for gene therapy comprising administering to a patient a DNA nanostructure delivery composition comprising: i) a single stranded DNA scaffold and ii) one or more oligonucleotides that bind through complementary base pairing with a segment of the DNA scaffold, wherein the one or more oligonucleotides cause the DNA scaffold to fold, and wherein the composition comprises more than one payload for delivery or a nucleic acid construct payload of 3 kB or more.

38. The method of clause 37 wherein the more than one payload comprises nucleic acids.

39. The method of clause 38 wherein the nucleic acids comprise DNA or RNA.

40. The method of clause 38 wherein the nucleic acids comprise a ribonucleoprotein.

41. The method of clause 38 wherein the payload nucleic acids are used for homology directed repair or as transposable elements.

42. The method of clause 38 wherein the payload nucleic acids comprise a short guide RNA (sgRNA) and a donor DNA strand.

43. The method of clause 42 wherein the sgRNA is used for targeting an enzyme to a specific genomic sequence.

44. The method of clause 37 wherein the payloads comprise a CRISPR associated enzyme.

45. The method of clause 43 wherein the targeted enzyme is a CRISPR associated enzyme.

46. The method of clause 37 wherein the payloads comprise a CRISPR associated enzyme, an sgRNA, and a donor DNA strand.

47. The method of clause 37 wherein the payloads comprise CRISPR/Cas9.

48. The method of clause 37 wherein the payloads comprise CRISPR/Cas9, an sgRNA, and a donor DNA strand.

49. The method of clause 37 wherein the payload comprises CRISPR/Cas9 and Cas9 is fused with a deaminase.

50. The method of clause 37 wherein the payloads comprise a coding sequence for Cas9, an sgRNA, and a donor DNA strand in the form of a plasmid.

51. The method of clause 37 wherein the payloads consist of one molecule each of CRISPR/Cas9, an sgRNA, and a donor DNA strand.

52. The method of clause 37 wherein the nucleic acid construct payload of 3 kB or more comprises a CAR-T DNA construct.

53. The method of clause 37 wherein the payloads comprise an antisense oligonucleotide.

54. The method of clause 37 wherein the nucleic acid construct payload is of a size selected from the group consisting of 3 kB or more, 3.5 kB or more, 4 kB or more, 4.5 kB or more, 5 kB or more, 5.5 kB or more, 6 kB or more, 6.5 kB or more, 7 kB or more, 7.5 kB or more, 8 kB or more, and 8.5 kB or more.

55. The method of clause 37 wherein the payloads comprise a reverse transcriptase.

56. The method of clause 37 wherein the DNA scaffold and the one or more oligonucleotides comprise M13 bacteriophage DNA.

57. The method of clause 38 wherein the one or more oligonucleotides comprise overhangs that bind through complementary base paring with the payload nucleic acids.

58. The method of clause 37 wherein the DNA scaffold has an aspect ratio of about 2.

59. The method of clause 57 wherein the overhangs are located within a cavity within the DNA scaffold.

60. The method of clause 59 wherein the cavity is covered by a lid and a hinge allowing the payloads to be completely enclosed within the cavity when the lid is shut.

61. The method of clause 60 wherein the lid comprises oligonucleotide strands that bind through complementary base pairing with other oligonucleotide strands attached to the DNA scaffold when the lid is in the closed position.

62. The method of clause 37 further comprising administering a pharmaceutically acceptable carrier to the patient.

63. The method of clause 62 wherein the pharmaceutically acceptable carrier is for parenteral administration or topical administration.

64. The method of clause 37 wherein the DNA nanostructure is coated with one or more polymers.

65. The method of clause 64 wherein the one or more polymers comprise polyethylene glycol.

66. The method of clause 64 wherein the one or more polymers comprise polyethylene glycol poly-L-lysine.

67. The method of clause 64 wherein the one or more polymers comprise polyethylenimine.

68. The method of clause 64 wherein the one or more polymers comprise polyethylene glycol poly-L-lysine and polyethylenimine.

69. The method of clause 37 wherein the DNA nanostructure further comprises a targeting component for targeting to cells of the patient.

70. The method of clause 69 wherein the targeting component is a nucleotide that has a three-dimensional structure capable of binding a target cell receptor.

71. The method of clause 70 wherein the nucleotide that binds to the target cell receptor binds in conjunction with a peptide aptamer.

72. The method of clause 70 wherein the nucleotide is an RNA that forms a 'stem-and-loop' structure.

73. The method of clause 37 wherein the patient has a disease or a disorder selected from the group consisting of cancer, a muscular disorder, a pulmonary disorder, a skin disorder, a neurological disease, neurofibromatosis 1, and a hemoglobinopathy.

74 The method of clause 73 wherein the cancer is selected from the group consisting of lung cancer, bone cancer, pancreatic cancer, skin cancer, uterine cancer, ovarian cancer, endometrial cancer, rectal cancer, stomach cancer, colon cancer, breast cancer, cancer of the esophagus, cancer of the endocrine system, prostate cancer, leukemia, lymphoma, mesothelioma, cancer of the bladder, cancer of the kidney, neoplasms of the central nervous system, brain cancer, and adenocarcinoma.

75. The method of clause 73 wherein the skin disorder is a *Staphlococcus aureus* infection.

76. The method of clause 73 wherein the muscular disorder is muscular dystrophy.

77. The method of clause 37 wherein the DNA nanostructure delivery composition is not cytotoxic to the cells of the patient.

78. A method for targeting a DNA nanostructure delivery composition to cells of a patient, comprising administering to the patient: i) a single stranded DNA scaffold and ii) one or more oligonucleotides that bind through complementary base pairing with a segment of the DNA scaffold, wherein the one or more oligonucleotides cause the DNA scaffold to fold, wherein the composition comprises more than one payload for delivery or a nucleic acid construct payload of 3 kB or more, and wherein the DNA nanostructure comprises a targeting component for targeting to the cells of the patient.

79. The method of clause 78 wherein the more than one payload comprises nucleic acids.

80. The method of clause 79 wherein the nucleic acids comprise DNA or RNA.

81. The method of clause 79 wherein the nucleic acids comprise a ribonucleoprotein.

82. The method of clause 79 wherein the payload nucleic acids are used for homology directed repair or as transposable elements.

83. The method of clause 79 wherein the payload nucleic acids comprise a short guide RNA (sgRNA) and a donor DNA strand.

84. The method of clause 83 wherein the sgRNA is used for targeting an enzyme to a specific genomic sequence.

85. The method of clause 78 wherein the payloads comprise a CRISPR associated enzyme.

86. The method of clause 84 wherein the targeted enzyme is a CRISPR associated enzyme.

87. The method of clause 78 wherein the payloads comprise a CRISPR associated enzyme, an sgRNA, and a donor DNA strand.

88. The method of clause 78 wherein the payloads comprise CRISPR/Cas9.

89. The method of clause 78 wherein the payloads comprise CRISPR/Cas9, an sgRNA, and a donor DNA strand.

90. The method of clause 78 wherein the payload comprises CRISPR/Cas9 and Cas9 is fused with a deaminase.

91. The method of clause 78 wherein the payloads comprise a coding sequence for Cas9, an sgRNA, and a donor DNA strand in the form of a plasmid.

92. The method of clause 78 wherein the payloads consist of one molecule each of CRISPR/Cas9, an sgRNA, and a donor DNA strand.

93. The method of clause 78 wherein the nucleic acid construct payload of 3 kB or more comprises a CAR-T DNA construct.

94. The method of clause 78 wherein the payloads comprise an antisense oligonucleotide.

95. The method of clause 78 wherein the nucleic acid construct payload is of a size selected from the group consisting of 3 kB or more, 3.5 kB or more, 4 kB or more, 4.5 kB or more, 5 kB or more, 5.5 kB or more, 6 kB or more, 6.5 kB or more, 7 kB or more, 7.5 kB or more, 8 kB or more, and 8.5 kB or more.

96. The method of clause 78 wherein the payloads comprise a reverse transcriptase.

97. The method of clause 78 wherein the DNA scaffold and the one or more oligonucleotides comprise M13 bacteriophage DNA.

98. The method of clause 79 wherein the one or more oligonucleotides comprise overhangs that bind through complementary base paring with the payload nucleic acids.

99. The method of clause 78 wherein the DNA scaffold has an aspect ratio of about 2.

100. The method of clause 98 wherein the overhangs are located within a cavity within the DNA scaffold.

101. The method of clause 100 wherein the cavity is covered by a lid and a hinge allowing the payloads to be completely enclosed within the cavity when the lid is shut.

102. The method of clause 101 wherein the lid comprises oligonucleotide strands that bind through complementary base pairing with other oligonucleotide strands attached to the DNA scaffold when the lid is in the closed position.

103. The method of clause 78 wherein the DNA nanostructure is coated with one or more polymers.

104. The method of clause 103 wherein the one or more polymers comprise polyethylene glycol.

105. The method of clause 103 wherein the one or more polymers comprise polyethylene gylcol poly-L-lysine.

106. The method of clause 103 wherein the one or more polymers comprise polyethylenimine.

107. The method of clause 103 wherein the one or more polymers comprise polyethylene glycol poly-L-lysine and polyethylenimine.

108. The method of clause 78 wherein the targeting component is a nucleotide that has a three-dimensional structure capable of binding a target cell receptor.

109. The method of clause 108 wherein the nucleotide that binds to the target cell receptor binds in conjunction with a peptide aptamer.

110. The method of clause 108 wherein the nucleotide is an RNA that forms a 'stem-and-loop' structure.

111. The method of clause 100 wherein the cavity is covered by a lid and a hinge and wherein the lid opens when the DNA nanostructure delivery composition contacts a DNA, an RNA, or an antigen associated with the cells of the patient.

112. A method comprising:
  synthesizing a diverse set of non-viral gene delivery compositions, wherein each non-viral gene delivery composition differs from each other non-viral gene delivery composition of the diverse set with respect to at least one of a set of composition characteristics,
  simultaneously testing one or more quality attributes of each of the non-viral gene delivery composition of the diverse set, and
  creating, using results of the testing, a predictive model that correlates the composition characteristics with the quality attributes.

113. The method of clause 112, wherein the composition characteristics comprise one or more of molecular weight, degree of branching, number of ionizable groups, core-to-corona molecular weight ratio, hydrophilicity, hydrophobicity, propensity for aggregation, size, pKa, logP, and surface charge.

114. The method of clause 112 or clause 113, wherein the quality attributes comprise one or more of cytotoxicity, immunogenicity, transfection efficiency, zeta potential, size, pKa, logP, and loading efficiency.

115. The method of any one of clauses 112-114, wherein the diverse set comprises hundreds of non-viral gene delivery compositions.

116. The method of clause 115, wherein the diverse set comprises thousands of non-viral gene delivery compositions.

117. The method of any one of clauses 112-116, wherein each of the non-viral gene delivery compositions of the diverse set is a DNA nanostructure delivery composition according to one of clauses 1-36.

118. A RAFT block copolymer comprising
  a. a first terminus comprising a first capping unit derived from a first chain transfer agent in a RAFT copolymerization process;
  b. a first block prepared from one or more monomer units covalently attached to the first reactive functional unit, and having a molecular weight (Mn) in the range of about 20 kDa to about 80 kDa and a degree of polymerization in the range of about 20 to about 400;
  c. a second block prepared from one or more monomer units covalently attached to the first block, and having a molecular weight (Mn) in the range of about 5 kDa to about 80 kDa and a degree of polymerization in the range of about 10 to about 500; and
  d. a second terminus comprising a second capping unit derived from a second chain transfer agent;
  wherein the RAFT block copolymer has one or more of an overall molecular weight (Mn) in the range of about 25 kDa to about 160 kDa, and overall degree of polymerization in the range of about 30 to about 900, a size in the range of about of about 10 to about 60 nm, and a maximum corona-to-core ratio (CCR) of about 1 to about 4.

119. The RAFT block copolymer of clause 118, wherein the first block is prepared from one or more monomer units selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

120. The RAFT block copolymer of clause 118 or 119, wherein the first block is prepared from one of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl) methacrylate, or methyl methacrylate.

121. The RAFT block copolymer of any one of clause 118 to 120, wherein the second block is prepared from one or more monomer units selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxycthyl)methacrylate, and methyl methacrylate.

122. The RAFT block copolymer of any one of clauses 118 to 121, wherein the second block is a random copolymer prepared from two different monomer units independently selected from the group consisting of 2-dimethylaminoethyl acrylate. 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

123. The RAFT block copolymer of any one of clauses 118 to 121, wherein the second block is a random copolymer prepared from three different monomer units independently selected from the group consisting of 2-dimethylaminocthyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

124. The RAFT block copolymer of any one of clauses 118 to 123, wherein the second block is a random copolymer prepared from 2-dimethylaminocthyl acrylate, butyl methacrylate, and propyl acrylic acid; or 2-dimethylaminoethyl acrylate and butyl methacrylate; or 2-dimethylaminoethyl acrylate, butyl methacrylate, and ethyl acrylic acid.

125. The RAFT block copolymer of any one of clauses 118 to 124, wherein each chain transfer agent is independently selected from the group consisting of bis(carboxymethyl)trithiocarbonate, bis(2-amino-2-oxoethyl) trithiocarbonate, bis[4-(2-hydroxyethoxycarbonyl)benzyl] trithiocarbonate, 4-cyano-4-(ethylsulfanylthiocarbonyl) sulfanylvpentanoic acid, 4-cyano-4-((phenylcarbonothioyl) thio)pentanoic acid, and 4-cyano-4-[(dodecylsulfanylthiocarbonyl)sulfanyl] pentanoic acid.

126. The RAFT block copolymer of any one of clauses 118 to 125, wherein the first capping unit is of the formula

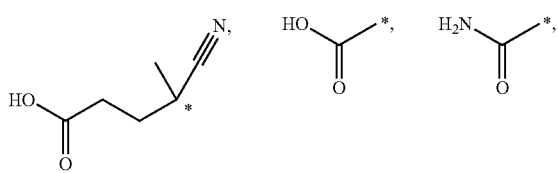

-continued

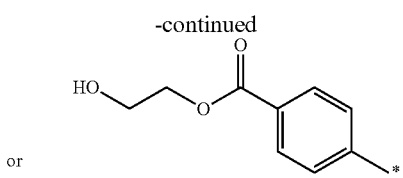

or wherein * represents a point of covalent attachment to the first block.

127. The RAFT block copolymer of any one of clauses 118 to 126, wherein the second capping unit is of the formula

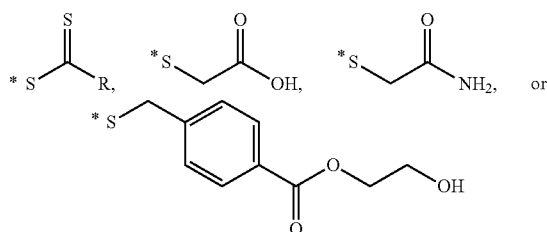

wherein * represents a point of covalent attachment to the second block, and R is —$SC_2$-$C_{12}$ alkyl or $C_6H_5$, 128. A method of preparing a RAFT block copolymer comprising:
    i. contacting a first chain transfer agent, a first initiator and one or more monomer units to provide a first block;
    ii. contacting a second chain transfer agent, a second initiator and one or more monomer units to provide a second block
    iii. contacting the first block and the second block under conditions capable of coupling the blocks to provide the RAFT block copolymer.

129. The method of clause 128, wherein the first chain transfer agent is a diamino or dihydroxy chain transfer agent, and the second chain transfer agent is a dicarboxylic acid chain transfer agent.

130. The method of clause 128 or 129, wherein the first chain transfer agent is bis(2-amino-2-oxoethyl) trithiocarbonate or bis[4-(2-hydroxyethoxycarbonyl)benzyl] trithiocarbonate, and the second chain transfer agent is bis(carboxymethyl)trithiocarbonate.

131. The method of clause 128, wherein the first chain transfer agent is a dicarboxylic acid chain transfer agent, and the second chain transfer agent is a diamino or dihydroxy chain transfer agent.

132. The method of clause 128 or 131, wherein the first chain transfer agent is bis(carboxymethyl)trithiocarbonate, and the second chain transfer agent is bis(2-amino-2-oxoethyl) trithiocarbonate or bis[4-(2-hydroxyethoxycarbonyl) benzyl] trithiocarbonate.

133. The method of any one of clauses 128 to 132, wherein the step (iii) is carried out under conditions capable of promoting amidation or esterification.

134. The method of any one of clauses 128 to 133, wherein the one or more monomer units in step (i) are independently selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

135. The method of any one of clauses 128 to 134, wherein the one or more monomer units in step (i) is one of 2-dimethylaminoethyl acrylate. 2-(diethylamino) ethyl methacrylate, 2-(diisopropylamino) ethyl methacrylate, butyl methacrylate, ethyl acrylic acid, propyl acrylic acid, (hydroxyethyl)methacrylate, or methyl methacrylate.

136. The method of any one of clauses 128 to 135, wherein the one or more monomer units in step (ii) are independently selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

137. The method of any one of clauses 128 to 136, wherein the one or more monomer units in step (ii) are two different monomer units independently selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

138. The method of any one of clauses 128 to 136, wherein the one or more monomer units in step (ii) are three different monomer units independently selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

139. The method of any one of clauses 128 to 138, wherein the one or more monomer units in step (ii) are 2-dimethylaminoethyl acrylate, butyl methacrylate, and propyl acrylic acid; or 2-dimethylaminocthyl acrylate and butyl methacrylate; or 2-dimethylaminoethyl acrylate, butyl methacrylate, and ethyl acrylic acid.

140. The method of any one of clauses 128 to 139, wherein the RAFT block copolymer has one or more of an overall molecular weight (Mn) in the range of about 25 kDa to about 160 kDa, and overall degree of polymerization in the range of about 30 to about 900, a size in the range of about of about 10 to about 60 nm, and a maximum corona-to-core ratio (CCR) of about 1 to about 4.

141. A method of preparing a library of RAFT block copolymers comprising:
 i. providing an array of reaction mixtures in a multiwell plate, wherein each well comprises a mixture of a first chain transfer agent, a first initiator, one or more monomer units, and optionally a solvent or solvent mixture;
 ii. reacting the mixture in each well under conditions that promote RAFT copolymerization to provide a series of first block copolymers in the wells of the multiwell plate;
 iii. quenching the reactions in the wells of the multiwell plate;
 iv. purifying the first block copolymer in each well of the multiwell plate;
 v. optionally characterizing the first block copolymer in each well of the multiwell plate;
 vi. optionally purifying the first block copolymer in each well of the multiwell plate;
 vii. contacting to the first block copolymer in each well of the multiwell plate with a second array of reaction mixtures comprising a second chain transfer agent, a second initiator, and one or more monomer units, and optionally a solvent or solvent mixture;
 viii. reacting the components of step (vii) under conditions that promote RAFT copolymerization to provide a series of RAFT block copolymers in the wells of the multiwell plate;
 ix. quenching the reactions in the wells of the multiwell plate;
 x. purifying the RAFT block copolymer in each well of the multiwell plate; and
 xi. optionally characterizing the RAFT block copolymer in each well of the multiwell plate.

142. The method of clause 142, wherein the one or more monomer units in step (i) are independently selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

143. The method of clause 141 or 142, wherein the one or more monomer units in step (i) is one of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, or methyl methacrylate.

144. The method of any one of clauses 141 to 143, wherein the one or more monomer units in step (vii) are independently selected from the group consisting of 2-dimethylaminocthyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

145. The method of any one of clauses 141 to 144, wherein the one or more monomer units in step (vii) are two different monomer units independently selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

146. The method of any one of clauses 141 to 145, wherein the one or more monomer units in step (vii) are three different monomer units independently selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

147. The method of any one of clauses 141 to 146, wherein the one or more monomer units in step (vii) are 2-dimethylaminoethyl acrylate, butyl methacrylate, and propyl acrylic acid; or 2-dimethylaminoethyl acrylate and butyl methacrylate; or 2-dimethylaminoethyl acrylate, butyl methacrylate, and ethyl acrylic acid.

148. The method of any one of clauses 141 to 147, wherein the first and second chain transfer agent are the same or different.

149. The method of any one of clauses 141 to 148, wherein the first and second chain transfer agent are the same.

150. The method of any one of clauses 141 to 148, wherein the first and second chain transfer agent are different.

151. The method of any one of clauses 141 to 150, wherein the first and second chain transfer are each independently selected from the group consisting of bis(carboxymethyl)trithiocarbonate, bis(2-amino-2-oxoethyl) trithiocarbonate, bis[4-(2-hydroxyethoxycarbonyl)benzyl] trithiocarbonate, 4-cyano-4-(ethylsulfanylthiocarbonyl) sulfanylvpentanoic acid, 4-cyano-4-((phenylcarbonothioyl)thio)pentanoic acid, and 4-cyano-4-[(dodecylsulfanylthiocarbonyl)sulfanyl] pentanoic acid.

152. The method of any one of clauses 141 to 151, wherein the solvent or mixture of solvents provided in steps (i) and (vii) is one or more of dimethylformamide, dimethylsulfoxide, isopropyl alcohol, hexanes, 1,4-dioxane, and tetrahydrofuran.

153. The method of any one of clauses 141 to 152, wherein the steps (ii) and (viii) are each carried out under an atmosphere of saturated solvent of steps (i) and (vii).

154. The method of any one of clauses 141 to 153, wherein characterizing in steps (v) and (xi) are technique is high throughput zeta potential measurement using a multi-well plate dynamic light scattering device to measure changes in the interaction parameter or the second virial coefficient with respect to concentration or ionic strength or high throughput measurement of the differential refractive index of the polymer.

155. The method of any one of clauses 141 to 154, wherein the quenching steps (iii) and (ix) are carried out by exposure of the multiwell plate to oxygen.

156. The method of any one of clauses 141 to 155, wherein the purifying steps (iv) and (x) are carried out via filtration, diafiltration, or dialysis in a multiwell format.

157. A composition comprising a RAFT block copolymer according to any one of clauses 118 to 127 or a RAFT block copolymer prepared according to the method of any one of clauses 128 to 156.

158. A RAFT block copolymer conjugate comprising a RAFT block copolymer according to any one of clauses 118 to 127 or a RAFT block copolymer prepared according to the method of any one of clauses 128 to 156, and further comprising a biomolecule, drug, or label covalently attached to the RAFT block copolymer through a functional group on one of the first or second chain transfer agents that is incorporated into the RAFT block copolymer.

159. The RAFT block copolymer conjugate of clause 158, wherein the biomolecule and the RAFT block copolymer are covalently attached via an amide bond or an ester bond.

160. A method of preparing a RAFT block copolymer conjugate comprising a RAFT block copolymer according to any one of clauses 118 to 127 or a RAFT block copolymer prepared according to the method of any one of clauses 128 to 156 and a biomolecule, drug, or label, wherein the RAFT block copolymer and the biomolecule, drug, or label are covalently attached through a functional group on one of the first or second chain transfer agents that is incorporated into the RAFT block copolymer.

161. The method of clause 160, wherein a covalent bond is formed between the RAFT block copolymer and the biomolecule, drug, or label via an EDC-NHS reaction of a functional group on one of the first or second chain transfer agents that is incorporated into the RAFT block copolymer.

162. The method of clause 160 or 161, wherein the functional group a carboxylate group that is reacted with a primary amine on the biomolecule, drug, or label via EDC-NHS chemistry.

163. The method of any one of clauses 160 to 162, wherein the RAFT block copolymer and the biomolecule, drug, or label are covalently attached via an amide bond.

164. The method of any one of clauses 160 to 163, wherein the first or second chain transfer agent is 2-(dodecylthiocarbonothioylthio)-2-methylpropionic acid or 4-cyano-4-(ethylsulfanylthiocarbonyl) sulfanylvpentanoic acid.

165. The method of any one of clauses 160 to 164, wherein the biomolecule is a protein.

166. The method of any one of clauses 160 to 164, wherein the label is avidin or biotin.

167. A RAFT block copolymer complex comprising a RAFT block copolymer according to any one of clauses 118 to 127 or a RAFT block copolymer prepared according to the method of any one of clauses 128 to 156, and further comprising a payload complexed to the RAFT block copolymer through electrostatic interaction.

168. The RAFT block copolymer complex of clause 167 wherein the payload comprises nucleic acids.

169. The RAFT block copolymer complex of clause 168 wherein the nucleic acids comprise DNA or RNA.

170. The RAFT block copolymer complex of clause 168 wherein the nucleic acids comprise a ribonucleoprotein.

171. The RAFT block copolymer complex of clause 168 wherein the payload nucleic acids are used for homology directed repair or as transposable elements.

172. The RAFT block copolymer complex of clause 168 wherein the payload nucleic acids comprise a short guide RNA (sgRNA) and a donor DNA strand.

173. The RAFT block copolymer complex of clause 172 wherein the sgRNA is used for targeting an enzyme to a specific genomic sequence.

174. The RAFT block copolymer complex of clause 167 wherein the payload comprises a CRISPR associated enzyme.

175. The RAFT block copolymer complex of clause 173 wherein the targeted enzyme is a CRISPR associated enzyme.

176. The RAFT block copolymer complex of clause 167 wherein the payload comprises a CRISPR associated enzyme, an sgRNA, and a donor DNA strand.

177. The RAFT block copolymer complex of clause 167 wherein the payload comprises CRISPR/Cas9.

178. The RAFT block copolymer complex of clause 167 wherein the payload comprises CRISPR/Cas9, an sgRNA, and a donor DNA strand.

179. The RAFT block copolymer complex of clause 167 wherein the payload comprises CRISPR/Cas9 and Cas9 is fused with a deaminase.

180. The RAFT block copolymer complex of clause 167 wherein the payload comprises a coding sequence for Cas9, an sgRNA, and a donor DNA strand in the form of a plasmid.

181. The RAFT block copolymer complex of clause 167 wherein the payload consists of one molecule each of CRISPR/Cas9, an sgRNA, and a donor DNA strand.

182. The RAFT block copolymer complex of clause 167 wherein the payload comprises a CAR-T DNA construct.

183. The RAFT block copolymer complex of clause 167 wherein the payload comprises an antisense oligonucleotide.

184. The RAFT block copolymer complex of clause 167 wherein the payload is a nucleic acid and the nucleic acid payload is of a size selected from the group consisting of 3 kB or more, 3.5 kB or more, 4 kB or more, 4.5 kB or more, 5 kB or more, 5.5 kB or more, 6 kB or more, 6.5 kB or more, 7 KB or more, 7.5 kB or more, 8 kB or more, and 8.5 kB or more.

185. The RAFT block copolymer complex of clause 167 wherein the payload comprises a reverse transcriptase.

186. The RAFT block copolymer complex of clause 167 further comprising a pharmaceutically acceptable carrier.

187. The RAFT block copolymer complex of clause 186 wherein the pharmaceutically acceptable carrier is for parenteral administration or topical administration.

188. The RAFT block copolymer complex of clause 167 further comprising a targeting component for targeting to cells.

189. A method for gene therapy comprising administering to a patient a RAFT block copolymer of any one of clauses 167 to 188.

190. A method for targeting a polymer nanoparticle composition to cells of a patient, comprising administering to the patient a RAFT block copolymer of any one of clauses 167 to 188.

191. The method of any one of clauses 112-116, wherein each of the non-viral gene delivery compositions of the diverse set is a RAFT block copolymer according to one of clauses 118-127.

In various embodiments, the polymer nanoparticle or DNA nanostructure delivery compositions described herein may comprise any non-viral composition for in vivo delivery of the payloads. By way of example, the polymer nanoparticle or nanostructure DNA delivery compositions described herein may be selected from the group comprising: polymer nanoparticles, reversible addition-fragmentation chain transfer (RAFT) polymers, polyplexes, micelles, polymersomes, dendrimers, emulsion, synthetic virus-like particles, carbon nanotubes, emulsions, and any DNA nanostructure delivery composition, such as DNA origami structures.

In the embodiments where polymer nanoparticle compositions (e.g., RAFT copolymers) or DNA nanostructure delivery compositions are used, the two platforms have a high degree of tunability in structure and function, opportunities to protect payloads from adverse reactions or degradation by the immune system, and cell targeting via surface charge, particle size, or conjugation with various aptamers. These delivery systems also lend themselves to computer aided design, and they both have suitable pathways to robust, commercial scale manufacturing processes with higher yields and fewer purification steps than viral manufacturing processes.

In one embodiment, a DNA nanostructure delivery composition is provided. A DNA nanostructure delivery composition (e.g., a DNA origami structure), as a delivery platform, is programmable and offers an opportunity for precise scale-up and manufacturing. In this embodiment, the biologic and non-viral nature of the DNA nanostructure delivery composition reduces the chance of adverse immune reactions. In this embodiment, control of each nucleotide that forms a part of the DNA nanostructure delivery composition (e.g., DNA origami nanostructure) allows for the precise design and modification of the structure, including suitable chemical moieties which can make in vivo delivery and endosomal escape possible.

In this embodiment, the DNA nanostructure delivery composition can undergo self-base pairing (i.e., a DNA origami structure) to fold into structures that can form the single-stranded DNA scaffold that can encapsulate a payload.

In another embodiment, the DNA nanostructure delivery composition can comprise i) a single stranded DNA scaffold and ii) one or more oligonucleotides that bind through complementary base pairing with a segment of the DNA scaffold, wherein the one or more oligonucleotides cause the DNA scaffold to fold. In this embodiment, the one or more oligonucleotides can comprise overhangs that bind through complementary base paring with the payload nucleic acids. In this embodiment, the overhangs can be located within a cavity within the DNA scaffold, and the cavity can be covered by a lid and a hinge allowing the payloads to be completely enclosed within the cavity when the lid is shut. In this embodiment, the lid can further comprise oligonucleotide strands that bind through complementary base pairing with other oligonucleotide strands attached to the DNA scaffold when the lid is in the closed position. DNA nanostructure delivery compositions (e.g., DNA origami structures) are described in U.S. Pat. No. 9,765,341, incorporated herein by reference.

As used herein, the term "complementary base pairing" refers to the ability of purine and pyrimidine nucleotide sequences to associate through hydrogen bonding to form double-stranded nucleic acid molecules. Guanine and cytosine, adenine and thymine, and adenine and uracil are complementary and can associate through hydrogen bonding resulting in the formation of double-stranded nucleic acid molecules when two nucleic acid molecules have "complementary" sequences. The complementary sequences can be DNA or RNA sequences. The complementary DNA or RNA sequences are referred to as a "complement."

In one aspect, the polymer nanoparticle composition (e.g., RAFT polymer) or the DNA nanostructure delivery compositions of the invention can comprise more than one payload for delivery to target cells, or a nucleic acid construct payload of 3 kB or more for delivery to target cells. In this embodiment, the nucleic acid construct payload of 3 kB or more can be DNA or RNA. In any of the DNA nanostructure delivery composition embodiments described herein, the DNA scaffold and the one or more oligonucleotides can comprise M13 bacteriophage DNA.

In one illustrative embodiment, the DNA nanostructure delivery composition further comprises a targeting component for targeting to cells. In one aspect, the targeting component can be a nucleotide that is an RNA that forms a 'stem-and-loop' structure. In this aspect, the DNA nanostructure delivery composition can be designed so that the polynucleotide strands fold into three-dimensional structures via a series of highly tuned 'stem-and-loop' configurations. In this embodiment, the DNA nanostructure delivery composition can have a high affinity for protein receptors expressed on specific cells resulting in targeting of the DNA nanostructure delivery composition and the payload to the specific cells. In this embodiment, the polynucleotide that binds to the target cell receptor can bind in conjunction with a peptide aptamer. In another aspect, the DNA nanostructure delivery composition can be folded so that, in the presence of certain biomarkers such as cell receptors, microRNA, DNA, RNA or an antigen, the self-base pairs are disrupted and the DNA nanostructure delivery composition can unfold, resulting in the triggered release of the payload only in the presence of the specific biomarker. For example, a lock-and-key mechanism for triggered opening of a DNA nanostructure delivery composition (e.g., a DNA origami construct) has been demonstrated previously (Andersen, et al., Nature, Vol. 459, pages 73-76(2009)), incorporated by reference herein. In these embodiments, the use of the DNA nanostructure delivery composition to create three-dimensional structures that target cells and tissues allows for more efficient delivery of payloads with fewer side effects, since the DNA nanostructure delivery composition can have low immunogenicity, and the payload will be released only in the presence of RNA or peptide biomarkers, for example, that exist in the cytosol of target cells and tissues.

In the embodiment where a DNA nanostructure delivery composition is used, computer aided design tools can predict the nucleotide sequence necessary to produce highly engineered DNA nanostructure delivery compositions. For gene delivery, these DNA nanostructure delivery compositions offer the advantages of encapsulation efficiency, as the size and shape of the structure can be tailored to fit the cargo. In another aspect, loading efficiency can be increased by incorporating nucleic acid payloads into the encapsulating DNA nanostructure delivery composition itself.

The non-viral delivery vehicles needed for translation of gene editing treatments can be synthesized with repeatable, versatile and scalable methods to meet GMP requirements. For these reasons, lipid nanoparticles have been used for most non-viral nucleic acid delivery vehicles in clinical trials. Although polymer nanoparticles have been less commonly used for clinical nucleic acid delivery, polymer synthesis methods provide these types of scalable manufacturing benefits in ways that cannot be matched by other biomaterials such as lipids. Recently, methods of producing cationic block copolymer nanoparticles using reversible-addition fragmentation chain transfer (RAFT) polymerization have been standardized to demonstrate rigor and reproducibility necessary for commercial scale nanocarrier production. Given the robustness, versatility and sophistication of the RAFT copolymerization process, it is an attractive route to synthesizing non-viral delivery vehicle alternatives to AAVs.

The true potential of polymer nanoparticles for delivery of genetic medicines has not been realized due to the slow speed of research, requiring weeks to design, synthesize and test on the order of tens of nanoparticles. The design space of for these materials is vast, but past efforts have only been superficial. However, it has recently been demonstrated that these RAFT copolymers can be synthesized in multiplex, high-throughput arrays in multi-well plates. The inventors use these high throughput multi-well techniques to accelerate the discovery of polymer delivery vehicles for CRISPR tools, synthesizing and testing dozens of nanoparticles at a time, with the opportunity to screen polymer designs on the order of thousands for a given CRISPR payload and target cell. This is at least two orders of magnitude larger than the design space typically explored for polymer nanoparticles. These methods are currently being used for the encapsulation and delivery of pDNA encoding for Cas9 and gRNA editing systems to somatic cell lines.

As is the case with lipid nanoparticles, polymer nanoparticle delivery vehicles are designed using cationic polymers that form complexes with negatively charged nucleic acids and enhance interaction with the negative resting potential of the cellular membrane. However, the same positive surface charge may also lead to cytotoxicity in high enough doses. The RAFT copolymers prepared according to the methods described herein have been shown to be well tolerated by cells as provided in the examples described herein.

In one illustrative aspect, polymer nanoparticles may be used as delivery vehicles according to the present disclosure. In one embodiment, the polymer nanoparticles may be made by RAFT copolymerization to synthesize a diverse set of block copolymers, and to screen their ability to form complexes with a payload. In one aspect, polymer nanoparticles (e.g., RAFT copolymers) may be produced by chemically bonding a payload to a constituent polymer, such as by the grafting of the payload onto RAFT copolymers using chain transfer agents, and subsequently assembling the polymers into a delivery vehicle. In various embodiments, payloads may be combined with the polymer nanoparticles or DNA nanostructure delivery compositions using any or all of covalent bonds, electrostatic interactions, and ligand affinity interactions. In one aspect, covalent bonding methods include the use of EDC/NHS to form stable amide bonds between the payload and the polymer nanoparticles for improved stability (both "on the shelf" and in vivo), case of separation and extraction, and sensitive detection. In another illustrative aspect, electrostatic bonding methods include the use of cationic polymer nanoparticles or DNA nanostructure delivery compositions that electrostatically complex with the payload. In another embodiment, ligand affinity bonding includes the use of ligands such as avidin and biotin, both covalently bonded to the polymer nanoparticles or DNA nanostructure delivery compositions and the payload via EDC/NHS chemistry to yield the stable combination of the payload and the polymer nanoparticles or DNA nanostructure delivery compositions.

In one illustrative embodiment, RAFT copolymerization may be achieved using chain transfer agents (CTAs) containing one or more terminal carboxyl groups in order to obtain carboxy terminated polymers with ends available for bonding to the payload via the methods described above. In this embodiment, when the resulting mono or di-carboxy terminated polymer is dispersed in a low pH (e.g., a pH of less than 6) buffer, both ends of the polymer are exposed and available for labeling via EDC/NHS chemistry. In this embodiment, when the polymer is transferred to a physiological pH (~pH 7), the core blocks self-assemble, encapsulating the payload in the hydrophobic core, to be released and exposed upon acidification in the endosomal compartment of a cell.

RAFT copolymers as prepared herein can be described by the following structure:

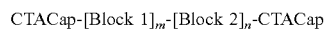

where each CTACap is a capping unit derived from the chain transfer agent(s) used in the process for preparing the RAFT copolymer. The CTA used for preparing each of Block 1 and Block 2 can be the same or different. In some embodiments, the CTA used to prepare each of Block 1 and Block 2 is the same (e.g. macroCTA). In some embodiments, the CTA used to prepare each of Block 1 and Block 2 is different. In some embodiments, the CTA used to prepare one or both of Block 1 and Block 2 comprises a functional group for the covalent attachment of a biomolecule, drug, or label to the RAFT copolymer. In some embodiments, the covalent attachment can be via an ester or an amide bond. In some embodiments, the covalent attachment can be via EDC-NHS chemistry. In some embodiments, the first capping unit is of the formula

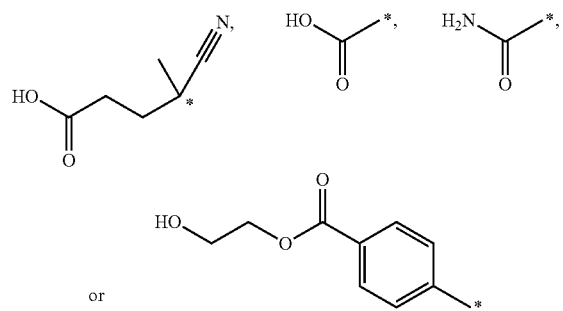

wherein * represents a point of covalent attachment to the first block. In some embodiments, the second capping unit is of the formula

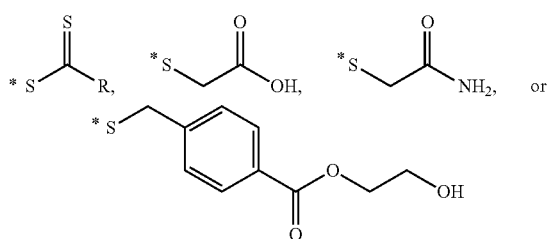

wherein * represents a point of covalent attachment to the second block, and R is —$SC_2$-$C_{12}$ alkyl or $C_6H_5$.

In some embodiments, the RAFT copolymer can be complexed with a biological molecule, such as a DNA molecule, via electrostatic interaction.

In some embodiments, each of Block 1 and Block 2 can comprise one or more monomer units polymerized using a RAFT polymerization process. It will be appreciated that the identity of the monomer units is not particularly limited so long as the monomer units being used are compatible with a RAFT polymerization process. Suitable monomer units include but are not limited to 2-dimethylaminoethyl acrylate (DMAEMA), 2-(diethylamino) ethyl methacrylate (DEAEMA), 2-(diisopropylamino) ethyl methacrylate, butyl methacrylate (BMA), ethyl acrylic acid (EAA), propyl acrylic acid (PAA), (hydroxyethyl)methacrylate (HEMA), and methyl methacrylate (MMA), Acrylic acid (AA), Aminoethyl methacrylate (AEM), 2-(2-aminoethylamino) ethyl methacrylate (AEAEMA), N-(2-Aminoethyl) methacrylamide (AEMA), 3-amino-2-hydroxypropyl methacrylate (AEAHPMA), 3-aminopropyl methacrylamide (AHPMA), Amidoamine (AMA), N-(3-Aminopropyl)methacrylamide (APMA), 5-(3-(Amino)-propoxy)-2-nitrobenzyl methacrylate (APNBMA), N-[N'-(2-aminoethyl)-2-aminoethyl]aspartamide (Asp(DET)), 2-Azidoethyl Methacrylate (AzEMA), Branched polyethyleneimine (BPEI), Carboxybetaine methacrylate (CBMA), Diallyldimethylammonium chloride (DADMAC), 2-(Diethylamino)ethanethiol hydrochloride (DEAET), N,N-dimethylamino-2-ethylmethacrylate) (DMA), N-[3-(N,N-dimethylamino)propyl]-methacrylamide (DMAPMA), N,N'-dimethylbutylamine (DMBA), N,N'-dimethylethanolamine (DMEA), N,N-dimethylamino-2-ethylacrylate or 2-(dimethylamino)ethyl acrylate (DMAEA), 1,2-Dimyristoyl-sn-glycero-3-phosphocholine (DMPC), 1,2-Dioleoyl-sn-glycero-3-phosphocholine (DOPC), 1,2-Dioleoyl-sn-glycero-3-phosphoethanolamine (DOPE), 1,4,7,10-Tetraazacyclododecane-1,4,7,10-tetraacetic acid (DOTA), 1,2-Dioleoyl-3-trimethylammonium Propane (DOTAP), 1,2-Diphytanoyl-sn-glycero-3-phosphoethanolamine (DPyPE), N-[2-(2-pyridyldithio)]ethyl methacrylamide (DTEMA), Ethyl acrylic acid (EAA), N-acetyl-D-galactose (GalNAc), N-acetyl-D-glucose (GlcNAc), Glycidyl methacrylate (GMA), Glycosylphosphatidylinositol (GPI), 2-Hydroxyethyl methacrylate (HEMA), N-(2-Hydroxypropyl)-Methacrylamide (HPMA), Methacryloxysuccinimide (MAS), Methacrylamidotrehalose (MAT), 2-Methacryloyloxyethyl phosphorylcholine (MPC), N-Hydroxysuccinimide (NHS), N-(Acryloxy)succinimide (NHSA), N-(Methacryloxy)succinimide methacrylate (NHSMA), Oligoethylene glycol methacrylate (OEGMA), Oligoethylenimine (OEI), Poly(N-methyl 4-vinylpyridine iodide) (P4VPQ), Poly(2-aminoethylmethacrylamide) (PAEMA), N-(N'-{N''-[N'''-(2-aminoethyl)-2-aminoethyl]-2-aminoethyl}-2-aminoethyl)-aspartamide (Asp(TEP)), Poly(ε-caprolactone) (PCL), Poly(ethylene glycol) (PEG), Poly(ethylene glycol) acrylate (PEGA), Poly(ethylene glycol) methyl ether methacrylate (PEGMEMA, Poly(ethylene glycol) ethyl ether methacrylate (PEGEEMA), Poly(ethylene glycol) methacrylate (PEGMA), Pentaethylenchexamine (PEHA), Poly(ethylenimine) (PEI), Pentafluorophenyl (PFP), Pentafluorophenyl acrylate (PFPA), Pentafluorophenyl methacrylate (PFPMA), Poly(glutamic acid) (PGA), Poly-(glycoamidoamine) (PGAA), Poly(glycidylbutylamine) (PGBA), Poly(glycidyl methacrylate) functionalized with ethanolamine (PGEA), Poly(glycidyl methacrylate) (PGMA), Poly(N-(2-Hydroxypropyl)methacrylamide) (PHPMA), Poly(lactic acid) (PLA), Poly(L-glutamate) (PLG), Poly(lactic-co-glycolic acid) (PLGA,), Poly(L-lysine) (PLL), Poly(L-lactic acid) (PLLA), Poly(lauryl methacrylate) (PLMA), Poly(methacrylic acid) (PMAA), Poly-(2-deoxy-2-methacrylamido glucopyranose) (PMAG), Poly-(methyl methacrylate) (PMMA), Poly(2-methacryloyloxyethyl phosphorylcholine) (PMPC), Poly[N-(3-(methacryloylamino) propyl)-N,N-dimethyl-N-(3-sulfopropyl) ammonium hydroxide] (PMPD), Poly(n-butyl acrylate) (PnBA), Poly(n-butyl methacrylate) (PnBMA), Poly(N-isopropyl acrylamide) (PNIPAM), Poly(oligoethylene glycol methacrylate) (POEGMA), Poly(propylene glycol) (PPG), Poly(propylenimine) (PPI), Poly(styrene) (PS), Poly(sodium 4-styrenesulfonate) (PSS), Poly(tributyl-(4-vinylbenzyl)phosphonium chloride) (PTBP), Poly(triethyl-(4-vinylbenzyl)phosphonium chloride) (PTEP), Poly((2-trimethylamino)ethyl metacrylate chloride) (PTMAEMA), Poly((vinylbenzyl) trimethylammonium) (PVBTMA), Poly (2-vinyl-4,4-dimethylazlactone) (PVDMA),Poly(N-ethyl-4-vinylpyridinium bromide) (PVP), Quaternized Poly-DMAEMA (QPDMAEMA), Sulfobetaine methacrylate (SBMA), and the like. In some embodiments, the monomer units used to make Block 1 and/or Block 2 of RAFT copolymers as described herein are selected from the group consisting of 2-(dimethylamino) ethyl acrylate (DMAEEA), 2-(diethylamino) ethyl methacrylate (DEAEEA), 2-(diisopropylamino) ethyl methacrylate (DIEAMA), butyl methacrylate (BMA), ethyl acrylic acid (EAA), propyl acrylic acid (PAA), (hydroxyethyl)methacrylate, and methyl methacrylate (MMA).

In some embodiments, the RAFT copolymers provided herein can be described by the formula:

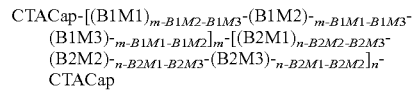

For example, a RAFT copolymer as described herein having a single monomer in Block 1 of 25 units and 3 different monomers in Block 2 having an average monomer unit ratio of 20:10:5 for a total n of 35, can be described by the general formula

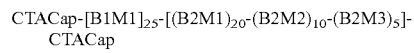

It will be further appreciated that the polymers prepared using a RAFT polymerization are random polymers having a distribution of units and hence molecular weights. Therefore, the cartoon representation of Block 2 in the example above is a random copolymer comprising 35 monomer units of B2M1, B2M2, and B2M3 in the ratio described above.

In another illustrative embodiment, the polymer nanoparticle composition or the DNA nanoparticle delivery composition can be coated with one or more polymers to protect the compositions from immune responses or to enhance endosomal escape. In one embodiment, the one or more polymers comprise polyethylene glycol. In another embodiment, the one or more polymers comprise polyethylene glycol poly-L-lysine. In yet another embodiment, the one or more polymers comprise polyethyleniminc. In an additional embodiment, the one or more polymers comprise polyethylene glycol poly-L-lysine and polyethyleniminc.

It will be appreciated that tuning the parameters and properties of the RAFT copolymers described herein can be advantageous to their use in the compositions and methods as described herein. Accordingly, the methods for preparing RAFT copolymers cither in singleton or in library format as described herein are capable of providing particular parameters and properties of the RAFT copolymers.

In some embodiments, a RAFT block copolymer as described herein has one or more of an overall molecular weight ($M_n$) in the range of about 25 kDa to about 160 kDa, and overall degree of polymerization in the range of about 30 to about 900, a size in the range of about of about 10 to about 60 nm, and a maximum corona-to-core ratio (CCR) of about 1 to about 4. In some embodiments, the overall molecular weight (Mn) in the range of about 30 kDa to about 120 kDa, about 40 kDa to about 110 kDa about 50 kDa to about 100 kDa, about 60 kDa to about 90 kDa, about 40 kDa to about 80 kDa, and about 40 kDa to about 60 kDa. In some embodiments, the overall degree of polymerization in the range of about 40 to about 850, about 60 to about 800, about 100 to about 700, about 200 to about 600, or about 300 to about 500. In some embodiments, the size is in the range of about of about 10 to about 50 nm, about 15 to about 45 nm, about 20 to about 40 nm, or about 25 to about 35 nm. In some embodiments, the maximum corona-to-core ratio (CCR) is less than 4, or less than 3, about 1 to about 3.8, about 1.2 to about 3.5, about 1.5 to about 3, about 1.5 to about 2.5, or about 1 to about 2.

In some embodiments, the first block can be prepared from one or more monomer units and have a molecular weight ($M_n$) in the range of about 20 kDa to about 80 kDa and a degree of polymerization in the range of about 20 to about 400. In some embodiments, the first block molecular weight ($M_n$) is in the range of about 25 kDa to about 60 kDa, or about 30 kDa to about 55 kDa, about 30 kDa to about 50 kDa, or about 30 kDa to about 40 kDa, and the like. In some embodiments, the first block degree of polymerization is in the range of about 30 to about 350, about 50 to about 300, about 70 to about 250, about 80 to about 240, about 100 to about 200, and the like.

In some embodiments, the second block can be prepared from one or more monomer units, and can have a molecular weight ($M_n$) in the range of about 1 kDa to about 80 kDa and a degree of polymerization in the range of about 3 to about 500. In some embodiments, the second block molecular weight ($M_n$) is in the range of about 10 kDa to about 70 kDa, about 15 kDa to about 65 kDa, about 20 kDa to about 60 kDa, about 25 kDa to about 55 kDa, about 30 kDa to about 50 kDa, about 35 kDa to about 45 kDa, about 5 kDa to about 15 kDa, and the like. In some embodiments, the second block degree of polymerization is in the range of about 10 to about 500, about 12 to about 450, 20 to about 400, about 25 to about 350, about 50 to about 300, about 100 to about 250, about 150 to about 200, about 5 to about 50, about 5 to about 20, and the like.

It will be appreciated that RAFT polymerization is generally known in the art. Suitable reagents, monomers, and conditions for RAFT polymerization previously investigated can be used in the copolymers, methods, and compositions described herein, such as those described in U.S. Pat. Nos. 9,006,193, 9,464,300, and 9,476,063, the disclosures of each of which are incorporated by reference in their entirety. It will be appreciated that a variety of solvents can be used in the RAFT polymerization method steps and purification steps described herein. Suitable solvents include, but are not limited to, 2-Chloroethanol, Acetic Acid (Glacial), Acetone, Acetonitrile, Acetophenone, Aniline, Benzaldehyde, Benzyl Acetate, Carbon disulfide, Cyclohexane, Cyclohexanol, Di(ethylene glycol), Di(propylene glycol), Diacetone alcohol, Diethyl ether, Dimethylsulfoxide, Ethanol, Ethyl acetate, Ethylene glycol, Formaldehyde (37% solution), Formamide, Formic acid, Formic acid (96%), HexaneIsobutanol, Isopropanol, Isopropyl acetate, Isopropyl ether, m-Cresol, Methanol, Methyl acetate, Methyl ethyl ketone, Mineral Oil, N,N-Dimethylformamide, n-Butanol, n-Octane, n-Propanol, Propylene glycol, Pyridine, t-Butanol, Tetrahydrofuran, Trifluoroacetic acid, water, and the like, and combinations thereof.

Illustrative payloads for the polymer nanoparticle or nanostructure DNA delivery compositions described herein can include any one or a combination of compositions selected from the group comprising: nucleic acids (e.g., DNA or RNA), pDNA, oligodeoxyribonucleic acids (ODNs), dsDNA, ssDNA, antisense oligonucleotides, antisense RNA, siRNA, messenger RNA, guide RNA (e.g., small guide RNA), ribonucleoproteins, donor DNA strands used in the CRISPR/Cas9 system, and enzymes, such as CRISPR-associated enzymes, e.g., Cas9, enzymes used in other gene editing systems, such as ZFNs, custom designed homing endonucleases, TALENS systems, other gene editing endonucleases, and reverse transcriptase.

Other illustrative payloads include DNA constructs such as chimeric antigen receptor (CAR) constructs. CAR-T cells are T cells expressing chimeric antigen receptors (CARs). The CAR is a genetically engineered receptor that is designed to target a specific antigen, for example, a tumor antigen. This targeting can result in cytotoxicity against the tumor, for example, such that CAR-T cells expressing CARs can target and kill tumors via the specific tumor antigens. CARs can comprise a recognition region, e.g., a single chain fragment variable (scFv) region derived from an antibody for recognition and binding to the antigen expressed by the tumor, an activation signaling domain, e.g., the CD3ζ chain of T cells can serve as a T cell activation signal in CARs, and a co-stimulation domain (e.g., CD137, CD28 or CD134) to achieve prolonged activation of T cells in vivo. In some aspects, CARs are large DNA constructs.

In another embodiment, the payload can be a nucleic acid construct (e.g., DNA or RNA) with a size selected from the group consisting of 3 kB or more, 3.1 kB or more, 3.2 kB or more, 3.3 kB or more, 3.4 KB or more, 3.5 kB or more, 3.6 kB or more, 3.7 kB or more, 3.8 KB or more, 3.9 kB or more, 4 kB or more, 4.1 kB or more, 4.2 kB or more, 4.3 kB or more, 4.4 KB or more, 4.5 KB or more, 4.6 kB or more, 4.7 kB or more, 4.8 kB or more, 4.9 KB or more, 5 kB or more, 5.1 kB or more, 5.2 kB or more, 5.3 kB or more, 5.4 kB or more, 5.5 kB or more, 5.6 kB or more, 5.7 KB or more, 5.8 kB or more, 5.9 kB or more, 6 kB or more, 6.1 kB or more, 6.2 kB or more, 6.3 kB or more, 6.4 kB or more, 6.5 kB or more, 6.6 kB or more, 6.7 kB or more, 6.8 KB or more, 6.9 kB or more, 7 KB or more, 7.1 kB or more, 7.2 kB or more, 7.3 kB or more, 7.4 KB or more, 7.5 KB or more, 7.6 kB or more, 7.7 KB or more, 7.8 KB or more, 7.9 KB or more, 8 kB or more, 8.1 kB or more, 8.2 kB or more, 8.3 kB or more, 8.4 KB or more, and 8.5 kB or more.

In various embodiments, the payload can be any one or more of the components of the CRISPR RNP system including a CRISPR-associated enzyme (e.g., Cas9), a short guide RNA (sgRNA), and a donor DNA strand. In an embodiment where the payload comprises Cas9, Cas9 can be fused to a deaminase. In yet another embodiment, the payload can comprise an sgRNA used for targeting an enzyme to a specific genomic sequence. In another aspect, the targeted enzyme can be a CRISPR-associated enzyme. In another illustrative aspect, the payload can comprise one molecule each of CRISPR/Cas9, an sgRNA, and a donor DNA strand in the polymer nanoparticle or DNA nanostructure delivery compositions described herein. In another embodiment, the payloads can be nucleic acids used for homology directed repair or as transposable elements. In yet another embodiment, the payloads can be any of the payloads described herein in the form of a plasmid construct.

In one aspect, the DNA nanostructure delivery composition described herein can encapsulate a payload that is used for gene editing. In one aspect, the CRISPR/Cas9 system can be the payload and can be used for gene editing. In another embodiment, another gene editing system can be the payload, such as ZFNs, custom designed homing endonucleases, and TALENS systems. In the embodiment where the CRISPR/Cas9 system is the payload, the Cas9 endonuclease is capable of introducing a double strand break into a DNA target sequence. In this aspect, the Cas9 endonuclease is guided by the guide polynucleotide (e.g., sgRNA) to recognize and optionally introduce a double strand break at a specific target site into the genome of a cell. In this illustrative embodiment, the Cas9 endonuclease can unwind the DNA duplex in close proximity to the genomic target site and can cleave both target DNA strands upon recognition of a target sequence by a guide polynucleotide (e.g., sgRNA), but only if the correct protospacer-adjacent motif (PAM) is approximately oriented at the 3' end of the target. In this embodiment, the donor DNA strand can then be incorporated into the genomic target site. The CRISPR/Cas9 system for gene editing is well-known in the art.

In another illustrative embodiment, the payload may include DNA segments that serve as nuclear localization signals, enhancing nuclear delivery of the polymer nanoparticles (e.g., RAFT copolymers) or DNA nanostructure delivery compositions upon endosomal escape. In another aspect, the payload may include a nucleotide sequence designed to bind as an aptamer to endosomal receptors, enhancing intracellular trafficking of the polymer nanoparticles (e.g., RAFT copolymers) or DNA nanostructure delivery compositions.

In one illustrative aspect, a DNA nanostructure delivery composition (e.g., DNA origami) is provided to package the Cas9 protein, the sgRNA and the single stranded donor DNA strand together in one nanostructure to ensure co-delivery of all the components to a particular location at the same time. In this embodiment, the single stranded nature of the sgRNA and the donor DNA strand can be used to convert these components into constitutive parts of the DNA nanostructure delivery composition (e.g., the DNA origami structure) such that they get delivered together and dissociate at the same time from the DNA nanostructure delivery composition upon reaching the target site (e.g., a target cell). In this embodiment, the DNA nanostructure delivery composition can deliver either a plasmid or the ribonucleoprotein (RNP) form of CRISPR/Cas 9.

In one embodiment, a method for gene therapy is provided. In one aspect, the method comprises administering to a patient a DNA nanostructure delivery composition comprising i) a single stranded DNA scaffold and ii) one or more oligonucleotides that bind through complementary base pairing with a segment of the DNA scaffold, wherein the one or more oligonucleotides cause the DNA scaffold to fold, and wherein the composition comprises more than one payload for delivery or a nucleic acid construct payload of 3 kB or more. In another embodiment, the method comprises administering to the patient a polymer nanoparticle composition, such as a RAFT copolymer composition. In another embodiment, a method for targeting a DNA nanostructure delivery composition to cells of a patient is provided. The method comprises administering to the patient i) a single stranded DNA scaffold and ii) one or more oligonucleotides that bind through complementary base pairing with a segment of the DNA scaffold, wherein the one or more oligonucleotides cause the DNA scaffold to fold, wherein the composition comprises more than one payload for delivery or a nucleic acid construct payload of 3 kB or more, and wherein the DNA nanostructure comprises a targeting component for targeting to the cells of the patient. In yet another embodiment, the targeting method comprises administering to the patient a polymer nanoparticle composition, such as a RAFT copolymer composition.

In one embodiment, the compositions described herein may be formulated as pharmaceutical compositions for parenteral or topical administration. Such pharmaceutical compositions and processes for making the same are known in the art for both humans and non-human mammals. See, e.g., REMINGTON: THE SCIENCE AND PRACTICE OF PHARMACY, (1995) A. Gennaro, et al., eds., 19$^{th}$ ed., Mack Publishing Co. Additional active ingredients may be included in the compositions.

In one aspect, the polymer nanoparticle composition or the DNA nanostructure delivery composition may be administered, for example, directly into the blood stream of a patient, into muscle, into an internal organ, or can be administered in a topical formulation. In various embodiments, suitable routes for such parenteral administration include intravenous, intraarterial, intraperitoneal, intrathecal, epidural, intracerebroventricular, intraurethral, intrasternal, intracranial, intratumoral, intramuscular and subcutaneous delivery. In one embodiment, means for parenteral administration include needle (including microneedle) injectors, needle-free injectors and infusion techniques.

In one illustrative aspect, parenteral formulations are typically aqueous solutions which may contain carriers or excipients such as salts, carbohydrates and buffering agents (preferably at a pH of from 3 to 9), but they may be more suitably formulated as a sterile non-aqueous solution or as a dried form to be used in conjunction with a suitable vehicle such as sterile, pyrogen-free water or sterile saline. The preparation under sterile conditions, by lyophilization to produce a sterile lyophilized powder for a parenteral formulation, may readily be accomplished using standard pharmaceutical techniques well-known to those skilled in the art. In one embodiment, the solubility of the composition used in the preparation of a parenteral formulation may be increased by the use of appropriate formulation techniques, such as the incorporation of solubility-enhancing agents.

In one illustrative embodiment, pharmaceutical compositions for parenteral administration comprise: a) a pharmaceutically active amount of the polymer nanoparticle composition or the DNA nanostructure delivery composition; b) a pharmaceutically acceptable pH buffering agent to provide a pH in the range of about pH 4.5 to about pH 9; c) an ionic strength modifying agent in the concentration range of about 0 to about 300 millimolar; and d) water soluble viscosity modifying agent in the concentration range of about 0.25% to about 10% total formula weight or any combinations of a), b), c) and d) are provided.

In various illustrative embodiments, the pH buffering agents for use in the compositions and methods herein described are those agents known to the skilled artisan and include, for example, acetate, borate, carbonate, citrate, and phosphate buffers, as well as hydrochloric acid, sodium hydroxide, magnesium oxide, monopotassium phosphate, bicarbonate, ammonia, carbonic acid, hydrochloric acid, sodium citrate, citric acid, acetic acid, disodium hydrogen phosphate, borax, boric acid, sodium hydroxide, diethyl barbituric acid, and proteins, as well as various biological buffers, for example, TAPS, Bicine, Tris, Tricine, HEPES, TES, MOPS, PIPES, cacodylate, or MES.

In another illustrative embodiment, the ionic strength modulating agents include those agents known in the art, for example, glycerin, propylene glycol, mannitol, glucose, dextrose, sorbitol, sodium chloride, potassium chloride, and other electrolytes.

Useful viscosity modulating agents include but are not limited to, ionic and nonionic water soluble polymers; crosslinked acrylic acid polymers such as the "carbomer" family of polymers, e.g., carboxypolyalkylenes that may be obtained commercially under the Carbopol® trademark; hydrophilic polymers such as polyethylene oxides, polyoxyethylene-polyoxypropylene copolymers, and polyvinylalcohol; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; gums such as tragacanth and xanthan gum; sodium alginate; gelatin, hyaluronic acid and salts thereof, chitosans, gellans or any combination thereof. Typically, non-acidic viscosity enhancing agents, such as a neutral or a basic agent are employed in order to facilitate achieving the desired pH of the formulation.

In one embodiment, the solubility of the compositions described herein used in the preparation of a parenteral formulation may be increased by the use of appropriate formulation techniques, such as the incorporation of solubility-enhancing agents.

In other embodiments, the compositions described herein may be administered topically. A variety of dose forms and bases can be applied to the topical preparations, such as an ointment, cream, gel, gel ointment, plaster (e.g. cataplasm, poultice), solution, powders, and the like. These preparations may be prepared by any conventional method with conventional pharmaceutically acceptable carriers or diluents as described below.

For example, vaseline, higher alcohols, beeswax, vegetable oils, polyethylene glycol, etc. can be used. In the preparation of a cream formulation, fats and oils, waxes, higher fatty acids, higher alcohols, fatty acid esters, purified water, emulsifying agents etc. can be used. In the preparation of gel formulations, conventional gelling materials such as polyacrylates (e.g. sodium polyacrylate), hydroxypropyl cellulose, hydroxypropyl methyl cellulose, polyvinyl alcohol, polyvinylpyrrolidone, purified water, lower alcohols, polyhydric alcohols, polyethylene glycol, and the like are used. In the preparation of a gel ointment, an emulsifying agent (preferably nonionic surfactants), an oily substance (e.g. liquid paraffin, triglycerides, and the like), etc. are used in addition to the gelling materials as mentioned above. A plaster such as cataplasm or poultice can be prepared by spreading a gel preparation as mentioned above onto a support (e.g. fabrics, non-woven fabrics). In addition to the above-mentioned ingredients, paraffins, squalane, lanolin, cholesterol esters, higher fatty acid esters, and the like may optionally be used. Moreover, antioxidants such as BHA, BHT, propyl gallate, pyrogallol, tocopherol, etc. may also be incorporated. In addition to the above-mentioned preparations and components, there may optionally be used any other conventional formulations for incorporation with any other additives.

In various embodiments, the dosage of the polymer nanoparticle composition or the DNA nanostructure delivery composition can vary significantly depending on the patient condition, or the disease state being treated, the route of administration and tissue distribution, and the possibility of co-usage of other therapeutic treatments. The effective amount to be administered to a patient is based on body surface area, patient weight or mass, and physician assessment of patient condition.

The polymer nanoparticle composition or the DNA nanostructure delivery composition can be administered to a patient with a disease or a disorder selected from the group consisting of cancer, a muscular disorder, a pulmonary disorder, a skin disorder, a neurological disease, neurofibromatosis 1 (NF1), and a hemoglobinopathy. In one embodiment, the cancer is selected from the group consisting of lung cancer, bone cancer, pancreatic cancer, skin cancer, uterine cancer, ovarian cancer, endometrial cancer, rectal cancer, stomach cancer, colon cancer, breast cancer, cancer of the esophagus, cancer of the endocrine system, prostate cancer, leukemia, lymphoma, mesothelioma, cancer of the bladder, cancer of the kidney, neoplasms of the central nervous system, brain cancer, and adenocarcinoma. In another embodiment, the skin disorder is a *Staphlococcus aureus* infection. In yet another embodiment, the muscular disorder is muscular dystrophy (e.g., Duchenne Muscular Dystrophy). In still another embodiment, the polymer nanoparticle composition and the DNA nanostructure delivery composition are not cytotoxic to the cells of the patient. In another embodiment, the gene therapy may result in the inactivation of a pathogen (i.e., a microorganism) rather than altering the genome of the patient.

In another embodiment, a method is provided comprising synthesizing a diverse set of non-viral gene delivery compositions, wherein each non-viral gene delivery composition differs from each other non-viral gene delivery composition of the diverse set with respect to at least one of a set of composition characteristics, simultaneously testing one or more quality attributes of each of the non-viral gene delivery composition of the diverse set, and creating, using results of the testing, a predictive model that correlates the composition characteristics with the quality attributes. In this embodiment, the composition characteristics can comprise one or more of molecular weight, degree of branching, number of ionizable groups, core-to-corona molecular weight ratio, hydrophilicity, hydrophobicity, propensity for aggregation, size, pKa, logP, and surface charge. In this embodiment, the quality attributes can comprise one or more of cytotoxicity, immunogenicity, transfection efficiency, zeta potential, size, pKa, logP, and loading efficiency. In this embodiment, the diverse set can comprises hundreds or thousands of non-viral gene delivery compositions. In this embodiment, each of the non-viral gene delivery compositions of the diverse set can be a DNA nanostructure delivery composition according to one of clauses 1-36 or 118-154 or a RAFT block copolymer according to one of clauses 118-127 above. above. In one embodiment of this method, high-throughput testing, and machine learning data analysis can accelerate the design-build-test-learn (DBTL) cycle for development of CRISPR-based therapeutics.

In some embodiments, the polymer nanoparticle composition or the DNA nanostructure delivery composition may be labelled to enhance downstream separation. For example, this may include covalently bonding the polymer nanoparticle composition or the DNA nanostructure delivery composition to a magnetic nanoparticle (e.g., superparamagnetic iron oxide), to polyhistidine tags for metal ion chromatography, and/or to fluorescent labels for fluorescent assisted separation (such as with FACS). The labels may be used to track the polymer nanoparticle composition or the DNA nanostructure delivery composition in vivo. Possible "endpoints" include, but are not limited to, quantitative presence in various physiological tissue, post administration, measured via, for example, fluorescence.

In the embodiment where labels are used, the labels allow for rapid in vivo screening of many non-viral nanoparticle variants with parallel determination of quantitative biodistribution, and rapid in vitro screening of many non-viral nanoparticle variants for stability, cytotoxicity, immunogenicity, and efficacy. This embodiment allows for the construction of a large library of non-viral delivery vehicles that can be drawn from for use as delivery vehicles for genetic medicines, including gene therapies, genetic vaccines, gene editing, and gene regulators.

In some illustrative embodiments, a large library of similar, but unique polymer nanoparticle compositions or the DNA nanostructure delivery compositions may be constructed for use in a high-throughput screening process to identify targeting components that bind to specific targets. This rapid screening platform can quickly determine an effective targeting molecule that can be used for targeted delivery to a specific cell or tissue, or for use as a neutralizing molecule for a pathogen.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

While certain illustrative embodiments have been described in detail in the drawings and the foregoing description, such an illustration and description is to be considered as exemplary and not restrictive in character, it being understood that only illustrative embodiments have been shown and described and that all changes and modifications that come within the spirit of the disclosure are desired to be protected. There exist a plurality of advantages of the present disclosure arising from the various features of the apparatus, systems, and methods described herein. It will be noted that alternative embodiments of the apparatus, systems, and methods of the present disclosure may not include all of the features described, yet still benefit from at least some of the advantages of such features. Those of ordinary skill in the art may readily devise their own implementations of the apparatus, systems, and methods that incorporate one or more of the features of the present disclosure.

While the concepts of the present disclosure are susceptible to various modifications and alternative forms, specific embodiments thereof have been shown by way of example in the appended drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure.

EXAMPLE 1

DNA Nanostructure Delivery Compositions

Figure 5A:
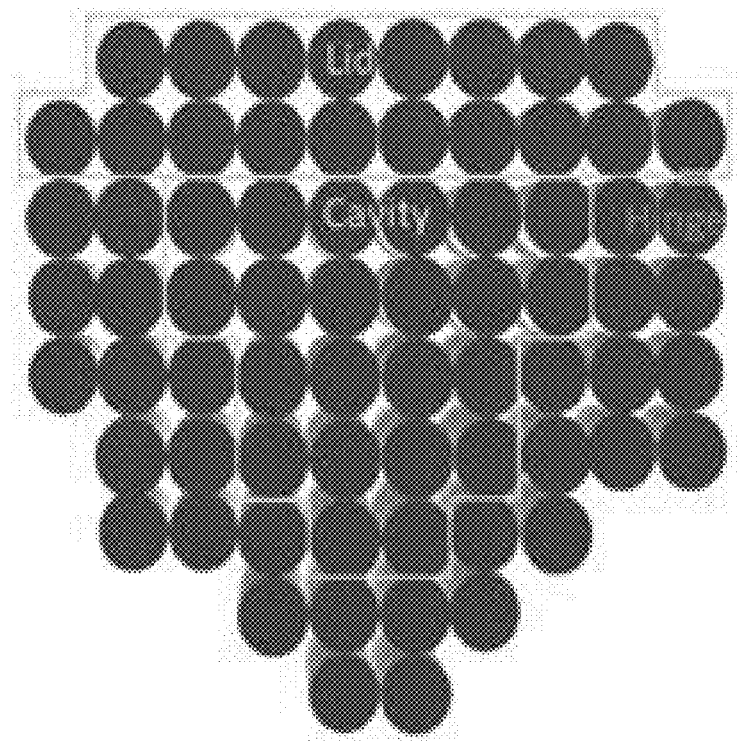
FIG. 5A shows a side view of a DNA nanostructure delivery composition with a capsule with lid, designed to have a height of 23.4 nm and a width of 26 nm.
Figure 5B:
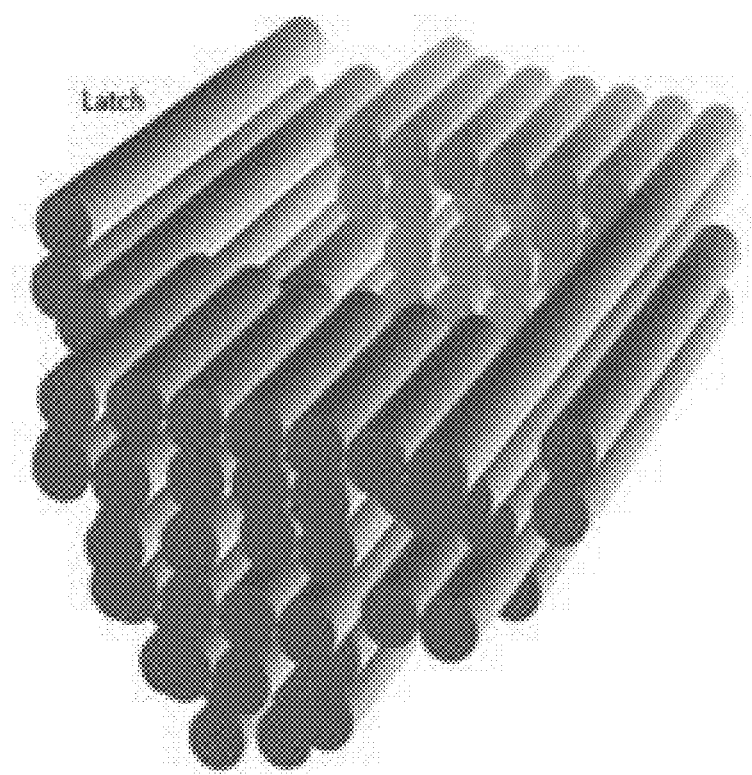
FIG. 5B shows the transverse view of the design, with a length of 60 nm. The cavity has dimensions of 13 nm in height and 15.6 nm in width and is designed to encapsulate CRISPR RNP. The cylindrical structures represent helix "bundles".

An example of the DNA nanostructure delivery compositions uses nucleic acids themselves (the DNA origami structure) to encapsulate the CRISPR RNP construct. A single-stranded DNA scaffold is used and is grown and isolated in the M13 phage and combined with oligonucleotide staples that pair with the scaffold at pre-programed segments to form highly controlled and tuned three-dimensional structures. Moreover, computer aided design (CAD) tools can predict the sequences in oligonucleotide staples necessary to produce highly engineered nanostructures, resulting in the possibility of a virtual library of nanoparticles from which to begin a custom delivery vehicle design. As gene delivery vehicles, these DNA nanostructures offer significant advantages, including precise tuning of the size and shape of the structure to match the cargo. These nanoparticles can be functionalized with nucleic acid aptamers for targeted binding to specific cell and tissue types. The inventors have designed a novel DNA origami delivery platform customized for the delivery, for example, of CRISPR RNP (FIG. 5). Loading efficiency can be further increased by strategically incorporating overhangs in the origami sequence to bind the guide and repair DNA constructs within the encapsulating nanostructure itself. Finally, highly specific targeted delivery can be achieved with the incorporation of "lock and key" mechanisms into the nucleotide sequence as discussed herein. DNA scaffolds can be produced in high yield using cell density fermentation of *Escherichia coli* libraries. Oligonucleotides used as the "staples" for the origami structure can be produced synthetically and then cloned in large numbers using PCR. To address delivery for CRISPR/Cas9 systems, two delivery vehicle platforms: polymer nanoparticles and DNA origami to encapsulate and deliver CRISPR RNPs have been developed. The processing steps for each platform include several critical processing parameters (CPPs) that can be tuned to produce desirable critical quality attributes (CQAs). For example, several desired CQA outputs include decreasing the cytotoxicity and immunogenicity of the delivery vehicles while enhancing their uptake by and subsequent transfection efficiency. The size, hydrophilicity and hydrophobicity, propensity for aggregation, and zeta potential of these delivery vehicles with and without their cargo can be characterized.

Then, a series of in vitro assays can be run in parallel to identify how changes in the CPPs affect cytotoxicity, immunogenicity, and transfection efficiency of the delivery vehicles. The inventors have established machine learning to analyze large data sets and build models which can be applied to the exploration of nanocarrier design spaces. This framework will be set up to build a suitability surface for optimization of the CQAs via a machine learning algorithm. This system will accelerate the design of nanocarriers capable of efficiently delivering CRISPR/Cas9 gene editing tools, for example, to cells.

DNA nanostructures can be used to encapsulate RNP, to demonstrate triggered release in cells in vitro, and to assess efficacy in vivo using an animal model. The design shown in FIG. 5 can be used to encapsulate a Cas9/gRNA RNP that is delivered to a HEK-293 reporter cell in vitro. The cell can be modified with a GFP reporter with a stop codon preceding it. The gRNA is targeted to disrupt the stop codon, leading to a GFP signal indicating successful gene editing. In vivo, the nanostructure can be tagged with a Cy5 red fluorescent label and tracked using the IVIS to determine biodistribution. These DNA origami-based delivery vehicles may provide precision editing of genes, specificity and high efficiency.

EXAMPLE 2

DNA Nanostructure Fabrication, Purification, and Characterization

DNA nanostructures were fabricated, loaded with CRISPR/Cas9 and coated with polyethylene glycol (PEG)-Poly-L-Lysine to protect the structures from degradation and clearance in vivo and polyethylenimine (PEI) to enhance endosomal escape. The encapsulation of a CRISPR/Cas9 RNP in a DNA nanostructure with one-to-one precision (see FIG. 1E) demonstrates the unique capability of DNA nanostructures (e.g., DNA origami structures) to produce nanostructures with a high degree of predictability (i.e., fabricated structures looked exactly as designed) and structural control. Only one molecule of Cas9 RNP was encapsulated per structure. This is not possible with any other delivery vector currently available.

Figure 1E:
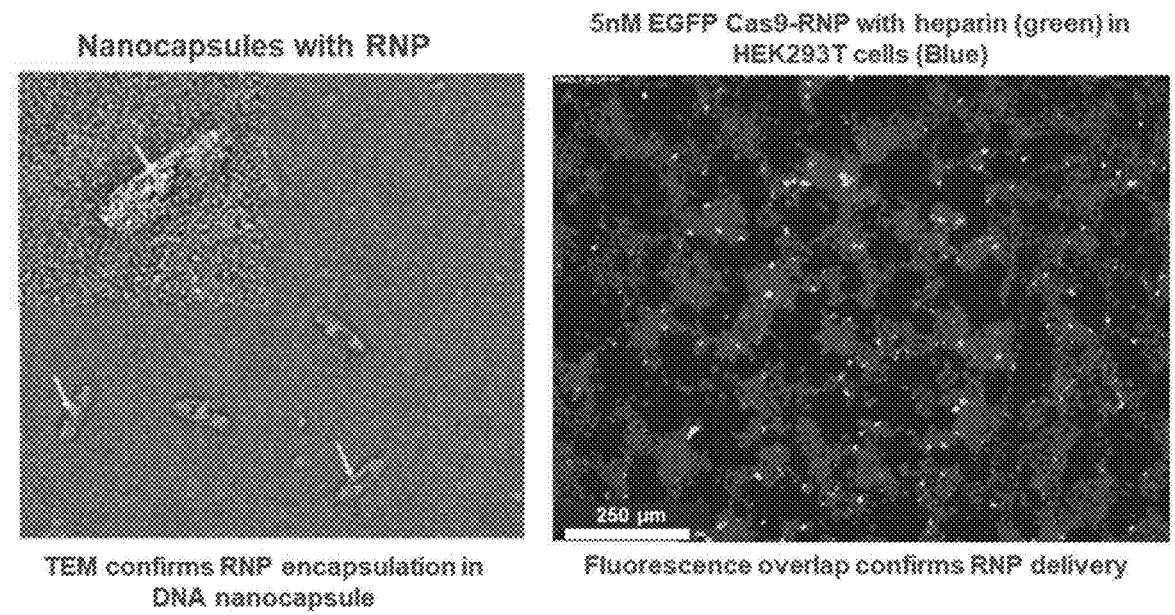
FIG. 1E shows a TEM image showing one to one encapsulation of Cas9 RNP (arrows) in the DNA nanostructure and uptake in HEK 293 cells.
Figure 1F:
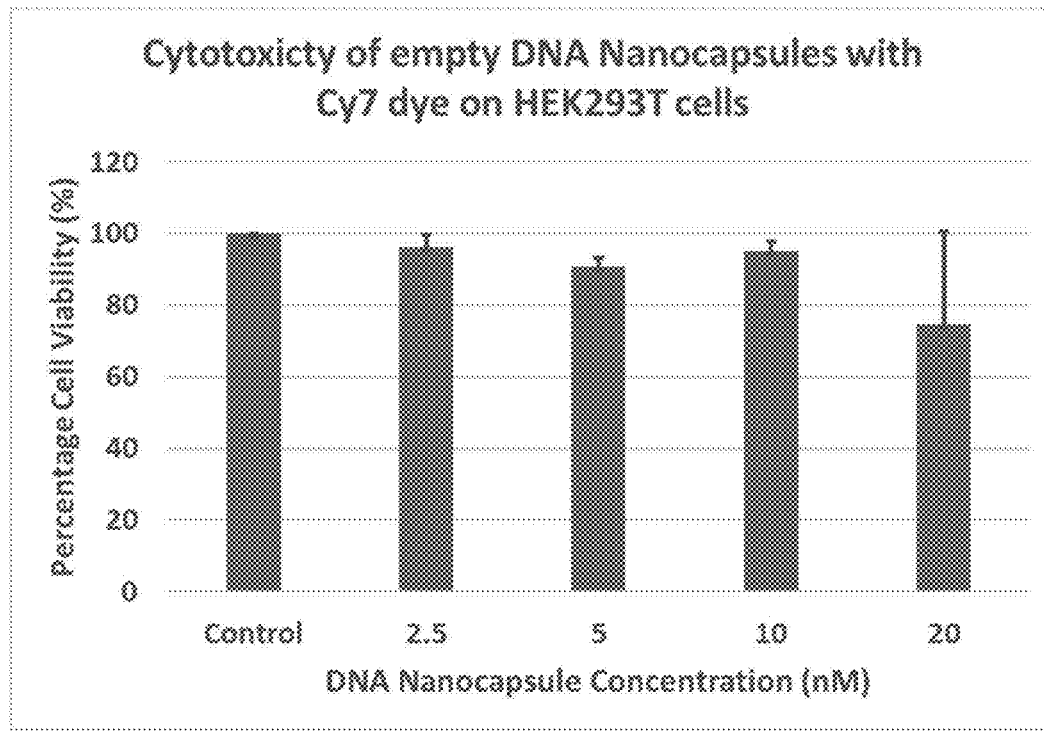
FIG. 1F shows results of an MTT assay to study cytotoxicity of the empty DNA nanostructure.

Delivery of the Cas9 RNP via closed DNA nanostructures to HEK 293 cells (FIG. 1E) was also demonstrated based on co-localization of fluorescence. Furthermore, the DNA nanostructures were folded and cuboid shaped DNA nanostructures were imaged (FIG. 1E). Cytotoxicity experiments (MTT assay) performed with empty DNA nanostructures showed that empty DNA nanostructures even up to 10 nM were not cytotoxic to HEK293 cells after 24 hours of incubation (FIG. 1F). Cell viability was relatively high (75%) even at 20 nM considering most transfections exposed cells to the DNA nanostructure treatment for <5 hours.

Figure 1G:
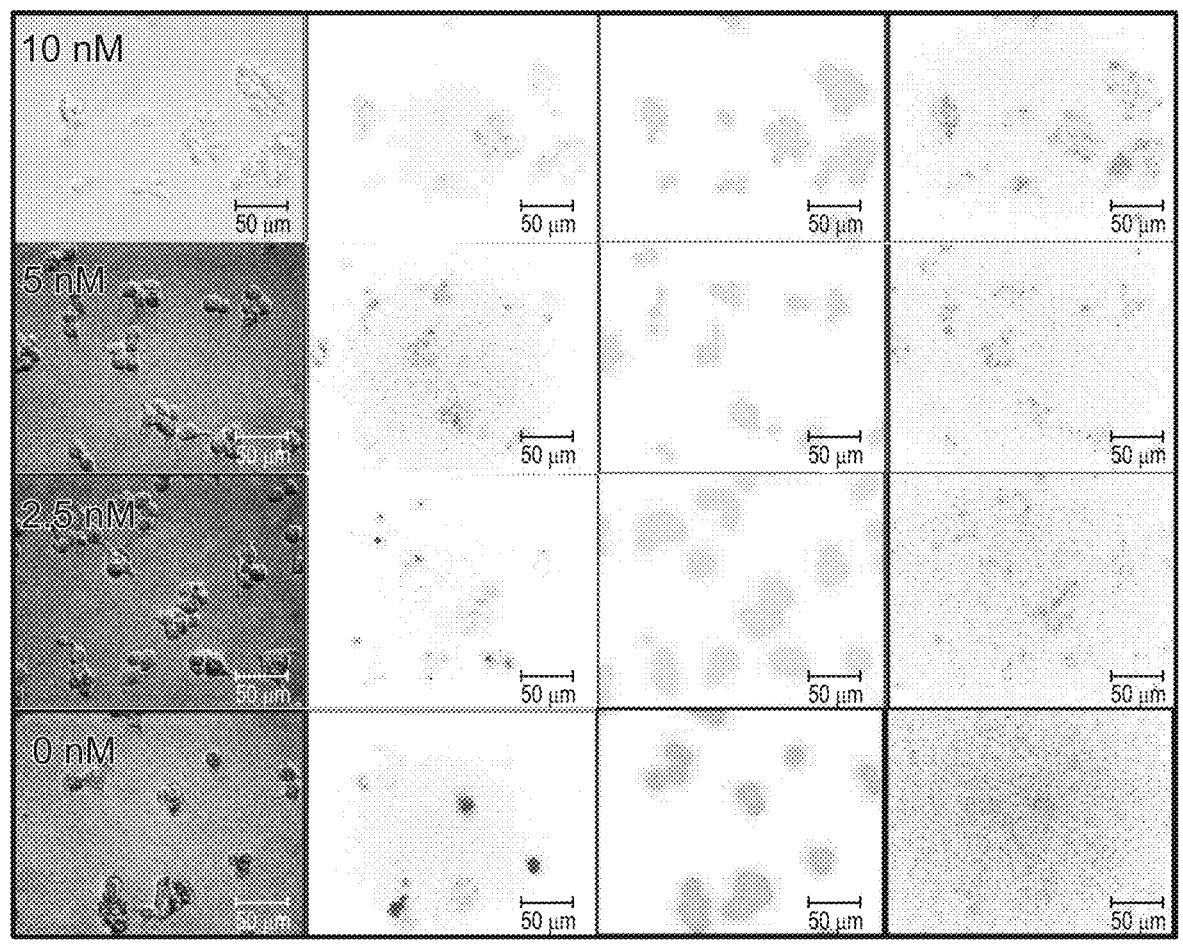
FIG. 1G and FIG. 1H show results demonstrating concentration dependent uptake of the DNA nanostructure and that EGFP Cas9 colocalizes with the cell nucleus indicating nuclear delivery.
Figure 1H:
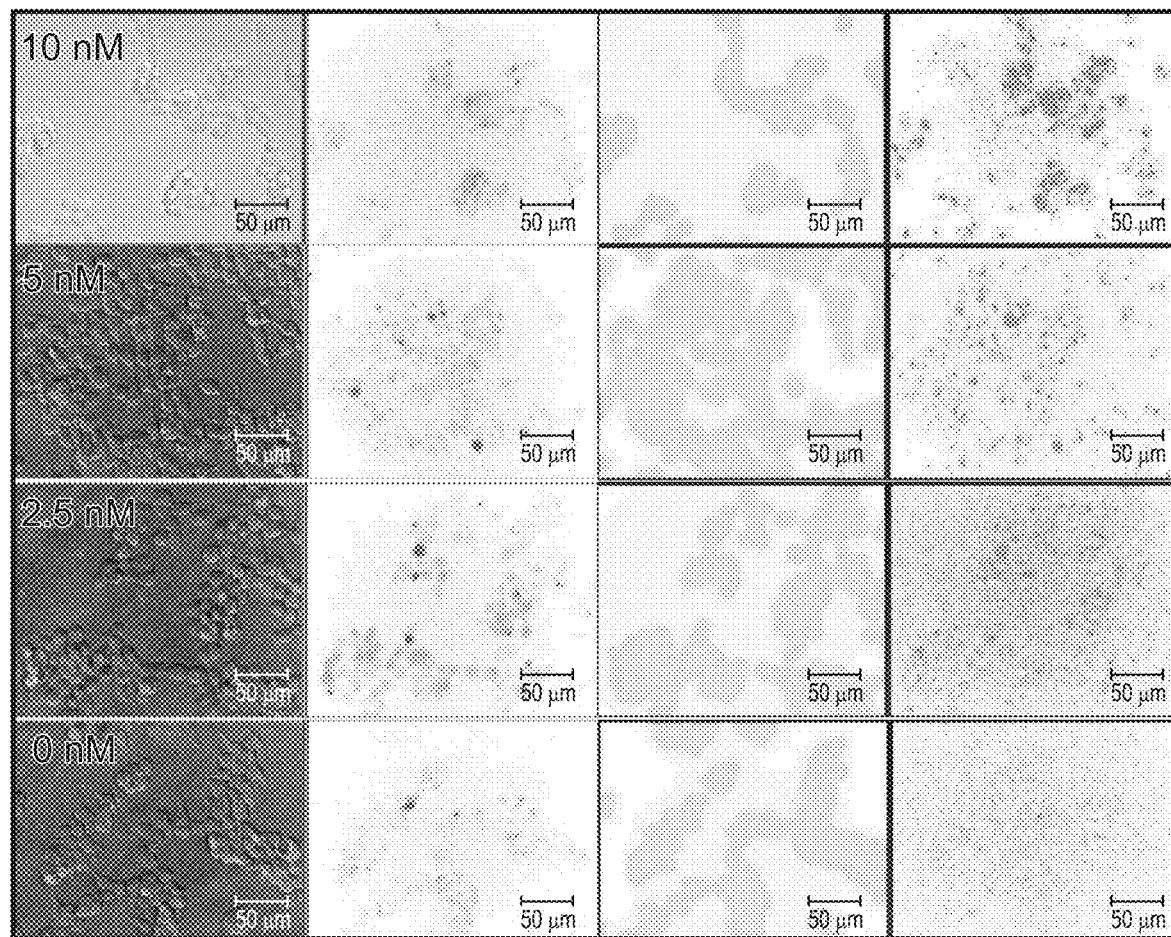

Concentration dependent uptake and colocalization with the nucleus was demonstrated by incubating empty and Cas9 RNP loaded DNA nanostructures with HEK293 cells (FIGS. 1G and 1H). The DNA nanostructure was labeled with Cy5, and the encapsulated Cas9 was EGFP labeled. This data showed that the cargo in the DNA nanostructures can be targeted to the nucleus to carry out gene editing tasks.

HDR-mediated gene editing experiments will use the same DNA nanostructures which in addition to having the CRISPR RNP also have two HDR donor DNA strand oligos per DNA nanostructure for an in vivo study. The DNA nanostructures will be labeled with Cy5.5 dye for biodistribution and toxicity analysis.

EXAMPLE 3

Raft Copolymers

Figure 2:
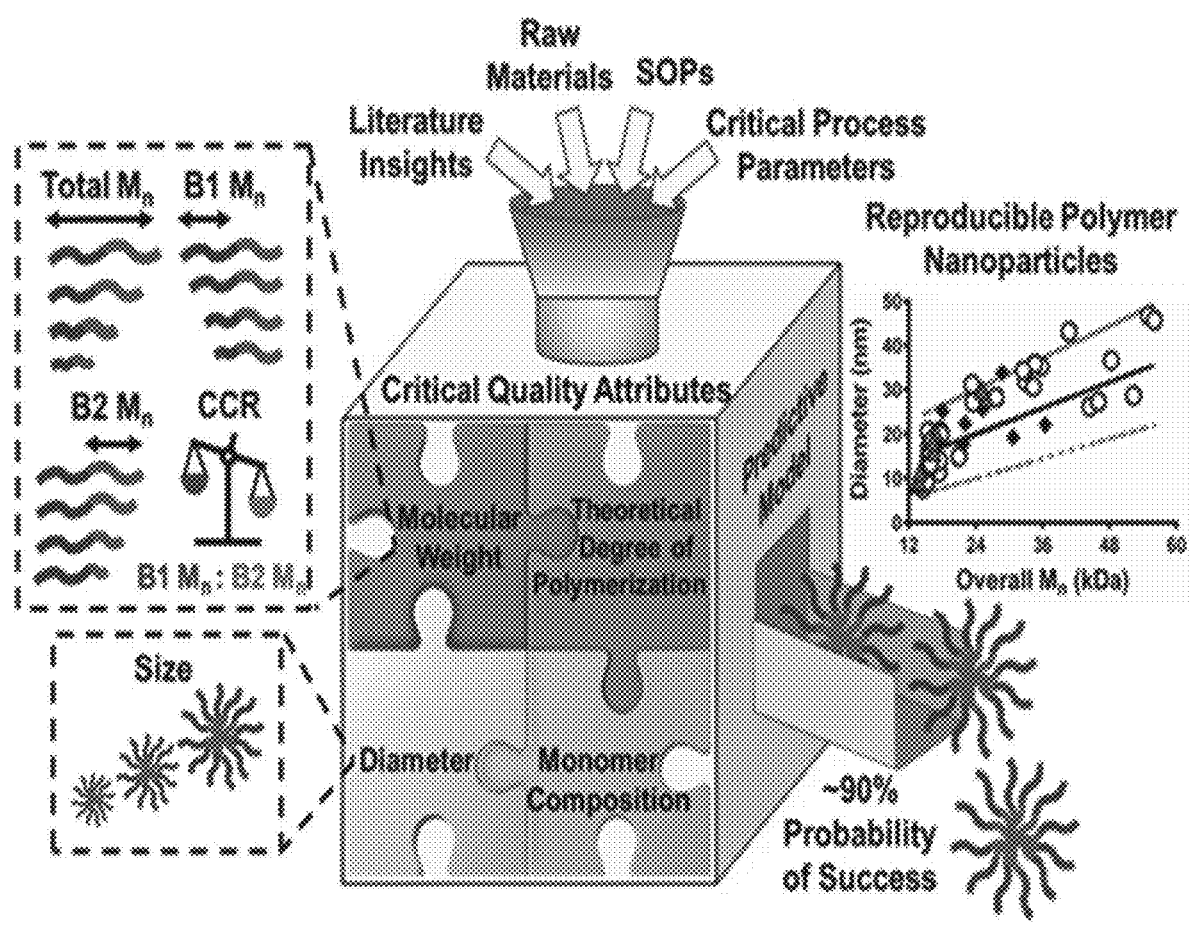
FIG. 2 shows a schematic of the input parameters for polymer nanoparticle synthesis and the highly tunable output characteristics.
Figure 3:
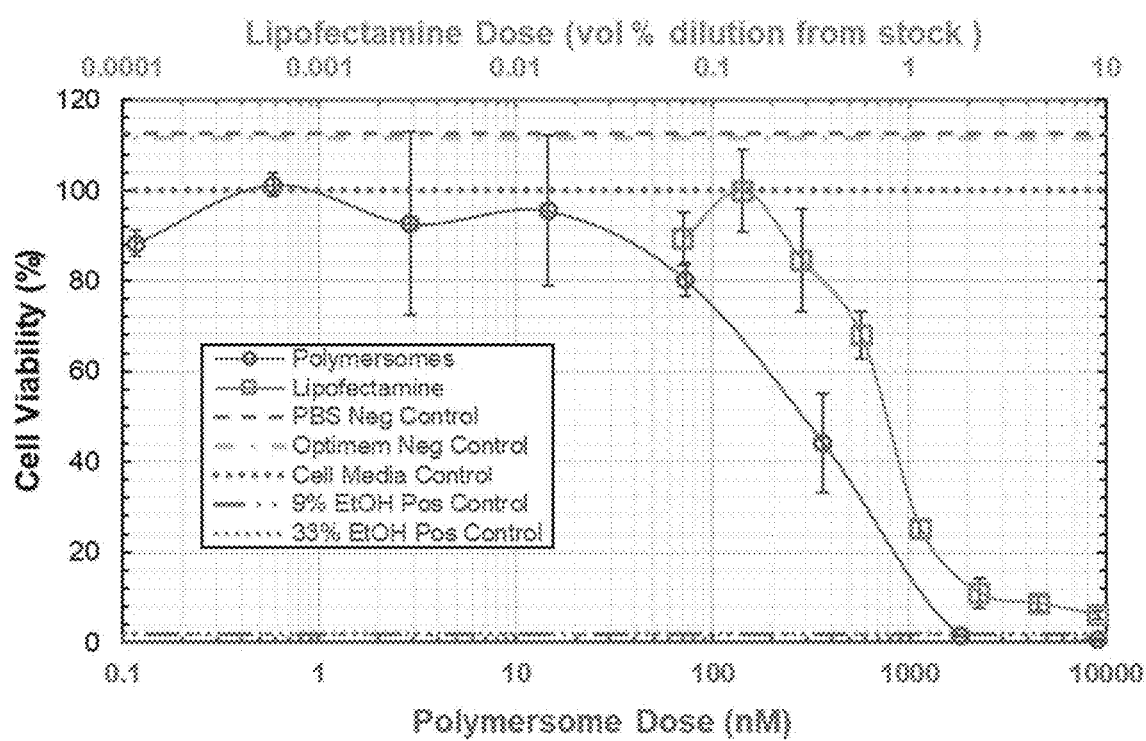
FIG. 3 shows the results of a cytotoxicity assay for polymer nanoparticle compositions.

The non-viral delivery vehicles needed for translation of gene editing treatments can be synthesized with repeatable, versatile and scalable methods to meet GMP requirements. For these reasons, lipid nanoparticles have been used for most non-viral nucleic acid delivery vehicles in clinical trials. Although polymer nanoparticles have been less commonly used for clinical nucleic acid delivery, polymer synthesis methods provide scalable manufacturing benefits in ways that cannot be matched by other biomaterials such as lipids. Recently, methods of producing cationic block copolymer nanoparticles using reversible-addition fragmentation chain transfer (RAFT) polymerization have been standardized to demonstrate rigor and reproducibility necessary for commercial scale nanocarrier production (FIG. 2). Given their robustness, versatility and sophistication, the RAFT copolymerization process is an attractive route for synthesizing non-viral delivery vehicle alternatives to AAVs. It has recently been demonstrated that these RAFT copolymers can be synthesized in multiplex, high-throughput arrays in multi-well plates. These methods are being used for the encapsulation and delivery of pDNA encoding for Cas9 and gRNA editing systems to somatic cell lines. As is the case with lipid nanoparticles, polymer nanoparticle delivery vehicles are designed using cationic polymers that form complexes with negatively charged nucleic acids and enhance interaction with the negative resting potential of the cellular membrane. However, the same positive surface charge may also lead to cytotoxicity in high enough doses. To address this concern, the inventors have conducted cytotoxicity assays (FIG. 3—see Example 4).

3A: Preparation of Raft Copolymers

Block 1 reagents were combined in a round bottom flask, purged with argon, and heated to 60° C. for 6 hours using a heating mantle. The reaction product was purified using four 80:20 pentane:ether precipitation washes and centrifugation cycles and dried in vacuo. The Block 1 product was used as the macroRAFT agent for Block 2, and the calculated reagent volumes (as calculated based on theoretical molecular weight information for Block 1) were combined in a round bottom for the Block 2 reaction. The reaction mixture was argon purged before being heated at 60° C. for 24 hours. The reaction product was purified using the same purification process and dried in vacuo. The resulting polymer was dialyzed in deionized water for 4 days with multiple water changes each day. Finally, the dialyzed material was lyophilized for 4 days and stored at room temperature for experimental use. Size was measured using a Malvern Zetasizer Nano. Molecular weights for Blocks 1 and 2 were measured, and molecular weight for Block 1 was measured internally using a DynaPro Plate Reader III. All molecular weights are reported in this example as number average molecular weight ($M_n$).

| Reagent | Purpose | Lot 0001 Amount | Lot 0002 Amount |
|---|---|---|---|
| Block 1 | | | |
| 2-dimethylaminoethyl acrylate (DMAEMA) | Monomer | 15999.6 mg | 32000.0 mg |
| (4-cyano-4-(((ethylthio)carbonothioyl)thio)pentanoic acid) (ECT) | Chain transfer agent | 76.9 mg | 153.7 mg |
| Azobisisobutyronitrile AIBN | Initiator | 9.5 mg | 19.05 mg |
| Dimethylformamide DMF | Solvent | 24131.1 mg | 48229.8 mg |
| Block 1 Reaction Yield | % Yield | 31.75% | 39.55% |
| Block 2 | | | |
| 2-dimethylaminoethyl acrylate (DMAEMA) | Monomer | 713.0 mg | 2110.6 mg |
| butyl methacrylate (BMA) | Monomer | 1934.4 mg | 5727.6 mg |
| propyl acrylic acid (PAA) | Monomer | 518.2 mg | 1540.1 mg |
| Block 1 macroRAFT agent, meaning ECT + DMAEMA. The ECT end groups (R & Z) were still present to perform their function, but they were on the end of the p(DMAEMA) polymer synthesized as block 1. For reference, here is ECT showing the R & Z groups on either side of the trithiocarbonyl group. | Macro Chain transfer agent | 1528.4 mg | 4526.2 mg |

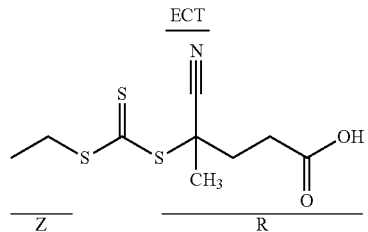

| | | | |
|---|---|---|---|
| Azobisisobutyronitrile AIBN | Initiator | 1.7 mg | 4.93 mg |
| Dimethylformamide DMF | Solvent | 7045.0 mg | 20828.8 mg |
| Block 2 Reaction Yield | % Yield | 73.33% | 70.99% |

Characterization Data

| Sample | Block 1 GPC Result (molecular weight, kDa) | Block 1 DynaPro Result (molar mass, kDa) | Overall Diblock GPC Result (molecular weight, kDa) | Zetasizer DLS Result Number Distribution (size, nm) | Size PDI (goal <0.3) | Zetasizer Zeta Potential Result (mV) |
|---|---|---|---|---|---|---|
| 3A-0001 | 22.0 | 19.8 | 29.3 | 44.3 | 0.085 | 20.6 |
| 3A 0002 | N/A | 27.1 | N/A | 45.8 | 0.053 | 18.9 |

DLS and Zeta Potential measurements and TEM Imaging Confirmed Similarity of Size, Surface Charge, and Morphology of two lots.

GPC Data was obtained using a TDA-305 Tetra Detector System by Malvern. Data acquisition and handling were made with OmniSec software.

Data were obtained under the following conditions:
SOLVENT Dimethyl formamide with 0.05 M LiBr
FLOW RATE 1.0 mL/min
INJECTION VOLUME 100 μL
COLUMN TEMPERATURE 60° C.
CONCENTRATION ~2.5 mg/mL
COLUMN Agilent Polargel Mixed M 7.8×300 mm 8 μm
RUN TIME 30 minutes Measured Degree of Polymerization Values for Option A:
Block 1: 140 (140 DMAEMAs)
Block 2: 52 (8 DMAEMAs, 6 PAAs, and 38 BMAs)

Approximate Percent Monomer Composition of Option A (using NMR):

Using Target Block 1 and Block 2 molecular weights of 30.2 kDa and 15.1 kDa, respectively, the following block compositions were calculated from proton NMR spectra:
Block 1=100% dimethylaminoethyl methacrylate
Block 2=~17% dimethylaminoethyl methacrylate, ~74% butyl methacrylate, and 9% propyl acrylic acid

3B: Functionalization of Raft Copolymer with Avidin Via EDC-NHS Chemistry

RAFT copolymers made using CTAs that contain at least one carboxyl terminal group were further functionalized with avidin as an example of the functionalization of the PNP with an amine containing molecule.

A RAFT copolymer (160 mg) prepared according to example 3A was transferred into a 50 ml conical tube and reconstituted in MES buffer at 8 mg/mL. The sample was sonicated for 30 minutes. EDC reagent (10.5 mg) and Sulfo-NHS(29.7 mg) was added to the polymer. The sample was incubated for 15 minutes at room temperature to allow the reaction to occur. The reaction volume was transferred to Amicon ultra-4 centrifuge tubes (MWCO 30 kDa). (Max 3.5 mL/Tube) and centrifuged at 4,000×g for 15 minutes. The filtrated was discarded and sterile PBS was added to the retentate to reconstitute to 8 mg/mL polymer. Avidin (36.9 mg) was added to the reaction and incubated for 15 minutes at room temperature. The sample was transferred to an amicon ultra-4 centrifuge tubes (MWCO 30 kDa). (Max 3.5 mL/Tube) and centrifuged at 4,000×g for 15 minutes. The filtrate was discarded and sterile PBS was added to the retentate to final concentration of 8 mg/mL polymer.

3C: Avidin Loading Quantification

An avidin stock solution was created at 205.8 µM by reconstituting 10 mg of avidin in 720 µL of PBS to prepare an Avidin calibration curve in triplicate. Dulbeccos PBS (322 µL) was added to wells A1-A3 of a 96 well plate. Stock Avidin (78 µL) was added to yield a 40 µM solution in wells A1-A3. Dulbeccos PBS (200 µL) was added to remaining wells of columns 1-3 and a 2:1 serial dilution was performed from first row of wells.

Avidin coated polymer (200 µL) was added to three wells of the same 96 well plate. Native polymer (no avidin) (200 µL) was added to three other wells of the same 96 well plate. The absorbance at 280 nm and 260 nm was read against the calibration curve. 100% loading efficiency is 27.3 M.

3D: Raft Copolymer Library

RAFT copolymers were prepared according to the general procedure provided in Example 3A above, and using a 96 well plate. All reagent amounts were determined according to the same method as described in Example 3A.

Briefly, Block 1 reagents were combined in wells of a polypropylene 96-well u-shaped bottom microplate (Greiner Bio-One) or in polypropylene Eppendorf microcentrifuge tubes (Sigma-Aldrich) and placed in a VWR 1400E Sheldon vacuum oven. A 20 mL glass vial was filled with approximately 10-15 mL of dimethylformamide, and the vial was placed in the oven to provide a source for atmosphere saturation. The oven was purged with argon at ~3 L/min for approximately 45 minutes, and heated to between 60° C. and 75° C. for 6 hours. Upon completion of the reaction, acetone was added to the wells or tubes to prevent polymer solidification and the wells or tubes were sealed and left at room temperature overnight. The next day, the reaction product solutions were transferred to 1.5 mL Eppendorf tubes (if necessary) and purified via four precipitation washes using an appropriate purification solvent solution (e.g., 80:20 pentane:ether, isopropyl alcohol, methanol, etc.) and centrifugation cycles and dried in vacuo. The Block 1 product was used as the macroRAFT agent for Block 2, and the calculated reagent volumes (as calculated based on theoretical molecular weight information for Block 1) were combined in either a polypropylene 96-well u-shaped bottom microplate (Greiner Bio-One) or in polypropylene Eppendorf microcentrifuge tubes (Sigma-Aldrich) for the Block 2 reaction. The reaction mixtures were placed in a VWR 1400E Sheldon vacuum oven, which was argon purged at ~3 L/min for approximately 45 minutes before being heated to between 60° C. and 75° C. for 24 hours. The reaction products were purified using the same purification process as used for Block 1 library materials and dried in vacuo. The resulting polymers were resuspended in either acetone or chloroform and aliquoted as needed for experimental use (these transfer solvents evaporated prior to material use), stored in a dry state at room temperature, or dissolved in deionized water, frozen, and lyophilized prior to experimental use. Size was measured using a Wyatt Technology DynaPro Plate Reader III. Molecular weights for Block 1 materials were measured using a DynaPro Plate Reader III. Nanoparticle sizes above the DynaPro Plate Reader III molar mass capability threshold prevented measurement of Block 2 molecular weights for these polymer libraries. All molecular weights for high-throughput polymer libraries are reported as weight average molecular weight ($M_w$).

Exemplary libraries were prepared according to the following table.

| Library # | Library Composition | Polymers in Library |
|---|---|---|
| 0001 | Diverse B1 + B2 p(DMAEMA)-b-p(DMAEMA-co-BMA-co-PAA) | p(DMAEMA)-b-p(DMAEMA-co-BMA-co-PAA) |
| 0002 | Uniform B1 + B2 p(DMAEMA)-b-p(DMAEMA-co-BMA-co-PAA) | p(DMAEMA)-b-p(DMAEMA-co-BMA-co-PAA) |
| 0003 | Uniform B1 + B2 p(DMAEMA)-b-p(DMAEMA-co-BMA) | p(DMAEMA)-b-p(DMAEMA-co-BMA) |
| 0004 | Uniform B1 + B2 Input of p(DMAEMA)-b-p(DMAEMA-co-BMA) | p(DMAEMA)-b-p(DMAEMA-co-BMA) |
| 0005 | Diverse B1 + B2 p(DMAEMA)-b-p(DMAEMA-co-BMA-co-EAA) | p(DMAEMA)-b-p(DMAEMA-co-BMA-co-EAA) |
| 0006 | Diverse p(DMAEMA)-b-p(HEMA) CTA:I = 1 | p(DMAEMA)-b-p(HEMA) |
| 0007 | Diverse p(DMAEMA)-b-p(HEMA) CTA:I = 5 | p(DMAEMA)-b-p(HEMA) |
| 0008 | Diverse p(DMAEMA)-b-p(HEMA) CTA:I = 10 | p(DMAEMA)-b-p(HEMA) |
| 0009 | QND Varying Monomer, CTA, Initiator, and CTA:I in Plate using DMF | p(DMAEMA)-b-p(MMA)<br>p(DMAEMA)-b-p(BMA)<br>p(DPAEMA)-b-p(MMA)<br>p(DPAEMA)-b-p(BMA)<br>p(MMA)-b-p(DMAEMA)<br>p(MMA)-b-p(DPAEMA)<br>p(BMA)-b-p(DMAEMA)<br>p(BMA)-b-p(DPAEMA) |
| 0010 | QND Varying Monomer, CTA, Initiator, and CTA:I in Plate using DMSO | p(DMAEMA)-b-p(MMA)<br>p(DMAEMA)-b-p(BMA)<br>p(DPAEMA)-b-p(MMA) |

-continued

| Library # | Library Composition | Polymers in Library |
|---|---|---|
| 0011 | QND Varying Monomer, CTA, Initiator, and CTA:I in Tubes using DMF | p(DPAEMA)-b-p(BMA)<br>p(MMA)-b-p(DMAEMA)<br>p(MMA)-b-p(DPAEMA)<br>p(BMA)-b-p(DMAEMA)<br>p(BMA)-b-p(DPAEMA)<br>p(DMAEMA)-b-p(MMA)<br>p(DMAEMA)-b-p(BMA)<br>p(DPAEMA)-b-p(MMA)<br>p(DPAEMA)-b-p(BMA)<br>p(MMA)-b-p(DMAEMA)<br>p(MMA)-b-p(DPAEMA)<br>p(BMA)-b-p(DMAEMA)<br>p(BMA)-b-p(DPAEMA) |

Figure 6:
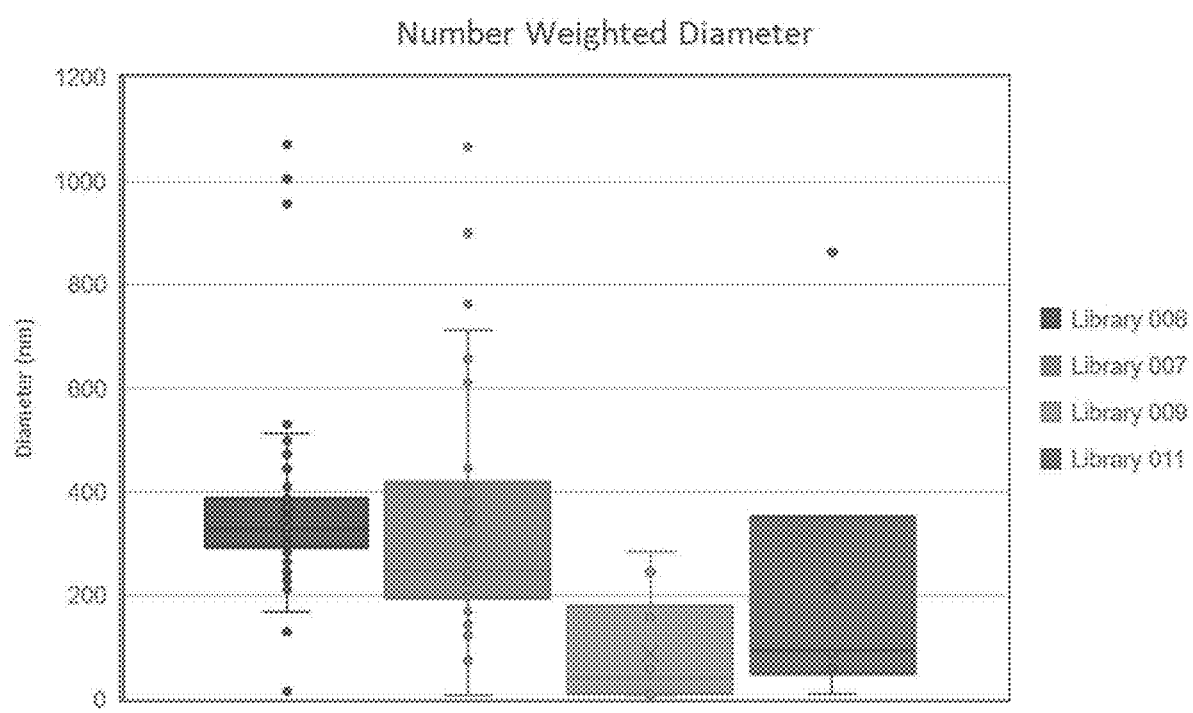
FIG. 6 is a chart showing polymer library size (diameter) data for Libraries 0006 (left most bar), 0007 (left-center bar), 0009 (right-center bar), and 0011 (right most bar) prepared as described herein.
Figure 7A:
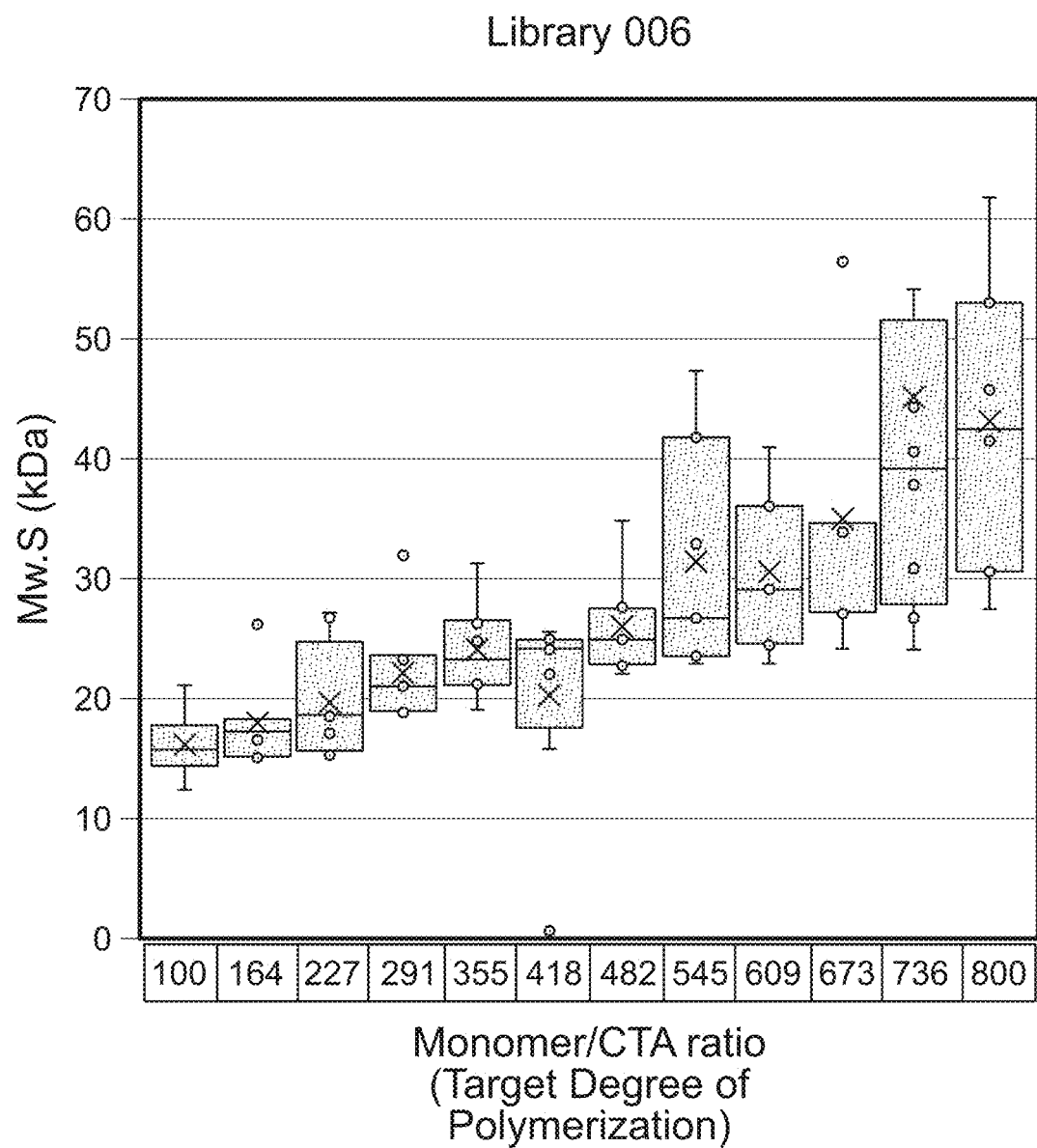
FIG. 7A-C are charts showing polymer Library Block 1 Molecular Weight (Mw) Data for Block 12 of Libraries 0006 (FIG. 7A), 0007 (FIG. 7B), and 0008 (FIG. 7C) prepared as described herein and measured as weight average molecular weight.
Figure 7B:
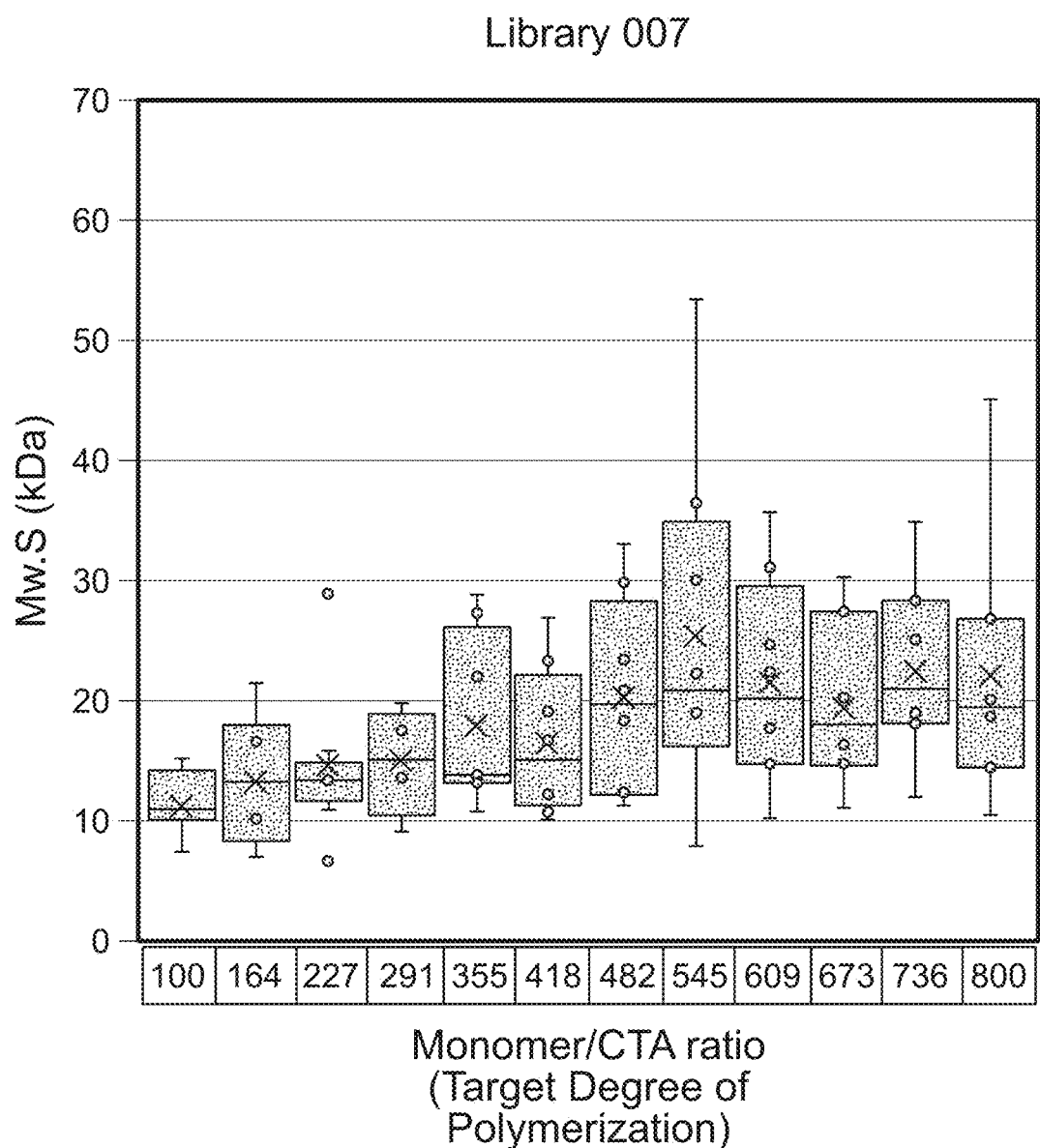
Figure 7C:
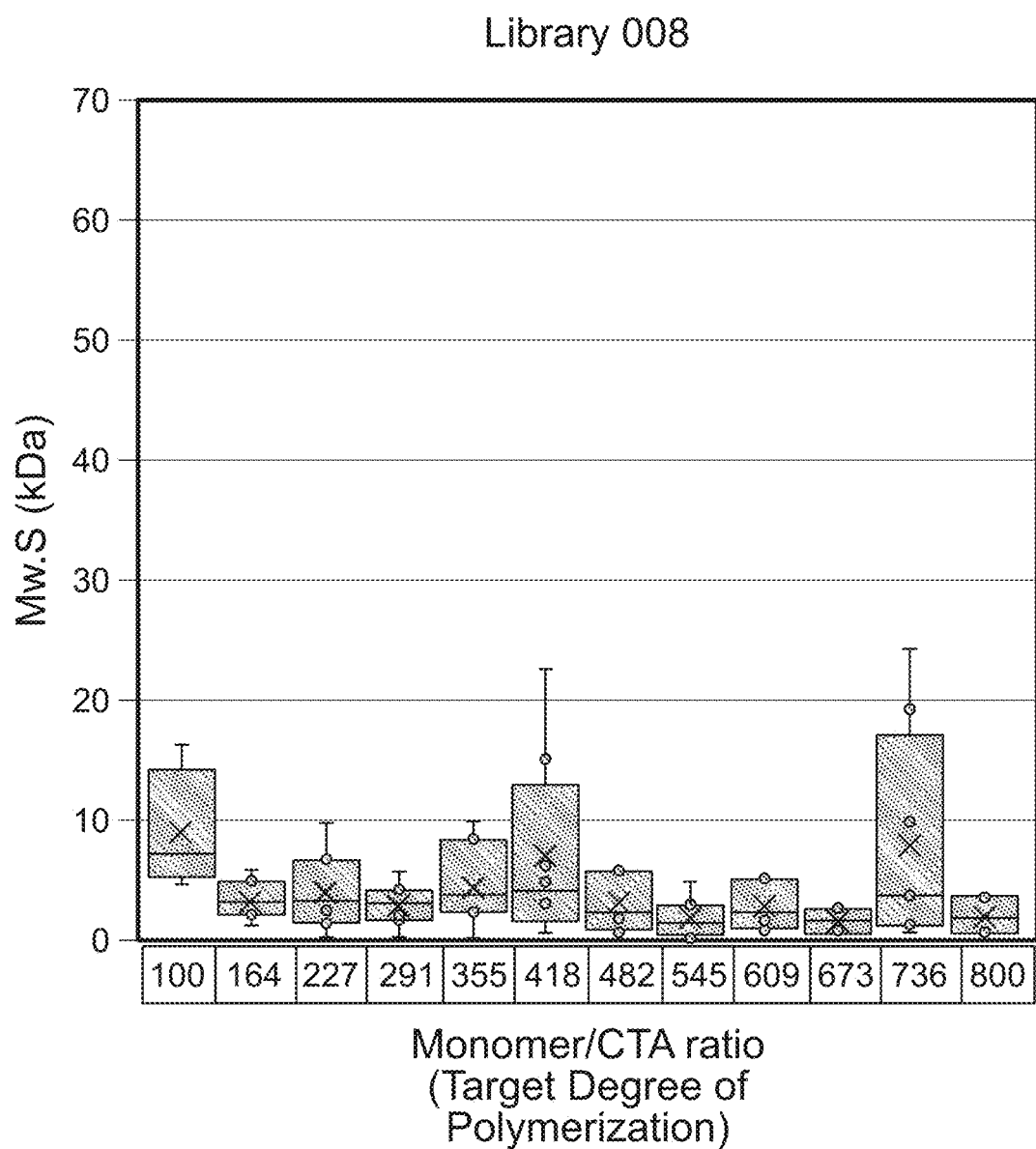

Polymer library size (diameter) data is provided for Libraries 0006, 0007, 0009, and 0011 in FIG. 6. Diameter data is calculated as follows:

$$d_{num\ wtd} = \sum d_i x_i$$

where $d_i$ = diameter of peak $i$
$x_i$ = number weighted contribution of peak $i$ Polymer Library Block 1 Molecular Weight (Mw) Data for libraries 0006, 0007, 0008, 0009, and 0011 (all Block 1 only) were measured using a Wyatt Technology DynaPro Plate Reader III was used for the high-throughput size and molar mass measurements. All molecular weights reported in this example are reported as weight average molecular weight ($M_w$). Results are shown FIGS. 7A-C and 8A-B.

Figure 9A:
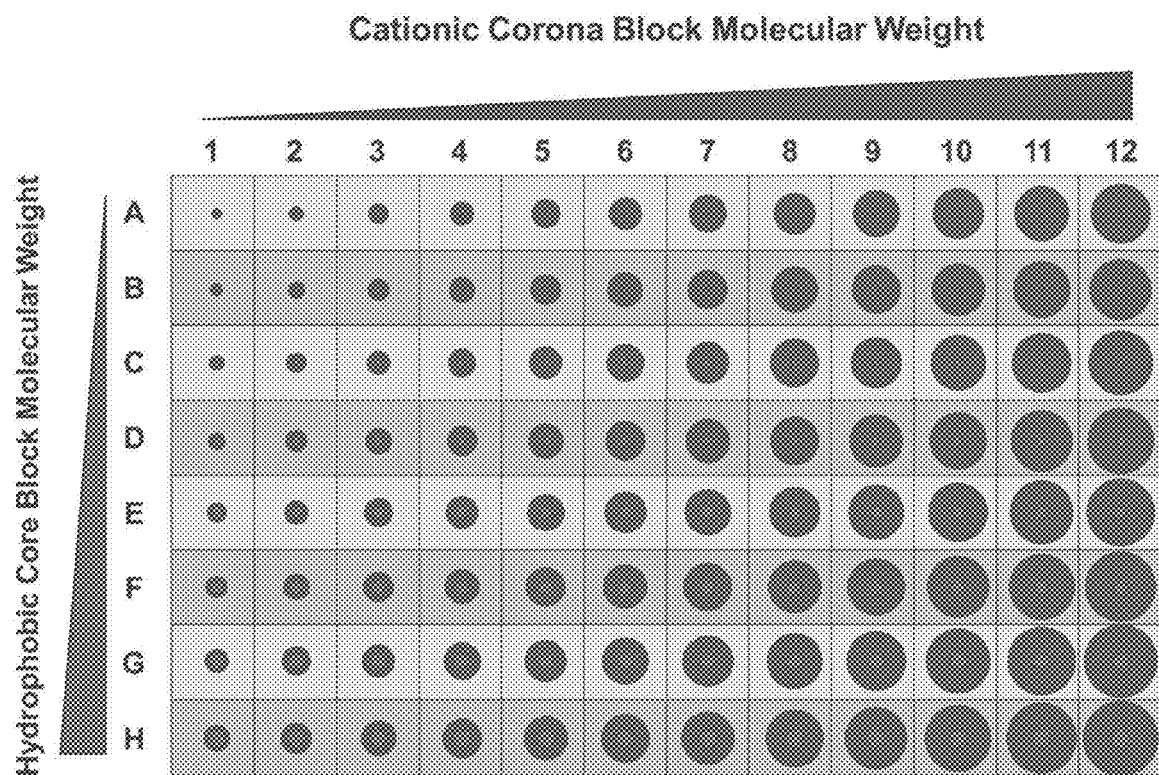
FIG. 9A-C are cartoons showing a 96-well plate having, in each well, the completed Block 1 polymer of varying molecular weights for each of library 0001 (FIG. 9A), 0003 (FIG. 9B), and 0005 (FIG. 9C).
Figure 9B:
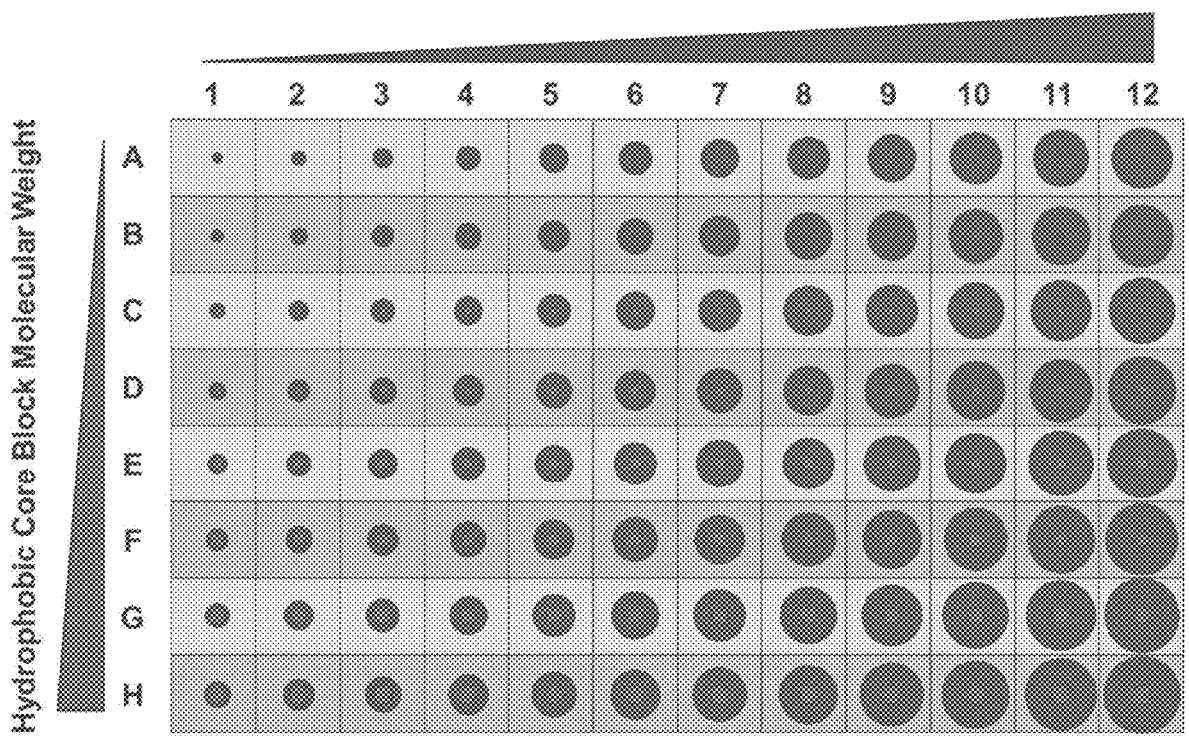
Figure 9C:
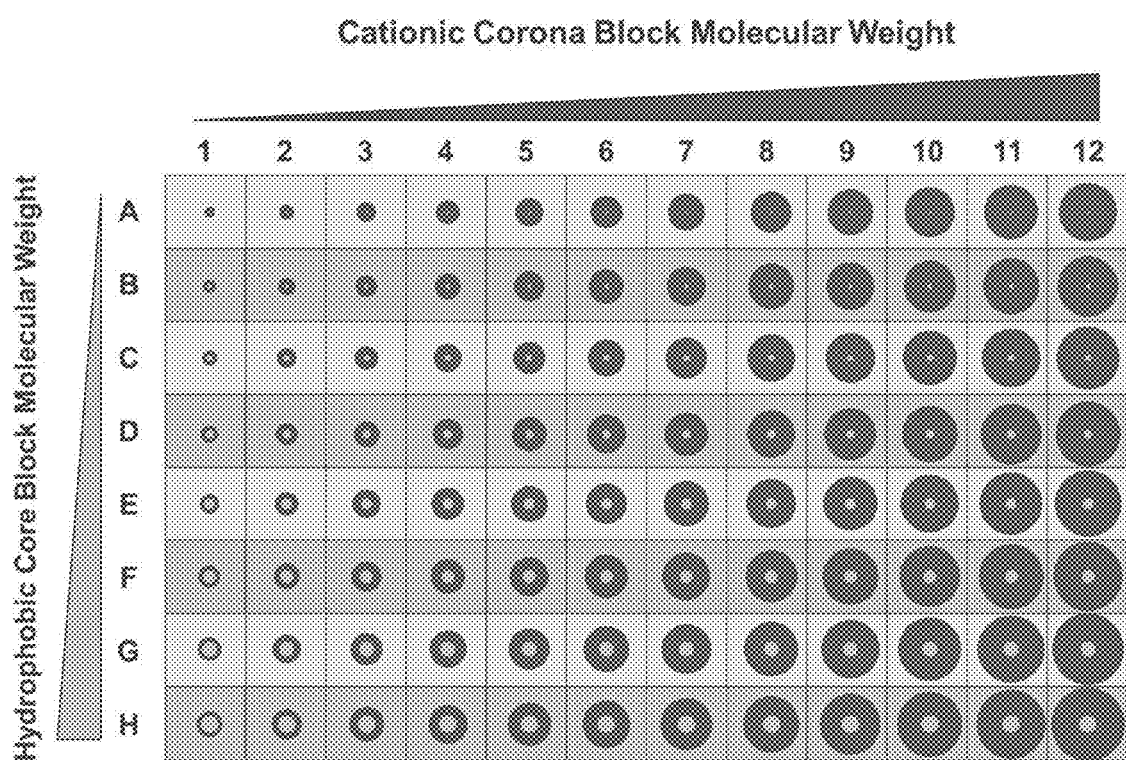

Library Block 1 for libraries 0001, 0003, and 0005 were prepared in 96-well plates as shown in FIGS. 9A-9C.

EXAMPLE 4

4A: Cytotoxicity Assay—DNA Nanostructure

A standard methylthiazolyldiphenyl-tetrazolium bromide (MTT assay) was used to measure cell viability on day 3 (after ~30 hours of exposure to test doses). Approximately 2.4 ml of MTT in cell media at 5 mg/ml was used and 20 ul of the solution was added to each well of the cell plate. The plate was wrapped in foil and incubated for 3 hours. After 3 hours, the plate was removed from incubator and all media was aspirated off with a pipet. 200 ul of isopropanol was added to each well to dissolve the crystals. The plate was wrapped in foil and placed on an orbital shaker for ~5 minutes for full dissolution. The plate was then read in a plate reader at 560 nm and 670 nm. The background at 670 nm was subtracted from the absorbance at 560 nm. Cell viability is reported as a percentage of the absorbance read for cells that were given no treatment (i.e. were dispersed in media only).

The cytotoxicity results for DNA nanostructure delivery compositions are described in Example 2 and the results are FIG. 1F. The results for polymer nanoparticle compositions are shown in FIG. 3. Polymer nanoparticle compositions were not cytotoxic at concentrations below ~73 nM. Lipofectamine was cytotoxic at concentrations above 0.28 vol % of the stock solution. This is equivalent to 0.625 µl per well, which is about 2 times the highest dose recommended by the manufacturer. The two negative controls (PBS and optimum) showed positive cell growth (near 110% cell proliferation) above that of medium only. The two negative controls (9% and 33% ethanol) showed almost complete cell death (~2% cell viability).

4B: Cytotoxicity Assay—Raft Copolymers

Cultured cells in a 96 well plate with at least three empty wells. At least three wells should be absent of media for 12 hrs+for control condition. Grown in sub-confluent monolayers. Used 150 uL of media per a well at time of experiment.

An MTT solution at a concentration of 5 mg/mL in media at a volume equivalent to 25 uL per a sample was prepared. Added 20 uL of MTT solution to each well of the cell plate, including 3 blank wells. Gently shook the plate to mix the solution. Placed lid or 96-well plate sticker over the plate. Wrapped plate with aluminum foil. Sprayed plate down with 70% ethanol and placed in cell incubator (37° C., 5% $CO_2$) for 3-4 hours. After incubation, aspirated off the media from the wells using a Pasteur pipet and the vacuum in the laminar flow hood. Resuspended the formazan (MTT metabolic product) in 200 uL isopropanol. Placed the plate on a shaking plate at a medium speed for at least five minutes, until the crystals dissolved. Ensure the solution does not splash into other wells. Read in a plate reader at 560 nm. Subtracted background at 670 nm (blank wells serve as background).

Figure 10A:
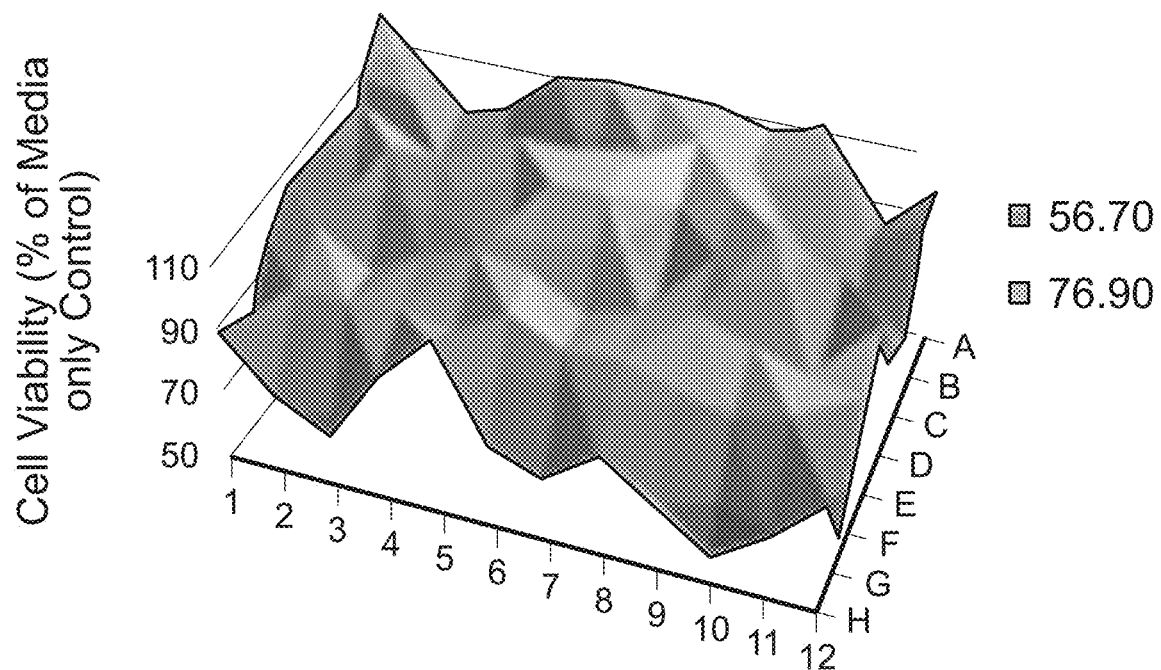
FIG. 10A-C are graphs showing MTT assay results for the completed Block 1 polymer of varying molecular weights for each of library 0001 (FIG. 10A), 0003 (FIG. 10B), and 0005 (FIG. 10C).
Figure 10B:
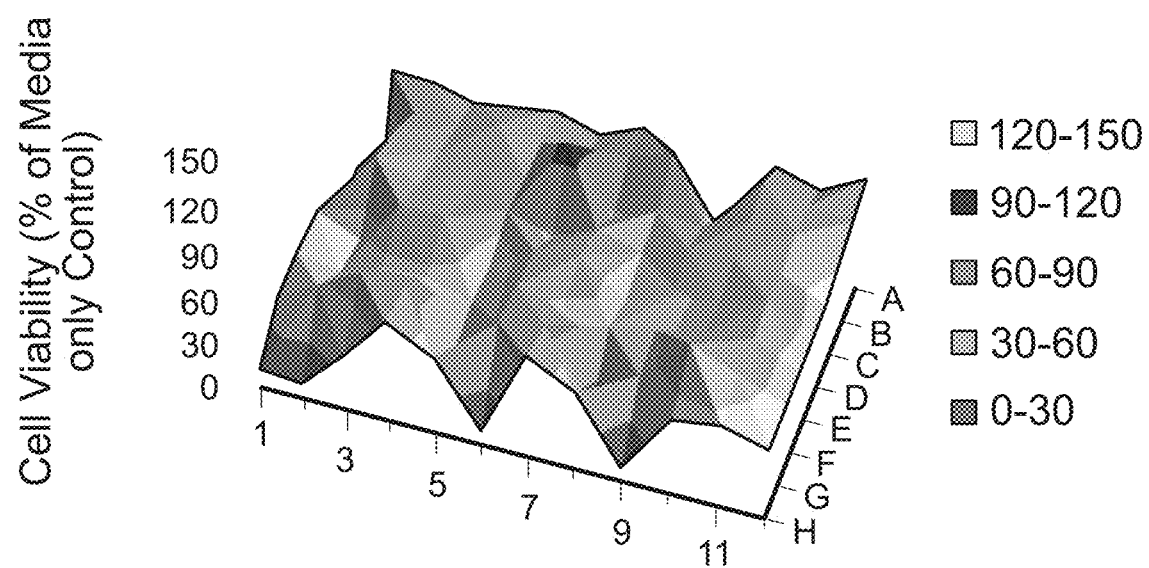
Figure 10C:
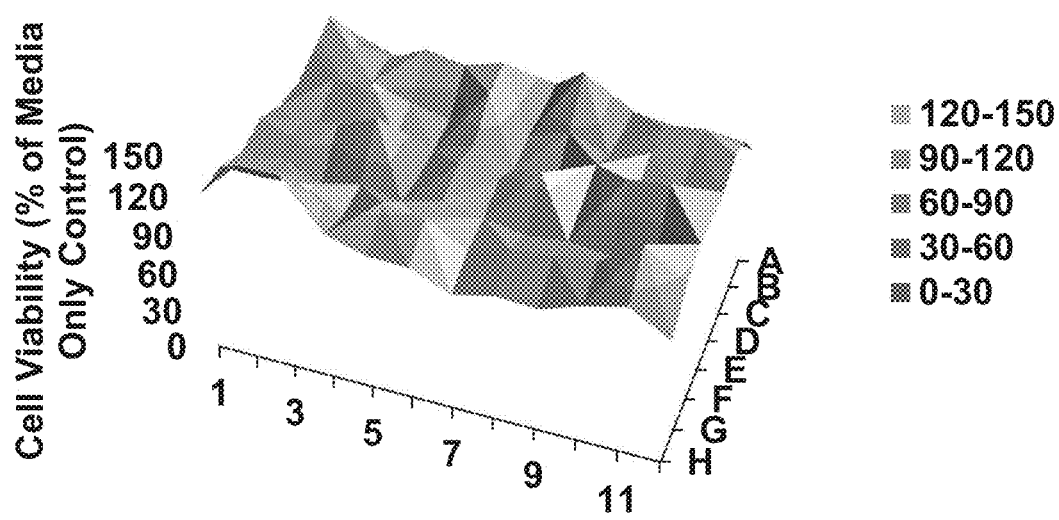

The results of MTT assay for Block 1 of libraries 0001, 0003, and 0005 are shown in FIG. 10A-C. Cell viability of up to 90% was demonstrated.

EXAMPLE 5

HEK Transfection

Figure 4:
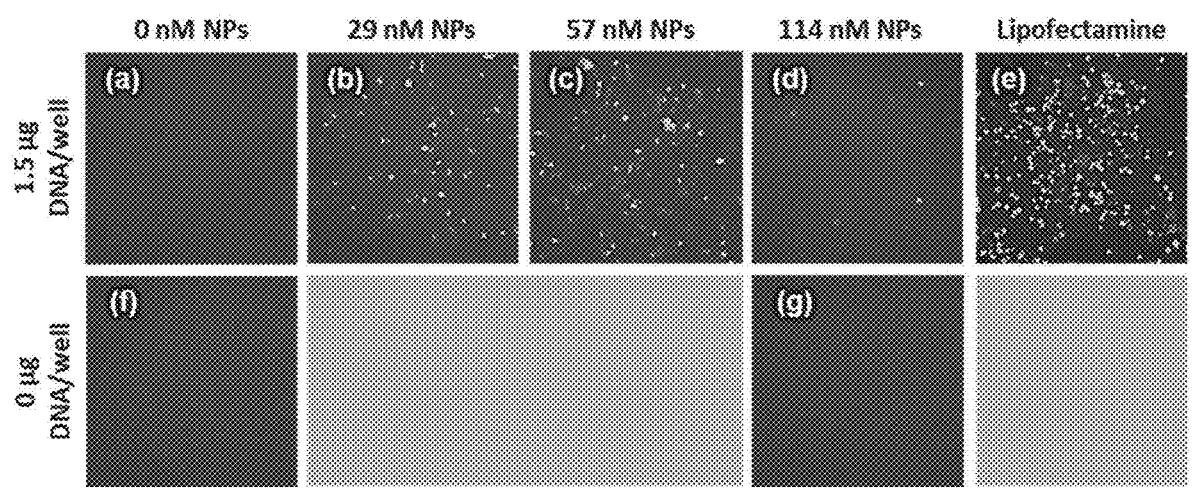
FIG. 4 shows delivery of polymer nanoparticle compositions to HEK-293 cells.

HEK-293T cells were seeded in a 96-well plate at 30,000 cells per well in 0.2 ml of media and left in an incubator at 37 degrees C. overnight. The next day, a serial dilution of polymer nanoparticles was prepared in PBS. Lipofectamine 3000 reagent was prepared according to the manufacturer protocol. The pDNA was added to the dilutions of polymer nanoparticles and lipofectamine to yield 11-fold higher concentrations of both components than those indicated in the images. To each well, 0.02 ml of each dilution was added, to yield an 11-fold dilution. The cells were incubated with the treatments overnight, and fluorescence images were captured with a GFP filter cube set (ex 475 nm, em 509 nm). The dose of polymer nanoparticles (FIG. 4C) showed the most fluorescence and corresponded to a polymer to DNA ratio of ~4, which is consistent with the previous convention. This shows that the polymer nanoparticle platform can be further optimized with our high-throughput platform to deliver genes to cells for treatments.

EXAMPLE 6

DNA Nanostructure Delivery Composition Design

Oligonucleotide staples can be designed for a single stranded DNA scaffold that Is produced from M13 bacteriophage DNA cloned in *Escherichia coli* using fermentation. These oligos can be designed to form, for example, a DNA nanostructure deliver composition (i.e. a DNA origami structure) with a cavity that is ~13×15 nm (the approximate dimensions of an RNP). The oliogo staples can be chosen to include overhangs with sticky ends that will bind to the gRNA of the RNP as well as the ends of the homology directed repair donor DNA strand. The lid on the hinge can be designed with sticky overhangs that will self-anneal after the RNP is loaded, resulting in a compact particle containing all the machinery needed in one particle to effectively deliver multiple payloads, such as the CRISPR RNP to a target cell. Fluorescence microscopy experiments can aid in understanding where the DNA nanostructures traffic within the cells. Using a DAPI (4',6-diamidino-2-phenylindole) blue fluorescent stain, the cell nuclei can be stained blue to examine the extent to which the RNPs co-localize within the nucleus.

DNA Nanostructure Synthesis and Physical Characterization

The surface of the DNA nanostructure can be designed with polyethylene glycol (PEG) polylysine moieties to reduce immunogenicity. There is also potential to include nucleotide "stem-and-loop" features that can take on three-dimensional structures able to bind target cell receptors with or without the help of peptide aptamers. The folding of the DNA nanostructures can be confirmed via transmission electron microscopy (TEM). The loading of the RNP into the DNA nanostructure can be confirmed with a fluorescently labeled RNP (EGFP) and a fluorescence microscope. Particle size, surface charge, and aggregation state can be analyzed in a multi-well plate format via dynamic light scattering. Zeta potential can be analyzed with a Malvern zetasizer.

High Throughput Bioactivity Characterization of the DNA Nanostructure Delivery Compositions The DNA nanostructures loaded with RNP can be assayed in the same array of 96-well plate assays as the polymer nanoparticle compositions. However, in this case, the RNP system can be used to produce green fluorescence in a line of HEK-293 cells that have been modified with a GFP reporter preceded by a stop codon. The gRNA in the RNP can target the stop codon, and when it is disrupted, the cells will report a green fluorescence. A similar test can be done with other cells. For cells that lack the GFP reporter system, the RNP can simply be labeled with EGFP, and the co-localization of the DNA nanostructures in the cells can be evaluated via fluorescence microscopy with DAPI stained cells. If the EGFP fluorescence co-localizes with the blue DAPI stained nuclei, then it is evident that the system was able to deliver the RNP construct. As discussed, the cytotoxic effect on these cells at the doses used can be examined via an MTT cell viability assay. Finally, THP-1 cells and RAW264 cells can be treated with the DNA nanostructures and the immune response can be quantified using ELISA assays for inflammatory cytokines as well as a Greiss assay for a rapid evaluation of inflammatory response associated with nitrous oxide production. The THP-1 cells do not have a strong nitrous oxide production read-out, but the RAW254 mouse cells are sensitive to the inflammation and produce a strong nitrous oxide signal. The bioactivity read-outs can be connected to the physical characteristics and the design parameters of the DNA nanostructures. These results will be used to build the database and predict the design spaces of interest.

What is claimed is:

1. A RAFT block copolymer comprising
   a. a first terminus comprising a first capping unit derived from a first chain transfer agent in a RAFT copolymerization process;
   b. a first block prepared from one or more monomer units covalently attached to the first reactive functional unit, and having a molecular weight ($M_n$) in the range of about 20 kDa to about 80 kDa and a degree of polymerization in the range of about 20 to about 400;
   c. a second block prepared from one or more monomer units covalently attached to the first block, and having a molecular weight ($M_n$) in the range of about 5 kDa to about 80 kDa and a degree of polymerization in the range of about 10 to about 500; and
   d. a second terminus comprising a second capping unit derived from a second chain transfer agent;
   wherein the RAFT block copolymer has one or more of an overall molecular weight ($M_n$) in the range of about 25 kDa to about 160 kDa, and overall degree of polymerization in the range of about 30 to about 900, a size in the range of about of about 10 to about 60 nm, and a maximum corona-to-core ratio (CCR) of about 1 to about 4.

2. The RAFT block copolymer of claim 1, wherein the first block is prepared from one or more monomer units selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

3. The RAFT block copolymer of claim 1, wherein the first block is prepared from one of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, or methyl methacrylate.

4. The RAFT block copolymer of claim 1, wherein the second block is prepared from one or more monomer units selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

5. The RAFT block copolymer of claim 1, wherein the second block is a random copolymer prepared from two different monomer units independently selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

6. The RAFT block copolymer of claim 1, wherein the second block is a random copolymer prepared from three different monomer units independently selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

7. The RAFT block copolymer of claim 1, wherein each chain transfer agent is independently selected from the group consisting of bis(carboxymethyl)trithiocarbonate, bis (2-amino-2-oxoethyl) trithiocarbonate, bis[4-(2-hydroxyethoxycarbonyl)benzyl] trithiocarbonate, 4-cyano-4-(ethylsulfanylthiocarbonyl) sulfanylpentanoic acid, 4-cyano-4-((phenylcarbonothioyl)thio)pentanoic acid, and 4-cyano-4-[(dodecylsulfanylthiocarbonyl)sulfanyl] pentanoic acid.

8. The RAFT block copolymer of claim 1, wherein the first capping unit is of the formula

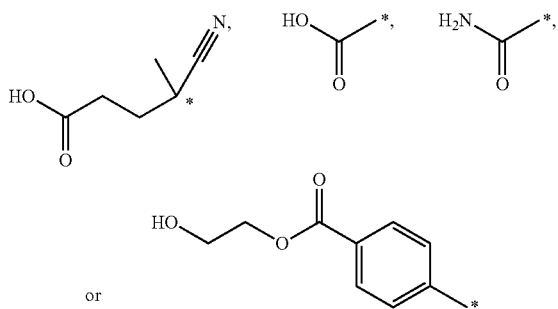

or wherein * represents a point of covalent attachment to the first block.

9. The RAFT block copolymer of claim 1, wherein the second capping unit is of the formula

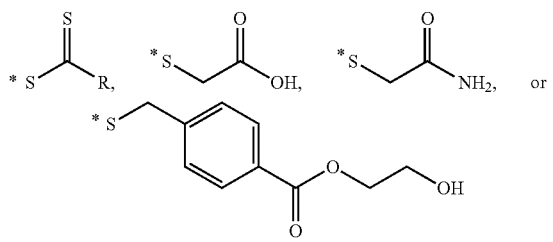

wherein * represents a point of covalent attachment to the second block, and R is —SC$_2$-C$_{12}$ alkyl or C$_6$H$_5$.

10. A RAFT block copolymer conjugate comprising a RAFT block copolymer according to claim 1, and further comprising a biomolecule, drug, or label covalently attached to the RAFT block copolymer through a functional group on one of the first or second chain transfer agents that is incorporated into the RAFT block copolymer.

11. The RAFT block copolymer complex of claim 10, wherein the payload comprises nucleic acids.

12. The RAFT block copolymer complex of claim 10, wherein the nucleic acids comprise DNA or RNA.

13. The RAFT block copolymer complex of claim 10, wherein the nucleic acids comprise a ribonucleoprotein.

14. The RAFT block copolymer complex of claim 10, wherein the payload is a nucleic acid and the nucleic acid payload is of a size selected from the group consisting of 3 kB or more, 3.5 kB or more, 4 kB or more, 4.5 kB or more, 5 kB or more, 5.5 kB or more, 6 kB or more, 6.5 kB or more, 7 kB or more, 7.5 kB or more, 8 kB or more, and 8.5 kB or more.

15. A RAFT block copolymer complex comprising a RAFT block copolymer according to claim 1, and further comprising a payload complexed to the RAFT block copolymer through electrostatic interaction.

16. The RAFT block copolymer complex of claim 15, wherein the payload comprises nucleic acids.

17. The RAFT block copolymer complex of claim 15, wherein the nucleic acids comprise DNA or RNA.

18. The RAFT block copolymer complex of claim 15, wherein the payload is a nucleic acid and the nucleic acid payload is of a size selected from the group consisting of 3 kB or more, 3.5 kB or more, 4 kB or more, 4.5 kB or more, 5 kB or more, 5.5 kB or more, 6 kB or more, 6.5 kB or more, 7 kB or more, 7.5 kB or more, 8 kB or more, and 8.5 kB or more.

19. A method of preparing a RAFT block copolymer comprising:
i. contacting a first chain transfer agent, a first initiator and one or more monomer units to provide a first block;
ii. contacting a second chain transfer agent, a second initiator and one or more monomer units to provide a second block
iii. contacting the first block and the second block under conditions capable of coupling the blocks to provide the RAFT block copolymer.

20. The method of claim 19, wherein the first chain transfer agent is a diamino or dihydroxy chain transfer agent, and the second chain transfer agent is a dicarboxylic acid chain transfer agent.

21. The method of claim 19, wherein the first chain transfer agent is bis(2-amino-2-oxoethyl) trithiocarbonate or bis[4-(2-hydroxyethoxycarbonyl)benzyl] trithiocarbonate, and the second chain transfer agent is bis(carboxymethyl) trithiocarbonate.

22. The method of claim 19, wherein the first chain transfer agent is a dicarboxylic acid chain transfer agent, and the second chain transfer agent is a diamino or dihydroxy chain transfer agent.

23. The method of claim 19, wherein the first chain transfer agent is bis(carboxymethyl)trithiocarbonate, and the second chain transfer agent is bis(2-amino-2-oxoethyl) trithiocarbonate or bis[4-(2-hydroxyethoxycarbonyl)benzyl] trithiocarbonate.

24. The method of claim 19, wherein the one or more monomer units in step (i) are independently selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

25. The method of claim 19, wherein the one or more monomer units in step (i) is one of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, or methyl methacrylate.

26. The method of claim 19, wherein the one or more monomer units in step (ii) are independently selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

27. The method of claim 19, wherein the one or more monomer units in step (ii) are two different monomer units independently selected from the group consisting of 2-dimethylaminoethyl acrylate, 2-(diethylamino) ethyl methacrylate, 2-(diisopropylamino) ethyl methacrylate, butyl methacrylate, ethyl acrylic acid, propyl acrylic acid, (hydroxyethyl)methacrylate, and methyl methacrylate.

28. The method of claim 19, wherein the one or more monomer units in step (ii) are 2-dimethylaminoethyl acrylate, butyl methacrylate, and propyl acrylic acid; or 2-dimethylaminoethyl acrylate and butyl methacrylate; or 2-dimethylaminocthyl acrylate, butyl methacrylate, and ethyl acrylic acid.

29. The method of claim 19, wherein the RAFT block copolymer has one or more of an overall molecular weight ($M_n$) in the range of about 25 kDa to about 160 kDa, and overall degree of polymerization in the range of about 30 to about 900, a size in the range of about of about 10 to about 60 nm, and a maximum corona-to-core ratio (CCR) of about 1 to about 4.

30. A method of preparing a library of RAFT block copolymers comprising:
  i. providing an array of reaction mixtures in a multiwell plate, wherein each well comprises a mixture of a first chain transfer agent, a first initiator, one or more monomer units, and optionally a solvent or solvent mixture;
  ii. reacting the mixture in each well under conditions that promote RAFT copolymerization to provide a series of first block copolymers in the wells of the multiwell plate;
  iii. quenching the reactions in the wells of the multiwell plate;
  iv. purifying the first block copolymer in each well of the multiwell plate;
  v. optionally characterizing the first block copolymer in each well of the multiwell plate;
  vi. optionally purifying the first block copolymer in each well of the multiwell plate;
  vii. contacting to the first block copolymer in each well of the multiwell plate with a second array of reaction mixtures comprising a second chain transfer agent, a second initiator, and one or more monomer units, and optionally a solvent or solvent mixture;
  viii. reacting the components of step (vii) under conditions that promote RAFT copolymerization to provide a series of RAFT block copolymers in the wells of the multiwell plate;
  ix. quenching the reactions in the wells of the multiwell plate;
  x. purifying the RAFT block copolymer in each well of the multiwell plate; and
  xi. optionally characterizing the RAFT block copolymer in each well of the multiwell plate.

* * * * *